US009562094B2

(12) United States Patent
Barden et al.

(10) Patent No.: US 9,562,094 B2
(45) Date of Patent: Feb. 7, 2017

(54) COMPANION ANIMAL TREATMENTS

(75) Inventors: Julian Alexander Barden, North Ryde (AU); Angus Gidley-Baird, North Ryde (AU)

(73) Assignee: BIOSCEPTRE (AUST) PTY LTD (AU)

(*) Notice: Subject to any disclaimer, the term of this patent is extended or adjusted under 35 U.S.C. 154(b) by 322 days.

(21) Appl. No.: 13/821,555

(22) PCT Filed: Sep. 9, 2011

(86) PCT No.: PCT/AU2011/001166
§ 371 (c)(1),
(2), (4) Date: Mar. 7, 2013

(87) PCT Pub. No.: WO2012/031333
PCT Pub. Date: Mar. 15, 2012

(65) Prior Publication Data
US 2013/0266592 A1 Oct. 10, 2013

(30) Foreign Application Priority Data

Sep. 10, 2010 (AU) .............................. 2010904080
Jul. 1, 2011 (AU) .............................. 2011902626

(51) Int. Cl.
*A61K 39/00* (2006.01)
*A61K 39/395* (2006.01)
*C07K 16/00* (2006.01)
*C07K 16/28* (2006.01)
*C07K 16/30* (2006.01)
*C07K 7/08* (2006.01)

(52) U.S. Cl.
CPC ........... *C07K 16/28* (2013.01); *A61K 39/0011* (2013.01); *C07K 7/08* (2013.01); *C07K 16/2869* (2013.01); *C07K 16/30* (2013.01); *A61K 2039/505* (2013.01); *A61K 2039/55505* (2013.01); *A61K 2039/6081* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 6,133,434 A | 10/2000 | Buell et al. | |
| 6,303,338 B1 | 10/2001 | Ni et al. | |
| 6,306,393 B1 | 10/2001 | Goldenberg et al. | |
| 6,329,503 B1 | 12/2001 | Afar et al. | |
| 6,709,832 B1 | 3/2004 | Von Knebel Doeberitz | |
| 7,183,064 B1 | 2/2007 | Slater et al. | |
| 7,326,415 B2 | 2/2008 | Barden et al. | |
| 7,531,171 B2 | 5/2009 | Barden et al. | |
| 7,767,789 B2 | 8/2010 | Gorodeski et al. | |
| 7,888,473 B2 | 2/2011 | Barden et al. | |
| 8,067,550 B2 | 11/2011 | Barden et al. | |
| 8,080,635 B2 | 12/2011 | Barden et al. | |
| 8,293,491 B2 | 10/2012 | Gidley-Baird et al. | |
| 8,399,617 B2 | 3/2013 | Barden et al. | |
| 8,440,186 B2 | 5/2013 | Barden et al. | |
| 8,709,425 B2 | 4/2014 | Barden et al. | |
| 2004/0067542 A1 | 4/2004 | Barden et al. | |
| 2007/0020706 A1 | 1/2007 | Gorodeski et al. | |
| 2007/0248963 A1 | 10/2007 | Slater et al. | |
| 2008/0131438 A1 | 6/2008 | Barden et al. | |
| 2008/0227122 A1 | 9/2008 | Barden et al. | |
| 2009/0215727 A1 | 8/2009 | Douglas | |
| 2010/0036101 A1 | 2/2010 | Gidley-Baird et al. | |
| 2011/0110959 A1 | 5/2011 | Barden et al. | |
| 2011/0111431 A1 | 5/2011 | Slater et al. | |
| 2012/0282278 A1 | 11/2012 | Barden et al. | |
| 2012/0329076 A1 | 12/2012 | Barden et al. | |
| 2013/0171666 A1 | 7/2013 | Gidley-Baird et al. | |
| 2013/0273085 A1 | 10/2013 | Barden et al. | |
| 2014/0135475 A1 | 5/2014 | Barden et al. | |
| 2014/0323693 A1 | 10/2014 | Barden et al. | |
| 2015/0004179 A1 | 1/2015 | Barden et al. | |

FOREIGN PATENT DOCUMENTS

| | | |
|---|---|---|
| AU | 64184/98 B2 | 8/2000 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/50458 A1 | 8/2000 |
| WO | WO 01/06259 A1 | 1/2001 |
| WO | WO 01/30964 A2 | 5/2001 |
| WO | WO 02/48395 A1 | 6/2002 |
| WO | WO 02/057306 A1 | 7/2002 |
| WO | WO 03/020762 A1 | 3/2003 |
| WO | WO 2004/092384 A2 | 10/2004 |
| WO | WO 2007/027957 A2 | 3/2007 |
| WO | WO 2008/043145 A2 | 4/2008 |

(Continued)

OTHER PUBLICATIONS

PCT International Preliminary Report on Patentability of Jan. 16, 2014 for application PCT/AU2012/000795.
PCT International Search Report of Sep. 20, 2012 for applicatin PCT/AU2012/000795.
U.S. Appl. No. 13/391,619, Requirement for Restriction/Election mailed Aug. 5, 2014.
U.S. Appl. No. 13/518,382, Final Office Action mailed Dec. 30, 2013.
U.S. Appl. No. 13/518,382, Notice of Allowance and Examiner Initiated Interview Summary mailed May 5, 2014.

(Continued)

*Primary Examiner* — Christine J Saoud
*Assistant Examiner* — Jon M Lockard
(74) *Attorney, Agent, or Firm* — Alston & Bird LLP

(57) ABSTRACT

The invention relates to minimizing the progression of cancer in a companion animal using P2X7 immunotherapy.

8 Claims, 13 Drawing Sheets

(56) References Cited

FOREIGN PATENT DOCUMENTS

| WO | WO 2008/043146 A1 | 4/2008 |
|---|---|---|
| WO | WO 2009/033233 A1 | 3/2009 |
| WO | WO 2009/033234 A1 | 3/2009 |
| WO | WO 2010/000041 A1 | 1/2010 |
| WO | WO 2011/020155 A1 | 2/2011 |
| WO | WO 2011/075789 A1 | 6/2011 |
| WO | WO 2011/131472 A1 | 10/2011 |
| WO | WO 2012/031333 A1 | 3/2012 |
| WO | WO 2013/003895 A1 | 1/2013 |

OTHER PUBLICATIONS

U.S. Appl. No. 13/626,833, Notice of Allowance and Examiner Initiated Interview Summary mailed Sep. 27, 2013.
U.S. Appl. No. 13/766,630, Notice of Allowance and Examiner Initiated Interview Summary mailed Dec. 11, 2013.
U.S. Appl. No. 13/841,692, Requirement for Restriction/Election mailed Sep. 16, 2014.
Muyldermans et al., "Nanobodies: Natural Single-Domain Antibodies," Annu. Rev. Biochem., 82:17.1-17.23, (2013).
U.S. Appl. No. 13/391,619, Non-Final Office Action mailed Dec. 23, 2014.
U.S. Appl. No. 14/218,935, Non-Final Office Action mailed Sep. 11, 2014.
Supplementary European Search Report and European Search Opinon for application EP10809371.7 (published as EP2467404) mailed Dec. 21, 2012.
Supplementary European Search Report and European Search Opinion for application EP11822941.8 (published as EP2613808) mailed Jan. 7, 2014.
Supplementary European Search Report and European Search Opinion for application EP12807960.5 (published as EP2726095) mailed Dec. 5, 2014.
U.S. Appl. No. 13/841,692, Non-Final Office Action mailed Feb. 26, 2015.
U.S. Appl. No. 60/686,770, filed Jun. 2, 2005, Gorodeski et al.
U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Barden et al., "Specific detection of non-functional human P2X7 receptos in HEK293 cells and B-lymphocytes," FEBS Letters, 538:159-162, (2003).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Buell et al.,"Blockade of Human P2X7 Receptor Function With a Monoclonal Antibody," Blood, 92:3521-3528, (1998).
Burnstock et al., "P2 Purinergic Receptors: Modulation of Cell Function and Therapeutic Potential," J Pharm Exp Therap, 295:862-869, (2000).
Casset et al., "A peptide mimetic of an anti-CD4 monoclonal antibody by rational design," Biochemical and Biophysical Research Communications, 307:198-205, (2003).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and characterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).

Colman, "Effects of amino acid sequence changes on antibody-antigen interactions," Research in Immunology, A Structural View of Immune Recognition by Antibodies, 55th Forum in Immunology, 145:33-36, (1994).
Communi et al., "Cloning and Functional Expression of a Human Uridine Nucleotide Receptor," J Biol Chem, 270(52): 30849-30852, (1995).
Communi et al., "Cloning, Functional Expression and Tissue Distribution of the Human P2Y6 Receptor," Biochem Biophys Res Commun, 222:303-308, (1996).
Dangl et al., "Rapid Isolation of Cloned Isotype Switch Variants Using Fluorescence Activated Cell Sorting," Cytometry, 2:395-401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).
Dixon et al., "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606,(1993).
European Search Report of Sep. 18, 2008 for application EP08156593 (published as EP1961767).
Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al., "ATP stimulates GRK-3 phosphorylation and 3-arrestin-2-dependent internalization of P2X7 receptor," Am J Physiol Cell Physiol, 288:C1342-C1356, (2005).
Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for the Study of Purine and Pyrimidine Metabolism in Man, Abstract and Programme, Jun. 8-11, 2005.
Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides, Nucleotides and Nucleic Acids, 25:1271-1276, (2006).
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).
Foster et al., "Cellular and molecular pathology of prostate cancer precursors," Scand J Urol Nephrol Suppl.,34(205):19-43, (2000).
Galfre et al., "Antibodies to major histocompatability antigens produced by hybrid cell lines," Nature, 266:550-552, (1977).
Galfre et al., "Rat x rat hybrid myelomas and a monoclonal anti-Fd portion of mouse IgG," Nature, 277:131-133, (1979).
Gefter et al., "A simple method for polyethylene glycol-promoted hybridization of mouse myeloma cells," Somatic Cell Genet., 3(2):231, (1977).
GenBank: Accession No. Y09561, versions Y09561.1, "*H. sapiens* mRNA for P2X7 receptor". [Retrieved from the Internet May 24, 2011: <URL: http://www.ncbi.nlm.nih.gov/nuccore/y09561 >].
Georgiou et al., "Human Epidermal and Monocyte-Derived Langerhans Cells Express Functional P2X7 Receptors," J Invest Dermatology,125:482-490, (2005).
Giusti et al., "Somatic diversification of S107 from an antiphosphocholine to an anti-DNA autoantibody is due to a single base change in its heavy chain variable region," PNAS, 84:2926-2930, (1987).

(56) References Cited

OTHER PUBLICATIONS

Greenbaum et al., "Comparing protein abundance and mRNA expression levels on a genomic scale," Genome Biology, 4(9):117.1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296:599-605, (1999).
Gu et al, "A Glu-496 to Ala Polymorphism leads to loss of function of the human P2X7 receptor," J Biol Chem, 276(14):11135-11142, (2001).
Gu et al., "An Arg307 to Gln Polymorphism within the ATP-binding Site Causes Loss of Function of the Human P2X7 Receptor," J Biol Chem, 279 (30):31287-31295, (2004).
Gu et al., "Expression of P2X7 purinoceptors on human lymphocytes and monocytes: evidence for nonfunctional P2X 7 receptors," Am J Physiol Cell Physiol, 279:C1189-C1197, (2000).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2x1)- receptor clusters on smooth muscle cells in relation to nerve varicosities in the rat urinary bladder," J Neurocytol, 27(7): 529-539, (1998).
Holliger et al., "'Diabodies': Small bivalent and bispecific antibody fragments," Proc. Natl. Acad Sci. USA, 90:6444-6448, (1993).
Hopfner et al, "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).
Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).
Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distinct G-protein-coupled ADP Receptors Mediating Platelet Activation," Thromb and Haemost, 81:111-117, (1999).
Jones, "Critically assessing the state-of-the-art in protein structure prediction,"Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and development of P2 receptor subtypes," J Auto Nerv Syst, 81:158-163, (2000).
Kim et al., "Differential Assembly of Rat Purinergic P2X7 Receptor in Immune Cells of the Brain and Periphery," J Biol Chem, 276(26):23262-23267, (2001).
King et al., "Metabotropic receptors for ATP and UTP: exploring the correspondence between native and recombinant nucleotide receptors," TiPS, 19: 506-514, (1998).
Kishore et al., "Cellular localisation of P2Y2 purinoceptor in rat renal inner medulla and lung," Am J Physiol Renal Physiol, 278: F43-F51, (2000).
La Sala et al., "Alerting and tuning the immune response by extracellular Nucleotides," J Leukoc Biol, 73:339-343, (2003).
Lee et al., "P2X receptor immunoreactivity in the male genital organs of the rat," Cell Tissue Res, 300(2): 321-330, (2000).
Li et al., "P2X7 Receptor: A Novel Biomarker of Uterine Epithelial Cancers," Cancer Epidemiol Biomarkers Prev, 15(10):1906-1913, (2006).
MacCallum et al, "Antibody-antigen Interactions: Contact Analysis and Binding Site Topography," J. Mol. Biol., 262:732-745, (1996).
Mager et al., "Prediction of the confirmation of the human P2X7 receptor," Letts Drug Des Discov, 3(10):675-682, (2006).
Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).
Mariuzza et al., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus associated with the t(11;14)(q13;q32) translocation of B-lymphocytic malignancy," Blood, 74:1801-1806, (1989).
Nawa et al., "Frequent loss of expression or aberrant alternative splicing of P2XM, a p53-inducible gene, in soft-tissue tumours," Br J Cancer, 80(8):1185-89, (1999).
Ngo et al "Computational complexity, protein structure prediction, and the Levinthal paradox," in Merz and Le Grand (eds), The protein folding problem and tertiary structure prediction, Birkhauser: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, 3rd Edition, Raven Press, New York, Chapt. 9, pp. 292-295 (1993).
Paul, Fundamental Immunology, Lippincott Williams & Wilkins, p. 107, (1998).
PCT International Preliminary Examination Report of Mar. 14, 2003 for application PCT/AU2001/001614.
PCT International Preliminary Examination Report of May 1, 2003 for application PCT/AU02/00061.
PCT International Preliminary Examination Report of Aug. 1, 2001 for application PCT/AU00/00363.
PCT International Preliminary Examination Report of Dec. 17, 2003 for application PCT/AU02/001204.
PCT International Preliminary Report on Patentability of Jan. 5, 2011 for application PCT/AU09/000869.
PCT International Preliminary Report on Patentability of Mar. 12, 2013 for application PCT/AU2011/001166.
PCT International Preliminary Report on Patentability of Mar. 16, 2010 for application PCT/AU08/001364.
PCT International Preliminary Report on Patentability of Mar. 16, 2010 for application PCT/AU08/001365.
PCT International Preliminary Report on Patentability of Apr. 15, 2009 for application PCT/AU07/001540.
PCT International Preliminary Report on Patentability of Apr. 15, 2009 for application PCT/AU07/001541.
PCT International Preliminary Report on Patentability of Jun. 26, 2012 for application PCT/AU2010/001741.
PCT International Search Report for application PCT/AU2010/001741 mailed Feb. 11, 2011.
PCT International Search Report of Feb. 5, 2002 for application PCT/AU2001/001614.
PCT International Search Report of Apr. 2, 2002 for application PCT/AU02/00061.
PCT International Search Report of Jul. 21, 2000 for application PCT/AU00/00363.
PCT International Search Report of Aug. 7, 2009 for application PCT/AU09/000869.
PCT International Search Report of Sep. 22, 2010 for application PCT/AU10/001070.
PCT International Search Report of Oct. 14, 2002 for application PCT/AU02/001204.

(56) References Cited

OTHER PUBLICATIONS

PCT International Search Report of Oct. 27, 2008 for application PCT/AU08/001364.
PCT International Search Report of Nov. 4, 2011 for application PCT/AU2011/001166.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).
Roman et al., "Cloning and Pharmacological Characterization of the Dog P2X7 Receptor," British Journal of Pharmacology, 158:1513-1526, (2009).
Rudikoff et al., "Single amino acid substitution altering antigen-binding specificity," PNAS, 79:1979-1983, (1982).
Sauer et al., "Calcium-dependence of hydrogen peroxide-induced c-fos expression and growth stimulation of multicellular prostate tumour spheroids," FEBS Lett, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol,199:368-377, (2003).
Sluyter et al., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Supplementary European Search Report and European Search Opinion for application EP08800000 (published as EP2201026) mailed Oct. 29, 2012.
Supplementary European Search Report and European Search Opinion for application EP09771858 (published as EP2318438) mailed Oct. 24, 2012.
Supplementary European Search Report and European Search Opinion for application EP10838429 (published as EP2516470) mailed Apr. 13, 2013.
Supplementary European Search Report of Mar. 4, 2011 for application EP01270623 (published as EP1352085).
Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP00918600 (published as EP1179183).
Supplementary Partial European Search Report of Apr. 29, 2005 for application EP02715313 (published as EP1360203).
Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now U.S. Pat. No. 7,183,064), Final Office Action mailed May 9, 2006.
U.S. Appl. No. 10/019,356 (now U.S. Pat. No. 7,183,064), Non-Final Office Action mailed Jul. 19, 2005.
U.S. Appl. No. 10/019,356 (now U.S. Pat. No. 7,183,064), Notice of Allowance mailed Oct. 11, 2006.
U.S. Appl. No. 10/019,356 (now U.S. Pat. No. 7,183,064), Requirement for Restriction/Election mailed Mar. 18, 2005.
U.S. Appl. No. 10/450,205 (now Abandoned, Publication No. 2004/0067542), Final Office Action mailed Sep. 7, 2007.
U.S. Appl. No. 10/450,205 (now Abandoned, Publication No. 2004/0067542), Non-Final Office Action mailed Dec. 19, 2006.
U.S. Appl. No. 10/450,205 (now Abandoned, Publication No. 2004/0067542), Requirement for Restriction/Election mailed Sep. 6, 2006.
U.S. Appl. No. 10/622,313 (now U.S. Pat. No. 7,326,415), Non-Final Office Action mailed Nov. 30, 2006.
U.S. Appl. No. 10/622,313 (now U.S. Pat. No. 7,326,415), Notice of Allowance and Examiner Interview Summary Record mailed Sep. 5, 2007.
U.S. Appl. No. 10/622,313 (now U.S. Pat. No. 7,326,415), Requirement for Restriction/Election mailed Jun. 16, 2006.
U.S. Appl. No. 11/566,472 (now Abandoned, Publication No. 2007/0248963), Examiner Interview Summary Record mailed Dec. 30, 2009.
U.S. Appl. No. 11/566,472 (now Abandoned, Publication No. 2007/0248963), Final Office Action mailed Jan. 12, 2009.
U.S. Appl. No. 11/566,472 (now Abandoned, Publication No. 2007/0248963), Final Office Action mailed Mar. 9, 2010.
U.S. Appl. No. 11/566,472 (now Abandoned, Publication No. 2007/0248963), Non-Final Office Action mailed Jun. 16, 2008.
U.S. Appl. No. 11/566,472 (now Abandoned, Publication No. 2007/0248963), Non-Final Office Action mailed Aug. 26, 2009.
U.S. Appl. No. 11/566,472 (now Abandoned, Publication No. 2007/0248963), Requirement for Restriction/Election mailed Dec. 17, 2007.
U.S. Appl. No. 11/968,607 (now U.S. Pat. No. 7,531,171), Non-Final Office Action mailed Sep. 26, 2008.
U.S. Appl. No. 11/968,607 (now U.S. Pat. No. 7,531,171), Notice of Allowance mailed Jan. 9, 2009.
U.S. Appl. No. 11/968,607 (now U.S. Pat. No. 7,531,171), Requirement for Restriction/Election mailed Aug. 19, 2008.
U.S. Appl. No. 12/043,083 (now Abandoned, Publication No. 2008/0227122), Non-Final Office Action mailed Nov. 26, 2010.
U.S. Appl. No. 12/043,083 (now Abandoned, Publication No. 2008/0227122), Notice of Allowance mailed Aug. 5, 2011.
U.S. Appl. No. 12/043,083 (now Abandoned, Publication No. 2008/0227122), Requirement for Restriction/Election mailed Jul. 21, 2010.
U.S. Appl. No. 12/417,989 (now U.S. Pat. No. 7,888,473), Non-Final Office Action mailed Jun. 16, 2010.

(56) References Cited

OTHER PUBLICATIONS

U.S. Appl. No. 12/417,989 (now U.S. Pat. No. 7,888,473), Notice of Allowance mailed Sep. 24, 2010.
U.S. Appl. No. 12/445,258 (now Abandoned, Publication No. 2010/0036101), Non-Final Office Action mailed Oct. 18, 2011.
U.S. Appl. No. 12/445,258 (now Abandoned, Publication No. 2010/0036101), Requirement for Restriction/Election mailed May 6, 2011.
U.S. Appl. No. 12/445,273 (now U.S. Pat. No. 8,067,550), Non-Final Office Action mailed Oct. 1, 2010.
U.S. Appl. No. 12/445,273 (now U.S. Pat. No. 8,067,550), Notice of Allowance mailed Mar. 30, 2011.
U.S. Appl. No. 12/445,273 (now U.S. Pat. No. 8,067,550), Notice of Allowance mailed Jul. 8, 2011.
U.S. Appl. No. 12/445,273 (now U.S. Pat. No. 8,067,550), Requirement for.Restriction/Election mailed Aug. 9, 2010.
U.S. Appl. No. 12/677,795 (now U.S. Pat. No. 8,293,491), Notice of Allowance mailed Jun. 22, 2012.
U.S. Appl. No. 12/677,795 (now U.S. Pat. No. 8,293,491), Restriction/Election Requirement mailed Oct. 12, 2011.
U.S. Appl. No. 12/677,799, Non-Final Office Action mailed Jun. 21, 2012.
U.S. Appl. No. 12/677,799, Notice of Allowance and Examiner Interview Summary Record mailed Dec. 10, 2012.
U.S. Appl. No. 12/677,799, Notice of Allowance mailed Jan. 9, 2013.
U.S. Appl. No. 12/677,799, Requirement for Restriction/Election mailed Feb. 23, 2012.
U.S. Appl. No. 12/878,865 (now Abandoned, Publication No. 2011/0111431), Non-Final Office Action mailed Oct. 20, 2011.
U.S. Appl. No. 12/878,865 (now Abandoned, Publication No. 2011/0111431), Requirement for Restriction/Election mailed Mar. 25, 2011.
U.S. Appl. No. 12/975,341 (now U.S. Pat. No. 8,080,635), Non-Final Office Action mailed Mar. 24, 2011.
U.S. Appl. No. 12/975,341 (now U.S. Pat. No. 8,080,635), Notice of Allowance mailed Aug. 17, 2011.
U.S. Appl. No. 13/002,647, Non-Final Office Action mailed Dec. 20, 2012.
U.S. Appl. No. 13/002,647, Requirement for Restriction/Election mailed Aug. 7, 2012.
U.S. Application No. 13/298,222, Final Office Action mailed Sep. 7, 2012.
U.S. Appl. No. 13/298,222, Non-Final Office Action mailed Feb. 13, 2012.
U.S. Appl. No. 13/298,222, Notice of Allowance and Examiner Interview Summary Record mailed Nov. 27, 2012.
U.S. Appl. No. 13/518,382, Non-Final Office Action mailed Jun. 18, 2013.
U.S. Appl. No. 13/518,382, Requirement for Restriction/Election mailed Mar. 21, 2013.
.S. Appl. No. 13/626,833, Non-Final Office Action mailed Jun. 13, 2013.
U.S. Appl. No. 12/677,795 (now U.S. Pat. No. 8,293,491), Non-Final Office Action mailed Feb. 29, 2012.
Uniprot entry Q4VKI0_Human P2X7 Isoform E, UniProt Consortium, (2005).
Uniprot entry Q4VKI1_Human P2X7 Isoform F, UniProt Consortium, (2005).
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol., 519(2):335-346, (1999).
von Kugelgen et al., "Molecular Pharmacology of P2Y-receptors," Naunyn Scmiedebergs Arch Pharmacol, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al ., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11)17, (2000). Abstract.
Wiley et al., "An Ile-568 to Asn polymorphism prevents normal trafficking and function of the human P2X7 receptor," J Biol Chem 278 (19):17108-17113, (2003).
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Worthington et al., "Point mutations confer loss of ATP-induced human P2X7 receptor function," FEBS Lett, 512:43-46, (2002).
Wurl et al., "High prognostic significance of Mdm2/p53 co-overexpression in soft tissue sarcomas of the extremities," Oncogene,16(9):1183-85, (1998).
U.S. Appl. No. 13/002,647, Notice of Allowance mailed Aug. 2, 2013.
U.S. Appl. No. 13/766,630, Non-Final Office Action mailed Aug. 19, 2013.
U.S. Appl. No. 13/518,382, Non-Final Office Action mailed Sep. 18, 2013.
Uniprot sequence entry: Accession No. Q4VKH8, "P2X7 isoform H," Jul. 2005. [Retrieved from the Internet Sep. 9, 2013: <URL: http:// www.ncbi.nlm.nih.gov/protein/Q4VKH8>].
Uniprot sequence entry: Accession No. Q4VKH9, "P2X7 isoform G," Jul. 2005. [Retrieved from the Internet Sep. 9, 2013: <URL: http:// www.ncbi.nlm.nih.gov/protein/Q4VKH9>].
Uniprot sequence entry: Accession No. Q4VKI2, "P2X7 isoform D," Jul. 2005. [Retrieved from the Internet Sep. 9, 2013: <URL: http:// www.ncbi.nlm.nih.gov/protein/Q4VKI2>].
Uniprot sequence entry: Accession No. Q4VKI4, "P2X7 isoform B," Jul. 2005. [Retrieved from the Internet Sep. 9, 2013: <URL: http:// www.ncbi.nlm.nih.gov/protein/Q4VKI4>].

Figure 1 (SEQ ID No:1)

```
  1    MPACCSCSDV FQYETNKVTR IQSMNYGTIK WFFHVIIFSY VCFALVSDKL YQRKEPVISS

61    VHTKVKGIAE VKEEIVENGV KKLVHSVFDT ADYTFPLQGN SFFVMTNFLK TEGQEQRLCP

121    EYPTRRTLCS SDRGCKKGWM DPQSKGIQTG RCVVHEGNQK TCEVSAWCPI EAVEEAPRPA

181    LLNSAENFTV LIKNNIDFPG IINYTTRNILP GLNITCTFHK TQNPQCPIFR LGDIFRETGD

241    NFSDVAIQGG IMGIEIYWDC NLDRWFHHCR PKYSFRRLDD KTTNVSLYPG YNFRYAKYYK

301    ENNVEKRTLI KVFGIRFDIL VFGTGGKFDI IQLVVYIGST LSYFGLAAVF IDFLIDTYSS

361    NCCRSHIYPW CKCCQPCVVN EYYYRKKCES IVEPKPTLKY VSFVDESHIR MVNQQLLGRS

421    LQDVKGQEVP RPAMDFTDLS RLPLALHDTP PIPGQPEEIQ LLRKEATPRS RDSPVWCQCG

481    SCLPSQLPES HRCLEELCCR KKPGACITTS ELFRKLVLSR HVLQFLLLYQ EPLLALDVDS

541    TNSRLRHCAY RCYATWRFGS QDMADFAILP SCCRWRIRKE FPKSEGQYSG FKSPY
```

Figure 2A

CLUSTAL 2.0.12 multiple sequence alignment

```
African clawed frog   ---MTLT--LADCFDYSTKKEVRIQSVPLGILKQCITFGVIVFVCFSLITQKRYQKKDSI  55
Western clawed frog   ---MAPT--FADCFDYSTKKEIRIQSVPLGVLKFLITFGVILFVCFSLITQKSYQKKVSV  55
Chicken               ---MVAWGWMKDVFNYESPKLIRFPSVGLVCVKWFIYGVIAVYICYTLIVHKRYQEKEEL  57
Rat                   MLPVRHLCSYN-----SAKVLIHSTRLGALKNFFLLAICIYICFALMSDKLYQRKEPL   54
human                 ---MPACCSCSDVFQYETNKVTRIQSMNYGTIKWFFHVIIFSYVCFALVSDKLYQRKEPV  57
dog                   ---MSACCSCNDIFQYETNKIIRIQSMNYGTIKWIFHVIIFSYISFALISDKRYQQKEPL  57
mouse                 -GLCRACCSWNDVLQYETNKVTRIQSTNYGTVKWVLHMIVFSYISFALVSDKLYQRKEPV  59
chimpanzee            ---MPACCSCSDVFQYETNKVTRIQSMNYGTIKWFFHVIIFSYVCFALVSDKLYQRKEPV  57
Macaque               ---MPACCSCSDVFQYETTKVTRIQSMNYGTIKWFFHVIVFSYVSFALVSDKLYQRKEPV  57
Marmoset              ---MPACCSCSDVFQYETNKVTRIQSMNYGTLKWFFHVIVFSYVSFALVSDKLYQRKESV  57
Panda                 ---MPACCSWKDVFQYETNKVLRIQSTNYGTIKWIFHVLFSYISFALISDKRYQKKEPL  57
horse                 ---MPACCSWNDVFQYETNKVTRIQSMNYGTIKWICHLIVFSYVIFALVSDKRYQRKEPL  57
cattle                ---MTACCSWNDVFQYETNKIIWIQSKTYGTIKWLFHVVLFSYIGFALVSDKRYQRKEPV  57
rabbit                ---MPACCSWNDVFQYETNKVARIQSVNYGTIKWVLHVIVFSYVSFALVSDKLYQRKEPV  57
Guinea pig            ---MPGCSCWDDVFQYETNKVTRIQSRNYGTLKWVLHLIVFSYISFALVTDKMYQRKEPV  57
Opossum               ---MWPCCSWRDICKYETTKVIRVESMTYGTLRWSLCAIVFFYVCVGLLSDKLYQRKEPL  57
Sea bream             ---MPCCGLRGLRQYETNKLVRIQSVRLGSMKWSLNGFILLFICIMMLWNRKYQEFDLV  56
zebrafish             ---MPCVLLN-LCEYDTQKLVKIKSVKLGSLKWTLNGVILMFICIMMLWNKEYQEYDFV  55
                          .    *       :  : *           :     :.         ::  :  **.  ::
```

Figure 2B

```
African clawed frog  ISSVHTKVKGFADAHS--------------RIWDTAEYTVPSPGGDSFFVITNIVKTEGQMQ  103
Western clawed frog  ISSVHTKVKGIADAYS--------------RIWDTAEYTVPSPGGDSFFVTNIVKTEDQRQ  103
Chicken              TSSVRVTLKGVAHVD---------------RIWDAAEYTIPTQTRDSFFVMTNIIRTENQIQ 104
Rat                  ISSVHTKVKGVAEVTENVTEGGVTKLVHGIFDTADYTLPLQ-GNSFFVMTNYLKSEGQEQ   113
human                ISSVHTKVKGIAEVKEEIVENGVKKLVHSVFDTADYTFPLQ-GNSFFVMTNFLKTEGQEQ   116
dog                  ISSVHTKVKGTAEVKMEILENGIKKMVSTVFDTADYTFPLQ-GNSFFVMTNFLKTEGQQQ   118
mouse                ISSVHTKVKGIAEVTENVTEGGVTKLGHSIFDTADYTFPLQ-GNSFFVMTNYVKSEGQVQ   116
chimpanzee           ISSVHTKVKGIAEVKEEIVENGVKKLVHSVFDTADYTFPLQ-GNSFFVMTNFLKTEGQEQ   116
Macaque              ISSVHTKVKGTAEVKEEIVENGVKKLVHSVFDTADYTFPLQ-GNSFFVMTNFLKTEGQEQ   116
Marmoset             ISSVHTKVKGIAEVKEEIVENGVKKLVHHVFDTADYTFPLQ-GNSFFVMTNFLKTEGQEQ   116
Panda                ISSVHTKVKGIAEVKAEILENGMKKMVSGVFDTADYTFPLQ-GNSFFVMTNFIKTEGQQQ   116
horse                ISSVHTKVKGIAEVREEIIESGAKKVVQSVFDTADYTFPLQ-GNSFFVMTNFLKTEGQEQ   116
cattle               ISSVHSKIKGIAEVKKEIMENGQTKVVQSVFDMADYTFPLQ-GNSFFMMTNFLKTEGQEQ   116
rabbit               ISSVHTKVKGIAEVKKEIVENGVLVENGVG-GVRRSVQKVLDTADYTLPLQ-RNSFFVMTNFLKTEGQER 116
Guinea pig           ISSVHSKVKGMAEVTEEVVG-GVRRSVQKVLDTADYTLPLQ-GNSFFVMTNYLQTEGQER   115
Opossum              ISSVQTKVKGIAEVK-----NGNSK--TRVLDTADYTIPLQ-GNSFFVMTNFISTEGQTQ   109
Sea bream            VSSVHTKVKGVAQT-------------LGDMVWDVVDYSGPSHDKNSFFVVTNVIVTKNQKQ 105
zebrafish            VSSVTTKVKGVAKITL-----------PEVGDVVWDVVDYSGPSQGKNSFFVATNAIVTKNQKQ 108
                     ***  :**  *.             .  *    .:*:  *   .:****: .  :     ::
```

Figure 2C

```
African clawed frog  SNCSELPSQKTICSRDDICKKGLADPQSNGIQTGRCINFNNTLKTCEVSAWCPVES-QTT  162
Western clawed frog  SNCPELPRQKTICSRDDVCKKGLADPQSNGIQTGRCINFNSTLKTCEVSAWCPVES-QTT  162
Chicken              KTCPEYPTAKAICSSDKSCAKGIVDVHSNGVQTGKCVHYNITHKTCEIKAWCPVQGEERP  164
Rat                  KLCPEYPSRGKQCHSDQGCIKGWMDPQSKGIQTGRCIPYDQKRKTCEIFAWCPAEEGKEA  173
human                RLCPEYPTRRTLCSSDRGCKKGWMDPQSKGIQTGRCVVYEGNQKTCEVSAWCPIEAVEEA  176
dog                  GFCPEFPTRRTLCSNDWGCKKGWMDPQSKGIQTGRCIEYKGKQKTCEVSAWCPIEAVEEA  176
mouse                TLCPEYPRRGAQCSSDRRCKKGWMDPQSKGIQTGRCVPYDKTRKTCEVSAWCPTEEEKEA  178
chimpanzee           RLCPEYPTRRTLCSSDRGCKKGWMDPQSKGIQTGRCVVYEGNQKTCEVSAWCPIEAVEEA  176
Macaque              RLCPEYPTRRTLCSSDRGCKKGWMDPQSKGIQTGRCVVYEGNRKTCEVSAWCPIEAVGEA  176
Marmoset             QLCPEYPTRRTLCSSDRGCKKGWMDPQSKGIQTGRCVVYKGNQKTCEVSAWCPIEAVEDA  176
Panda                GLCPDFPTRRTICSSDRGCKKGRMDPQSKGIQTGRCVVYKERLKTCEVSAWCPIEEVEDA  176
horse                GLCPEYPTRRTLCSSDRGCKKGWMDPQSKGIQTGRCIVYKGNQKTCEVSAWCPIEAVEEA  176
cattle               GLCPEYPTRRTLCSSDRGCKKGWLGPRSKGIQTGRCIHYNEKQKTCEVFTWCPVEAEEKA  176
rabbit               RLCPEYPTRRTLCSSDRGCRKGWMDPQSKGIQTGRCVVYKGNQKTCEVSAWCPIEAAEDA  176
Guinea pig           GLCPEYPTPRTRCSSDRGCKKGWRDPKSKGIQTGRCVVYSGTTKTCEVAAWCPVEAVIEA  175
Opossum              GLCPEYPTRRTLCSTDQGCKKGKKDPLSKGIQTGKCVLYSTTQKTCEVSAWCPVEQERDA  169
Sea bream            GKCPEVLRIGRLCRTDKDCGRGAWDQQSHGIQTGSCVISDVSKKTCEVSAWCPIEKRGNP  165
zebrafish            GNCAEILPNGKLCRTDKDCEKGFSDQHSHGVQTGACVKLEILKKTCEVTAWCPIENKKNP  168
                      *  .        *    *  .:*   *:****  **  .  ::****  ::
```

Figure 2D

```
African clawed frog  PVPAVLESAENFTVLIKNNIHFAAFNFTKKNILPNYN----VSCIYDRVKAPLCPIFRLG  218
Western clawed frog  PVPAVLESAENFTVLIKNNIHFAAFNFTKKNILPKYN----VSCIYDRVKAPLCPIFRLG  218
Chicken              PVPAVLRSSEDFTVFIKNNIHFPTENYTVQNISPKLN----TSCKFNKVTAPLCPIFRLG  220
Rat                  PRPALLRSAENFTVLIKNNIDFPGHNYTTRNILPGMN----ISCTFHKTWNPQCPIFRLG  229
human                PRPALLNSAENFTVLIKNNIDFPGHNYTTRNILPGLN----ITCTFHKTQNPQCPIFRLG  232
dog                  PRPALLNGAENFTVLIKNNIDFPGHNYTTRNILPDIN----ITCTFHKTQNPQCPIFRLG  232
mouse                PRPALLRSAENFTVLIKNNIHFPGHNYTTRNILPTMN----GSCTFHKTWDPQCSIFRLG  234
chimpanzee           PRPALLNSAENFTVLIKNNIDFPGHNYTTRNILPGLN----ITCTFHKTQNPQCPIFRLG  232
Macaque              PRPALLNSAENFTVLIKNNIDFPGHNYTTRNILPGLN----ITCTFHKTQNPQCPIFRLG  232
Marmoset             PRPALLNSAENFTVLIKNNIDFPGHNYTTRNILPGLN----ITCTFHKTQNPQCPIFRLG  232
Panda                PRPALLNSAENFTVLIKNNIDFPGHNYTTRNILPGVN----ITCTFHKTQNPQCPIFRLG  232
horse                PRPALLNSAENFTVLIKNNIDFPGHNYTTRNFLPGLN----ITCTFHKTQNPQCPIFRLG  232
cattle               PEPALLVSAENFTVLIKNNIDFPGHNYTTRNILPGLN----TTCTFHKTRDPQCPIFRLG  232
rabbit               PRPALLGSAENFTVLIKNNIDFPGHNYTTRNIPPGLN----ISCTFHKTQNPQCPIFRLG  232
Guinea pig           PRPAILSSAENLTVLIKNNVHFPGHNYTTRNILPGLN----ASCTFHKTKNPECPIFRLG  231
Opossum              PRPALLISAANFTVLIKNNIDFPGHNYTTRNILPGVN----ITCMFHRTHNPQCPIFRLG  225
Sea bream            PRPALLAAAEDFTVLIKNNIRFPAFNFIRRNILPTMNGAYLSSC--QRVNDSLCPIFRLG  223
zebrafish            -RPALLAAAENFTVMIKNNIRFPAFNYIRRNILSEMKDTDFKGCIYHRYKNPYCPIFRLG  227
                      **:.* .::.:****..*   ..  *:  .        *.  .   .  * .******
```

Figure 2E

```
African clawed frog  DILREAGENFSQVAVLGGVIGIEINWDCDLDPLRYKCEPHYGFRRLDDT-VVDESLYPGL 277
Western clawed frog  DILREAGENFSQVAVLGGVIGIEINWDCDLDSLRYKCEPHYSFRRLDDK-VVDERLYPGL 277
Chicken              DILQEAKENFSEMAVKGGIIAIEIKWDCDLDSWSYYCSPEYSFRRLDDK-TRTQ--YPGF 277
Rat                  DIFQEIGENFTEVAVQGGIMGIEIYWDCNLDSWSHRCQPKYSFRRLDDK-YTNESLFPGY 288
human                DIFRETGDNFSDVAIQGGIMGIEIYWDCNLDRWFHHCRPKYSFRRLDDK-TTNVSLYPGY 291
dog                  DIFQQTGDNFSDVAIQGGIMGIEIHWDCNLDSWFHHCRPKYSFRRLDDKNTTTESLYPGY 292
mouse                DIFQEAGENFTEVAVQGGIMGIEIYWDCNLDSWSHHCRPRYSFRRLDDK-NTDESFVPGY 293
chimpanzee           DIFRETGDNFSDVAIQGGIMGIEIYWDCNLDRWFHHCRPKYSFRRLDDK-TTNVSLYPGY 291
Macaque              DIFRETGDNFSDVAIQGGIMGIEIYWDCNLDRWFHHCRPKYSFRRLDDK-TTNVSLYPGY 291
Marmoset             DVFRETGDNFSEVAIQGGIMGIEIYWDCNLDRWFHHCRPKYSFRRLDDK-TTNESLYPGY 291
Panda                DIFETGDNFSDVAIQGGIMGIEIYWDCNLDGWFHHCRPKYSFRRLDDK-TTNESLYPGY 291
horse                DIFRETGDHFSDVAIQGGIMGIEIYWDCNLDRWFHHCRPKYSFRRLDDK-TASESSYPGY 291
cattle               DIFQETGDNFSEVAIQGGIMGIEIYWDCNLDRWFHHCRPKYSFRRLDDK-TAKESLYPGY 291
rabbit               DIFRETGDRFSDVAVQGGIMGIEIYWDCNLDRWFHRCRPKYSFRRLDDK-TANESLYPGY 291
Guinea pig           DIFQEAGDNFSDVAVQGGIMGIEINWDCNLDKWSHHCRPKYSFRRLDDK-SVEEILVPGY 290
Opossum              DIQEVGENFSDVAVQSEIMSIEIYWNCNLDSWFHSCRPKYSFRRLDDR-TTIESLYPGY 284
Sea bream            DIAREAGEKFSEMAVEGGVIGILIKWDCNLDWLMQRCLPKYSFRRLDEK-ESNRTLYPGL 282
zebrafish            DIVAEAKEKFSEMAVEGGVIGIQINWDCDLNRFFHSCLPKYSFRRLDEK-ESNRTLYPGL 286
                     *.:  ..  ..*:::*..  . :::.:* * :   .*  .:*.*****::        **
```

Figure 2F

```
African clawed frog  NFRFARYYKNAHGTETRTLIKAYGIRFDIQVYGTGGQFNLLELALFIGSCLSYFGCASFA  337
Western clawed frog  NFRFARYYKTSDGKETRTLIKAYGIRFDIQVYGMGGKFNLFELAIFIGSCLSYFGCASLA  337
Chicken              SIRFARHYKLPDGTEQRTLFKAYGIRFDVLVFGMGGQFKLIELFTFIGSTIAYFGLAVTI  337
Rat                  NFRYAKYYKE-NGMEKRTLIKAFGVRFDILVFGTGGKFDIIQLVVYIGSTLSYFGLATVC  347
human                NFRYAKYYKE-NNVEKRTLIKVFGIRFDILVFGTGGKFDIIQLVVYIGSTLSYFGLAAVF  350
dog                  NFRYAKYYKE-NNVEKRTLIKVFGIRFDILVFGTGGKFDIIQLVVYIGSTLSYFGLATLF  351
mouse                NFRYAKYYKE-NNVEKRTLIKAFGIRFDILVFGTGGKFDIIQLVVYIGSTLSYFGLATVC  352
chimpanzee           NFRYAKYYKE-NNVEKRTLIKVFGIRFDILVFGTGGKFDIIQLVVYIGSTLSYFGLATVF  350
Macaque              NFRYAKYYKE-NNVEKRTLIKVFGIRFDILVFGTGGKFDIIQLVVYIGSTLSYFGLATVF  350
Marmoset             NFRYAKYYKE-NNVEKRTLIKVFGIRFDILVFGTGGKFDIIQLVVYIGSTLSYFGLATVF  350
Panda                NFRYAKYYKE-NNVEKRTLIKVFGIRFDILVFGTGGKFDIIQLVVYIGSVISYFGLATVF  350
horse                NFRYAKYYKE-NNVEKRTLIKVFGIRFDILVFGTGGKFDIIQLIVFVGSTLSYFGLATLF  350
cattle               NFRYAKYYKE-NNTEKRTLIKAYGIRFDILVFGTGGKFDIIQLIVYIGSTLSYFGLATVF  350
rabbit               NFRYAKYYKE-NNVEKRTLIKVFGIRFDILVFGTGGKFDIIQLIVYIGSTLSYFGLATVC  350
Guinea pig           NFRFARYYRE-NNVEKRTLIKVFGVRFDILVFGTGGKFDIISLIVYIGSTLSYFGLATVF  349
Opossum              NFRFARYYKE-GNVEKRDLIKAFGIRFDILVFGTGGKFDFIQMVVYIGSTLSYFGLATVF  343
Sea bream            NFRYAKYNTV-NGVEERTLYKAFGIRFDVMVFGQAGKFSFIQLIIYIGSTLSYYALTTML  341
zebrafish            NFRFARYSTV-NGVEQRTLFKMYGIRFDVMVFGKAGKFSIIQLIIYIGSTLSYYAITTIF  345
                     .:*::::     . :*..* *.:*:*****.:*: *::::...:  ::** :**::.. ..
```

Figure 2G

```
African clawed frog  IDFIIGRYN---------------SCCCNAKSVLKYDDRKYETIPGPSVS---LAHLKAHLKF  383
Western clawed frog  IDFIIGLYK---------------PCCCNAKSVLKYYDDRKYEKVPGPTVAQVKYCHFLSQLKF  386
Chicken              IEMCFHLYN---------------CSSCCKIQVCENVIRKKYETVLMP------EQVIL        375
Rat                  IDLIINTYASTCCRSRVYPSCKCCEPCAVNEYYRKKCEPIVEP-----------KPTLKY       397
human                IDFLIDTYSSNCCRSHIYPWCKCCQPCVVNEYYRKKCESIVEP-----------KPTLKY       400
dog                  IDFLINTYSSKCCRSHIYPCFKCCEYCAVNEYYRKKCETIVEP-----------KPTLKY       401
mouse                IDLLINTYSSAFCRSGVYPYCKCCEPCTVNEYYRKKCESIMEP-----------KPTLKY       402
chimpanzee           IDFLIDTYSSNCCRSHIYPWCKCCQPCVVNEYYRKKCESIVEP-----------KPTLKY       400
Macaque              IDFLINTYSSNYCRSHIYPWCKCCQPCVVNEYYRKKCESIVEP-----------KPTLKY       400
Marmoset             IDFLINTYSSNCCRSHIYPWCKCCRPCVVNEYYRKKCESIVEP-----------KPTLKY       400
Panda                IDILINTYSSKCCRSRIYPCFKCCEYCAVNEYYRKQSEPIAEP-----------KPTLKY       400
horse                IDFLINTYSSKFCRSSIYPCCKYCEPCSVNEYYRKKCESIVEP-----------KPTLKY       400
cattle               IDMLINTYSSKYCRSHVYPWCKCCQPCAVNEYYKKKYESIVEP-----------TRTLKY       400
rabbit               IDFLINTYSSNCCRSHIYPRCTCCEPCAANEYYHRKKYESLVEP----------RRTLKY       400
Guinea pig           IDFLINTYSSALCRSHVYPWCPCCKPCAANEYYRKKCQATVEP----------KPTLKY        399
Opossum              IDFLIDTYSSTCCRTHVYPCCKACEPCGVNEYYRKKCETIEEP----------KPTLKY        393
Sea bream            IDWLI-------------------GTSCYSVEVGQNYSEKKVEAVQDK------QKCILC       376
zebrafish            LDWLI-------------------GTGCYSKEAKQNYTERKFEAVQDR------EECFLC       380
                     ::   :                      *                                     .
```

Figure 2H

```
African clawed frog  VSFVDKEDILMVDQKLKG-SLQLASGPYIQRER--FADTKAKCKDSHKQD---------  430
Western clawed frog  VSFVDKEDILMVDINSRG-SLQFASGQHIQRER--FEYTEAKCKDSHKKN---------  433
Chicken              VSYVDKPHITLIKMPLRT-SLQNAEGSIFEDHP--VKSYDPRTCCSHKSNEK-------  424
Rat                  VSFVDEPHIWMVDQQLLGKSLQDVKGQEVPRPQTDFLELSRLSLSLH-HSPP-------  448
human                VSFVDESHIRMVNQQLLGRSLQDVKGQEVPRPAMDFTDLSRLPLALH-DTPP-------  451
dog                  VSFVDEAHIRMVDQQLLRRRLQDVEGEEVPRPSMEFTDLSRLSLSLH-DLSP-------  452
mouse                VSFVDEPHIRMVDQQLLGKSLQVVKGQEVPRPQMDFSDLSRLSLSLH-DSPP-------  453
chimpanzee           VSFVDESHIRMVNQQLLGRSLQDVKGQEVPRPAMDFTDLSRLPLALH-DTPP-------  451
Macaque              VSFVDESHIRMVNQKLLGRSLQDVKGQEVPRPAMDFTDLSKLPLALH-DPPP-------  451
Marmoset             VSFVDESHIRMVNQQLLGRRLQDVKGQEVPRPVDFTDLSKLPLALH-DPPP--------  451
Panda                VSFVDETHIRMVDQQLLGKSLQNVKGEKVQRPSVDFTDLSRLSLSLC-DPTP-------  451
horse                VSFVDESHIRMVDQQLLGRSLQDVKGEKVPRPSMDFTDLSRLPLSLQ-DPHV-------  451
cattle               VSFVDEPCIRMVNERLLGTSLQAVKGEKVLRPQLDFADLSWLHLSLH-DSPP-------  451
rabbit               VSFVDEPHIRMVDQQLLGKSLQDVPGQKIPRPRDFTDLSKLPLSFL-DPHP--------  451
Guinea pig           VSFVDEPHIRMVDQRLLGKSLQYVKGQKVPRPPTDFTLLSKLPTSPP-DPAP-------  450
Opossum              VSFVDEPHIRKVDQLLLGKSLQEVAGQEVPRPRRNFTDLAKLSPPPQPGMDP-------  445
Sea bream            VSYIDENNIRLVKR-SQKKSLQDVKAASVQPRKEDTGHLRAVLSLLQSG----------  424
zebrafish            VSFVDEDNLRVVKK-SRKKRLQETKPLSLHQRKNELASMKTLLSVLQCGQSRSEPVQNGQ  439
                     **.:.*:. :  ::     .                .
```

Figure 2I

```
African clawed frog  ----------------ENEMR-LIKGRS--------------AMLPPAWCKCNKCINTTHLE------EQLCCRL 468
Western clawed frog  ----------------QTEMR-LIKGSS--------------TTLPPAWCKCNKCIDVTQPE------EQLCCRL 471
Chicken              -------------HGAAQSELRPLTQSSS--------------STNCPKWCCCGRCQVAQKHH------EQLCCRK 467
Rat                  -------------IPGQPEEMQLLQIEAVP------RSRDSPDWCQCGNCLPSQLPENRRALEELCCRR 498
human                -------------IPGQPEEIQLLRKEATP------RSRDSPVWCQCGSCLPSQLPESHRCLEELCCRK 501
dog                  -------------IPGQSEEMQLLSEEVTP------RSSNSPDWCQCGHCLPSQLPESQRCLEELCCRK 502
mouse                -------------TPGQSEEIQLLHEEVAP------KSGDSPSWCQCGNCLPSRLPEQRRALEELCCRR 503
chimpanzee           -------------IPGQPEEIQLLRKEATP------RSRDSPVWCQCGSCLPSQLPESHRCLEELCCRK 501
Macaque              -------------IPGQPGEMQPLREEATP------RSRDSPVWCQCGSCLPSQLPKSHRCLEELCCRK 501
Marmoset             -------------TPGQPEEMQLLREETTP------RPRDSPVWCQCGSCLPSQLPESHRCLEELCCRK 501
Panda                -------------IPGQPEEMQLFSEEVTP------RSSNSPDWCQCGHCLPSQLPESHRCLEELCCRK 501
horse                -------------TPGQPEDIQLLSEEVTP------RHKDSPHWCQCGNCLPSQLPESHRCLEELCCRK 501
cattle               -------------IPGQPEEIQLLSEEVHL------KSRDCPDWCQCGNCLPSQLPENQRCLEELCCRK 501
rabbit               -------------TPGQAEEMQPLSEGETA------RSRGCPDWCQCGNCLPSQLPASHRCLEELCCRR 501
Guinea pig           -------------APTQLEEMQPLRRPDTS------ASGDSPEWCQCGSCRPSQLPKDSRCLEELCCRR 500
Opossum              -------------SPAGPEEMQLLKDRPSP------PSQGKLKWCCCGHCRPSQLPEGTRCLEELCCRR 495
Sea bream            -------------VGANHDAQPPHEHKPDP------KQKPCRPAWCKCDHCTPSSVPQ------EELCCRQ 470
zebrafish            SGGLIVDENLSSRHNGRQNPDTPLLETTQSSSPTWCQCGSCRPAETLQ-------EQLCCRL 494
                                                                              **  *  *    **:***
```

Figure 2J

```
African clawed frog   EEGECITDTKMFNSLVLNRESLEYAFQYDNPLS--KTPISKEHLRYYAKQKYVEWRFGCR  526
Western clawed frog   GQGQCITDTEMFKYLVLNKEALEYAFQYDNPLS--KTPES-EDLKCYAKQKYIEWRFGCR  528
Chicken               KEGQCITTTYWFAQLVLSRDTLNKALLYEDPFLDLTGHSSNSQLRRIAYKQYIHWRFGS-  526
Rat                   KPGGQCITTSELFSKIVLSREALQLLLYQEPLLALEGEAINSKLRHCAYRSYATWRFVS-  557
human                 KPGACITTSELFRKLVLSRHVLQFLLLYQEPLLALDVDSTNSRLRHCAYRCYATWRFGS-  560
dog                   KAGACITTSEPFRKLILSRQVLQFLLLYQEPLLVLDENSN-SRLRHCAYRCYTTWRFGS-  560
mouse                 KPGRCITTSKLFHKLVLSRDTLQLLLYQDPLLVLGEEATNSRLRHRAYRCYATWRFGS-  562
chimpanzee            KPGACITTSELFRKIVLSRHVLQFLLLYQEPLLALDVDSTNSRLRHCAYRCYATWRFGS-  560
Macaque               KPGACITTSELFRKLVLSRHVLQFLLLYQEPLLALDVDSTNSRLRHCAYRCYATWRFGS-  560
Marmoset              KPGACITTSELFRKLVLSRHILQFLLLYQDPLLALDVDSTNSQLRHCAYRCYATWRFGS-  560
Panda                 KAGACITTSEPFRKLVLSRQVLQFLLLYQEPLLVLDGNSS-SRLRHCAYRCYTTWRFGS-  559
horse                 KMGACITTSEPFRKLVLSRRVLQFLLLYREPLLVLDADSTNSQLRHCAYRCYATWRFGS-  560
cattle                KPGACITTSELFRDIVLSRRALQFLLQYQEPLLVLDADSANSRLRHCAYRSYTAWRFGS-  560
rabbit                KPGACVTTSQLFGKLVLSKPTLQFLLLYQEPLLALDAEATTSQLRHCAYRCYIAWRFGS-  560
Guinea pig            GPGPCITTSELFGDIVLSRPALRQLLLYQEPLLVLDGEATNSGLRHCAYRCYTTWRFGA-  559
Opossum               KGGPCITTSALFEELVLSRATLRFILLYQEPLLEMDAATLNNRLRRCAYERYIDWRFGS-  554
Sea bream             SAGPCITTSSPLFGQLVLSHSLLEAVLLYRDPLSSLADRGQAASLRHCAYRQYISWRFG-V  529
zebrafish             KKGRCITTSSPIFSSLIVSRSVLENALFFVDPLAELHE---ESQLRHGAYAQFIRWRFGDS  551
                       *  *::*  ::    *       ::     ::              * *     ***
```

Figure 2K

```
African clawed frog    KYMLNFAVIPNCCKTAIETCNLQTEGP------------------   553
Western clawed frog    RYMLDFAVIPSCCKNAIETCNLQTQHPSGALYLPPTHGMC------   568
Chicken                FELEDRAIIPSCCRRLIRSTYPKENGNYTGFNLE-------------   560
Rat                    QDMADFAILPSCCRWKIRKEFPKTQGQYSGFKYPY------------   592
human                  QDMADFAILPSCCRWRIRKEFPKSEGQYSGFKSPY------------   595
dog                    QDLADFAILPSCCRWRIRREFPKSEGQYSGFRSPY------------   595
mouse                  QDMADFAILPSCCRWRIRKEFPKTEGQYSGFKYPY------------   597
chimpanzee             QDMADFAILPSCCRWRIRKEFPKSEGQYSGFKSPY------------   595
Macaque                QDMADFAILPSCCRWRIRKEFPKSEGQYSGFKSPY------------   595
Marmoset               QDMADFAILPSCCRWRIRREFPKSQGQYSGFKSPY------------   595
Panda                  PDLADFAILPSCCRWRIRREFPKSEGQYTGFQSPY------------   594
horse                  QDLADFAILPSCCRWRIRREFPRSEGQYGGFKSPY------------   595
cattle                 QDLADFAILPSCCRWRIRREFPKSEGQYSGFKSPY------------   595
rabbit                 QDLADFAILPSCCRWRIRKEFPKSEGPYSGFKSPY------------   595
Guinea pig             QDVADFGILPSCCRWRIRSEFPRSHGQYSGFRCPY------------   594
Opossum                EDMAGFAILPSCCRWMIRDHFPKQDGKYTGFKSPSPYTFLE------   595
Sea bream              PPNDTHPVIPSCCVWRVREEYPSPDGQYSGFRPVRIVSMQACTNGEL   576
zebrafish              TPRDALPVIPSCCIWRIRAEYPSPDGTYRGLRSFQVITSQTEVNR--   596
                         :**  :              .
```

COMPANION ANIMAL TREATMENTS

CROSS-REFERENCES TO RELATED APPLICATIONS

This application is a US national stage of PCT/AU2011/001166, filed Sep. 9, 2011, which is incorporated in its entirety, and which claims the benefit of AU2010904080, filed Sep. 10, 2010, and AU2011902626, filed Jul. 1, 2011.

INCORPORATION BY REFERENCE OF SEQUENCE LISTING

The sequence listing written in file 430898SEQLIST3.TXT is of 95 kilobytes and was created Jan. 18, 2015. The information contained in this filed is hereby incorporated by reference.

FIELD OF THE INVENTION

The invention relates to veterinary oncology, including treatment of cancer in companion animals.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

The incidence of cancer in companion animals, such as dogs and cats and the like is increasing, and cancer is now considered to be the leading cause of death in older animals. It is believed that the annual incidence rate for cancers in dogs is about 2 to 2.5% (about the same as humans) and about 1.5 to 2% for cats.

The cancers having the highest incidence in dogs are in the following order: lymphoma (about 20%); mast cell tumor (about 18%); soft tissue sarcoma (about 10%); hemangiosarcoma (about 10%); osteosarcoma (about 9%). The remaining segments typically include squamous cell carcinoma, mammary carcinoma, melanoma, histiocytoma and fibrosarcoma.

The cancers having the highest incidence in cats are in the following order: lymphoma (about 25%); mast cell tumor (about 22%—of cutaneous neoplasms); squamous cell carcinoma (>11% of cutaneous neoplasms); mammary carcinoma (about 10%); and the remaining segments include hemangiosarcoma, osteosarcoma, fibrosarcoma, sebaceous hyperplasia/adenoma.

Approaches to cancer treatment in veterinary oncology include surgery, radiation therapy, hyperthermia therapy, photodynamic therapy and chemotherapy. Gene therapy and immunotherapy have not been widely implemented.

Apart from Palladia (toceranib phosphate; Pfizer), no medicines have been given marketing approval for use as chemotherapeutics for cancer treatment in companion animals. This is mainly because of the high costs associated with obtaining marketing approval.

In most jurisdictions, veterinary oncologists have "off-label" drug use privileges. Off-label drug use means that the veterinary oncologist can use drugs approved for one species (including humans) freely in another species. With these privileges, a common practice has arisen in veterinary oncology whereby the oncologist tends to select those chemotherapeutics for use in cancer treatment of companion animals for which significant clinical experience has been obtained in human oncology.

Examples of chemotherapeutics and relevant indications currently used in veterinary oncology are shown in Table 1.

TABLE 1

| Chemotherapeutic | Type of cancer |
| --- | --- |
| Alkylating agents | |
| Cyclophosphamide (Cytoxan) | Lymphoma, mast cell tumors, mammary tumors, hemangiosarcomas |
| Ifosfamide (Ifex) | Chemoresistant lymphoma, soft tissue sarcoma |
| Chlorambucil (Leukeran) | Leukemias, mast cell tumors, lymphoma |
| Melphalan (Alkeran) | Multiple myeloma |
| Busulfan (Myeleran) | Leukemias |
| Procarbazine Hyd (Matulane) | Lymphoma |
| Plant alkaloids | |
| Vincristine (Oncovin) | Lymphoma, venereal tumors, mast cell tumors, sarcomas |
| Vinblastine | Lymphoma, mast cell tumors |
| Antimetabolites | |
| Methotrexate | Lymphoma, osteosarcoma |
| Cytosine arabinoside (Cytostar, Ara-C) | CNS lymphoma, leukemia |
| Fluorophyrimidines (Fluorouracil [5-FU]) | Skin tumors, mammary carcinoma, GI tumors |
| Hydroxyurea | Recurrent leukemias |
| Antitumor antibiotics | |
| Doxorubicin (hydroxydaunomycin) | Lymphoma, hemolymphatic malignancies, carcinomas and saracomas including osteosarcoma |
| Epirubicin (Pharmorubicin) | Lymphoma |
| Methoxymorpholinodoxorubicon | Chemoresistant lymphoma, sarcomas and carcinomas |
| Mitoxanthrone | Oral squamous cell carcinoma, lymphoma, sarcomas and carcinomas |
| Bleomycin | Squamous cell carcinoma |
| Actinomycin D | Lymphoma, sarcoma, carcinoma |
| Platinum compounds | |
| Cisplatin (Platinol) | Osteosarcoma, skin and nasal carcinomas |
| Carboplatin (Paraplatin) | Skin and nasal carcinomas |
| Lobaplatin | Osteosarcoma |
| Nitrosoureas | |
| Lomustine | Brain and CNS tumors, lymphomas, mast cell tumors |
| Carmustine | Brain tumors |
| Topoisomerase I inhibitors | |
| Camptothecins | Lymphoma |
| Hormones | |
| Prednisone | Lymphomas and mast cell tumors |
| Biologic Response Modifiers | |
| Peroxicam (Feldene) | Squamous cell carcinoma, mammary adenocarcinoma, transmissible venereal tumors |
| Muramyl dipeptide | Splenic hemangiosarcoma, osteosarcoma |
| Retinoids | |
| Etretinate (Tegison) | Cutaneous lymphoma, mycosis fungoides |
| Isotretinoin (Accutane) | |
| Other | |
| Paclitaxel (Taxol) | Mammary carcinomas, lymphomas |
| Darcarbazine | Recurrent lymphoma, melanoma, sarcomas |
| L-asparaginase (Elspar) | Lymphoid malignancies, mast cell tumors |

There are a number of problems and limitations concerning these chemotherapies. For example, as observed in human therapy, these compounds are associated with toxicities linked with the non specific action against dividing cells including bone marrow, gastrointestinal epithelia and hair follicles. Side effects include immunosuppression, anaemia, nausea and vomiting, delayed wound healing, reproductive failure and hair loss. Some specific organs may also be susceptible including heart, kidneys and CNS.

Also, the use of a single chemotherapeutic agent is rarely effective for curing cancer, as not all tumor cells will be effectively killed by a single agent. One reason for this is that as cancer cells develop, so too does the incidence of mutation that may result in resistance phenotypes. Therefore, in most situations it is necessary to develop a combination chemotherapy for the given clinical case.

There is a need for an alternative or improved treatment of cancers of companion animals, and especially those cancers having a higher incidence in companion animals.

There is also a need for an alternative or improved treatment of cancers in dogs.

There is a need for treatment of lymphoma, mast cell tumor, soft tissue sarcoma, hemangiosarcoma, osteosarcoma, squamous cell carcinoma, mammary carcinoma, melanoma, histiocytoma and fibrosarcoma in dogs.

There is also a need for an alternative or improved treatment of cancers in cats.

There is a need for treatment of lymphoma, mast cell tumor, squamous cell carcinoma, mammary carcinoma, hemangiosarcoma, osteosarcoma, fibrosarcoma, and sebaceous hyperplasia/adenoma in cats.

SUMMARY OF THE INVENTION

The invention seeks to address one or more of the above mentioned needs and in a first aspect provides a method for minimising the progression of cancer in a companion animal, the method including the steps of:
  providing a companion animal in which the progression of cancer is to be minimised; and
  providing in the animal a whole antibody, or a fragment thereof including a variable domain for binding to a non functional $P2X_7$ receptor that is expressed by the animal;
  thereby minimising the progression of cancer in the animal.

In a second aspect the invention provides a method for minimising the progression of cancer in a companion animal, the method including the steps of:
  providing a companion animal requiring treatment for cancer; and
  forming an immune response in the companion animal to a non-functional $P2X_7$ receptor;
  thereby minimising the progression of cancer in the companion animal.

In a third aspect the invention provides a method for minimising the progression of cancer in a companion animal, the method including the steps of
  providing a companion animal that has received a non self antigen binding site for treatment of the cancer;
  forming an immune response in the companion animal to a non-functional $P2X_7$ receptor;
  thereby minimising the progression of cancer in the companion animal.

In a further aspect of the invention there is provided a use of:
  a whole antibody, or a fragment thereof including a variable domain for binding to a non functional $P2X_7$ receptor; or
  a $P2X_7$ receptor, or a fragment of a $P2X_7$ receptor;
  in the manufacture of a medicament for treatment of cancer in a companion animal.

In yet a further aspect the invention provides a use of:
  a whole antibody, or a fragment thereof including a variable domain for binding to a non functional $P2X_7$ receptor; or
  a $P2X_7$ receptor, or a fragment of a $P2X_7$ receptor;
  for treatment of cancer in a companion animal.

In still further aspects the invention provides a kit or composition for use in the treatment of a cancer in a companion animal, the kit including:
  a whole antibody, or a fragment thereof including a variable domain for binding to a non functional $P2X_7$ receptor; or
  a $P2X_7$ receptor, or a fragment of a $P2X_7$ receptor;
  written instructions for use in a method or any one of the preceding claims.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 1. Amino acid sequence of $P2X_7$ receptor.
FIGS. 2A-K. Alignment of amino acid sequence of canine and human $P2X_7$ receptors.

DETAILED DESCRIPTION OF THE EMBODIMENTS

Figure 3:
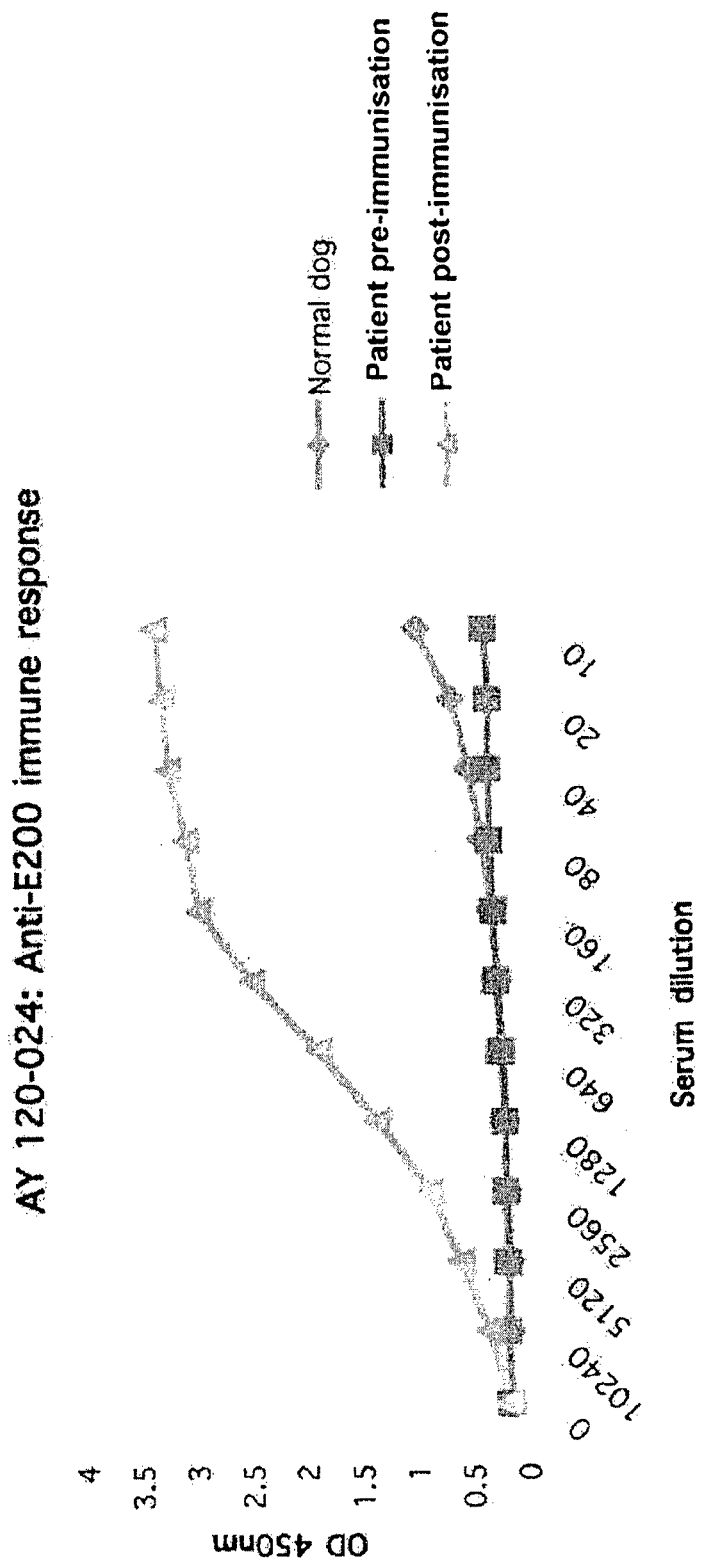
FIG. 3. Anti E200 antibody response detected by ELISA.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the animal features mentioned or evident from the text or drawings. All of these different combinations constitute various alternative aspects of the invention.

All of the patents and publications referred to herein are incorporated by reference in their entirety.

A Definitions

For purposes of interpreting this specification, the following definitions will generally apply and whenever appropriate, terms used in the singular will also include the plural and vice versa. In the event that any definition set forth conflicts with any document incorporated herein by reference, the definition set forth below shall prevail.

As used herein, except where the context requires otherwise, the term "comprise" and variations of the term, such as "comprising", "comprises" and "comprised", are not intended to exclude further additives, components, integers or steps.

"Companion animal" generally refers to an animal that is a pet or "companion" of a person. Cats (Felines) and dogs (Canines) are examples.

"Purinergic receptor" generally refers to a receptor that uses a purine (such as ATP) as a ligand.

"$P2X_7$ receptor" generally refers to a purinergic receptor formed from three protein subunits or monomers, with at least one of the monomers having an amino acid sequence substantially as shown in FIG. 1, or a canine sequence substantially as shown in FIGS. 2A-K. To the extent that $P2X_7$ receptor is formed from three monomers, it is a "trimer" or "trimeric". "$P2X_7$ receptor" may be a functional or non-functional receptor as described below. "$P2X_7$ receptor" encompasses naturally occurring variants of $P2X_7$ receptor, e.g., wherein the $P2X_7$ monomers are splice variants, allelic variants and isoforms including naturally-occurring truncated or secreted forms of the monomers forming the $P2X_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence $P2X_7$ monomeric polypeptides disclosed herein are mature or full-length native sequence polypeptides comprising the full-length amino acids sequence shown in FIG. 1, or a canine sequence substantially as shown in FIGS. 2A-K. In certain embodiments the $P2X_7$ receptor may have an amino acid sequence that is modified, for example various of the amino acids in the sequence shown in FIG. 1 or a canine sequence substantially as shown in FIGS. 2A-K may be substituted, deleted, or a residue may be inserted.

"Functional $P2X_7$ receptor" generally refers to a form of the $P2X_7$ receptor having a binding site or cleft for binding to ATP. When bound to ATP, the receptor forms non-selective sodium/calcium channel that converts to a pore-like structure that enables the ingress of calcium ions into the cytosol, one consequence of which may be programmed cell death. In normal homeostasis, expression of functional $P2X_7$ receptors is generally limited to cells that undergo programmed cell death such as thymocytes, dendritic cells, lymphocytes, macrophages and monocytes. There may also be some expression of functional $P2X_7$ receptors on erythrocytes.

"Non-functional $P2X_7$ receptor" generally refers to a form of a $P2X_7$ receptor having a conformation whereby the receptor is unable to form an apoptotic pore. One example arises where one or more of the monomers has a cis isomerisation at Pro210 (according to SEQ ID No:1). The isomerisation may arise in human and non human mammalian monomers from any molecular event that leads to misfolding of the monomer, including for example, mutation of monomer primary sequence or abnormal post translational processing. One consequence of the isomerisation is that the receptor is unable to bind to ATP at one or more ATP binding sites on the trimer and thereby extend the opening of the channel. In particular, where one of the three monomers is incorrectly packed and as a consequence, two ATP binding sites are disrupted. In the circumstances, the receptor cannot form a pore and this limits, the extent to which calcium ions may enter the cytosol. Only partial channel activity is maintained. Non-functional $P2X_7$ receptors are expressed on a wide range of epithelial and haematopoietic cancers.

"E200 epitope" generally refers to an epitope presented on a non-functional $P2X_7$ receptor. In humans the sequence is GHNYTTRNILPGLNITC (SEQ ID NO:3). In canines the sequence is GHNYTTRNILPDINITC (SEQ ID NO:4).

"E300 epitope" generally refers to an epitope presented on a non-functional $P2X_7$ receptor. In humans and canines the sequence is identical, namely: KYYKENNVEKRTLIKVF (SEQ ID NO:50).

"Composite epitope" generally refers to an epitope that is formed from the juxtaposition of the E200 and E300 epitopes. The point of difference in E200 as between canines and humans is not contained in the canine composite epitope, meaning that the canine and human composite epitopes are identical. While the feline $P2X_7$ receptor sequence has not been characterised, the serological data herein demonstrates that the feline composite epitope is identical or substantially the same as the canine and human composite epitope.

"Antibodies" or "immunoglobulins" or "Igs" are gamma globulin proteins that are found in blood, or other bodily fluids of verterbrates that function in the immune system to bind antigen, hence identifying and/or neutralizing foreign objects.

Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intrachain disulfide bridges.

H and L chains define specific Ig domains. More particularly, each H chain has at the N-terminus, a variable domain ($V_H$) followed by three constant domains ($C_H$) for each of the α and γ chains and four $C_H$ domains for u and c isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$).

Antibodies can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The L chain from any vertebrate species can be assigned to one of two clearly distinct types, called kappa and lambda, based on the amino acid sequences of their constant domains.

The constant domain includes the Fc portion which comprises the carboxy-terminal portions of both H chains held together by disulfides. The effector functions of antibodies such as ADCC are determined by sequences in the Fc region, which region is also the part recognized by Fc receptors (FcR) found on certain types of cells.

The pairing of a $V_H$ and $V_L$ together forms a "variable region" or "variable domain" including the amino-terminal domains of the heavy or light chain of the antibody. The variable domain of the heavy chain may be referred to as "$V_H$." The variable domain of the light chain may be referred to as "$V_L$." The V domain contains an "antigen binding site" which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each generally 9-12 amino acids long. The FRs largely adopt a β-sheet configuration and the hypervariable regions form loops connecting, and in some cases forming part of, the β-sheet structure.

"Hypervariable region" refers to the regions of an antibody variable domain which are hypervariable in sequence and/or form structurally defined loops. Generally, antibodies comprise six hypervariable regions; three in the $V_H$ (H1, H2, H3), and three in the $V_L$ (L1, L2, L3).

"Framework" or "FR" residues are those variable domain residues other than the hypervariable region residues herein defined.

"A peptide for forming an antigen binding site" generally refers to a peptide that may form a conformation that confers the specificity of an antibody for antigen. Examples include whole antibody or whole antibody related structures, whole antibody fragments including a variable domain, variable domains and fragments thereof, including light and heavy chains, or fragments of light and heavy chains that include some but not all of hypervariable regions or constant regions.

An "antigen binding site" generally refers to a molecule that includes at least the hypervariable and framework regions that are required for imparting antigen binding function to a V domain. An antigen binding site may be in the form of an antibody or an antibody fragment, (such as a dAb, Fab, Fd, Fv, F(ab')$_2$ or scFv) in a method described herein.

An "intact" or "whole" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof.

"whole antibody fragments including a variable domain" include Fab, Fab', F(ab')$_2$, and Fv fragments; diabodies; linear antibodies, single-chain antibody molecules; and multispecific antibodies formed from antibody fragments.

The "Fab fragment" consists of an entire L chain along with the variable region domain of the H chain ($V_H$), and the first constant domain of one heavy chain ($C_H1$). Each Fab fragment is monovalent with respect to antigen binding, i.e., it has a single antigen-binding site.

A "Fab' fragment" differs from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group.

A "F(ab)$_2$ fragment" roughly corresponds to two disulfide linked Fab fragments having divalent antigen-binding activity and is still capable of cross-linking antigen.

An "Fv" is the minimum antibody fragment which contains a complete antigen-recognition and binding site. This fragment consists of a dimer of one heavy and one light chain variable region domain in tight, non-covalent association.

In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the $V_H$ and $V_L$ antibody domains connected to form a single polypeptide chain. Preferably, the scFv polypeptide further comprises a polypeptide linker between the $V_H$ and $V_L$ domains which enables the scFv to form the desired structure for antigen binding.

A "single variable domain" is half of an Fv (comprising only three CDRs specific for an antigen) that has the ability to recognize and bind antigen, although at a lower affinity than the entire binding site "Diabodies" refers to antibody fragments with two antigen-binding sites, which fragments comprise a heavy-chain variable domain ($V_H$) connected to a light-chain variable domain ($V_L$) in the same polypeptide chain ($V_H$-$V_L$). The small antibody fragments are prepared by constructing sFv fragments (see preceding paragraph) with short linkers (about 5-10 residues) between the $V_H$ and $V_L$ domains such that interchain but not intra-chain pairing of the V domains is achieved, resulting in a bivalent fragment, i.e., fragment having two antigen-binding sites.

Diabodies may be bivalent or bispecific. Bispecific diabodies are heterodimers of two "crossover" sFv fragments in which the $V_H$ and $V_L$ domains of the two antibodies are present on different polypeptide chains. Triabodies and tetrabodies are also generally known in the art.

An "isolated antibody" is one, which has been identified and separated and/or recovered from a component of its pre-existing environment. Contaminant components are materials that would interfere with therapeutic uses for the antibody, and may include enzymes, hormones, and other proteinaceous or nonproteinaceous solutes.

"Monoclonal antibody" refers to an antibody obtained from a population of substantially homogeneous antibodies, i.e., the animal antibodies comprising the population are identical except for possible naturally occurring mutations that may be present in minor amounts. Monoclonal antibodies are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The "monoclonal antibodies" may also be isolated from phage antibody libraries using the techniques.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

The term "anti-P2X$_7$ receptor antibody" or "an antibody that binds to P2X$_7$ receptor" refers to an antibody that is capable of binding P2X$_7$ receptor with sufficient affinity such that the antibody is useful as a diagnostic and/or therapeutic agent in targeting P2X$_7$ receptor, typically non-functional P2X$_7$ receptor. Preferably, the extent of binding of an P2X$_7$ receptor antibody to an unrelated, P2X$_7$ receptor protein is less than about 10% of the binding of the antibody to P2X$_7$ receptor as measured, e.g., by a radioimmunoassay (RIA). In certain embodiments, an antibody that binds to P2X$_7$ receptor has a dissociation constant (Kd) of <1 μM, <100 nM, <10 nM, <1 nM, or <0.1 nM. An anti non-functional P2X$_7$ receptor antibody is generally one having some or all of these serological characteristics and that binds to non-functional P2X$_7$ receptors but not to functional P2X$_7$ receptors.

An "affinity matured" antibody is one with one or more alterations in one or more hypervariable region thereof, which result in an improvement in the affinity of the antibody for antigen, compared to a parent antibody, which does not possess those alteration(s). Preferred affinity matured antibodies will have nanomolar or even picomolar affinities for the target antigen. Affinity matured antibodies are produced by procedures known in the art.

A "blocking" antibody" or an "antagonist" antibody is one, which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

'Treatment' generally refers to both therapeutic treatment and prophylactic or preventative measures.

Animals requiring treatment include those already having a benign, pre-cancerous, or non-metastatic tumor as well as those in which the occurrence or recurrence of cancer is to be prevented.

The objective or outcome of treatment may be to reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder.

Efficacy of treatment can be measured by assessing the duration of survival, time to disease progression, the response rates (RR), duration of response, and/or quality of life.

In one embodiment, the method is particularly useful for extending time to disease progression.

In one embodiment, the method is particularly useful for extending survival of the animal, including overall survival as well as progression free survival.

In one embodiment, the method is particularly useful for providing a complete response to therapy whereby all signs of cancer in response to treatment have disappeared. This does not always mean the cancer has been cured.

In one embodiment, the method is particularly useful for providing a partial response to therapy whereby there has been a decrease in the size of one or more tumors or lesions, or in the extent of cancer in the body, in response to treatment.

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

"A condition or symptom associated" [with the cancer] may be any pathology that arises as a consequence of, preceding, or proceeding from, the cancer. For example, where the cancer is a skin cancer, the condition or relevant symptom may be microbial infection. Where the cancer is a secondary tumor, the condition or symptom may relate to organ dysfunction of the relevant organ having tumor metastases. In one embodiment, the methods of treatment described herein are for the minimisation or treatment of a condition or symptom in an animal that is associated with a cancer in the animal.

A "non self" molecule, such as a "non self" antigen binding site, or "non self" antibody generally refers to a molecule that has been produced outside of, or exogenous to, a body in which the molecule is to be provided, for example, for treatment. As an example, synthetic or recombinant molecules are "non self". Further, a molecule that is generated in one animal and administered to another animal for treatment is "non self". "Non self" antigen binding sites and antibodies may be used in accordance with the invention for adoptive transfer of immunity, for example, as occurs in antibody infusion. In contrast, a molecule that is generated inside an animal that is to be treated with that molecule, is generally a "self" or "endogenous" molecule. One example of a "self" molecule is an antigen binding site or antibody that is generated, or arises from an adaptive immune response to immunogen.

"level of non self antigen binding sites in circulation" in the animal generally refers to the concentration of antigen binding site in a body fluid, preferably peripheral blood.

a "substantially undetectable level of non self antigen binding sites in circulation" generally refers to a concentration of exogenous antigen binding sites (i.e. those that have been administered by adoptive transfer) that is at least half of the concentration of the antigen binding sites in circulation at the time of administration of the antigen binding sites, preferably 25%, or 10%, or 5% or 1% of said concentration, or otherwise less than 0.001 mg/kg of the animal. The phrase may also refer to a circumstance where antigen binding sites that have been given for the purpose of cancer immunotherapy cannot be detected at all.

a cancer that is "substantially undetectable" generally refers to a circumstance where therapy has depleted the size, volume or other physical measure of a cancer so that using relevant standard detection techniques such as in vivo imaging, the cancer, as a consequence of the therapy, is not clearly detectable. The phrase also refers to the circumstance where the cancer cannot be detected at all.

"forming an immune response" generally refers to invoking or inducing antigen specific immunity via the adaptive immune system. As is generally understood in the art, induction of antigen specific immunity is distinguished from adoptive transfer of immunity, standard cancer immunotherapy by administration of exogenous or non self antibody being one example of the latter.

B. Cancer Immunotherapy by Antibody Infusion

While the tissue expression profile of non functional P2X$_7$ receptors in normal, pre-neoplastic and neoplastic human tissues was understood at the time of the invention, very little was known regarding the tissue expression of non functional P2X$_7$ receptors in non human animals, especially companion animals such as cats and dogs.

In particular, it was not known whether the trimeric non functional receptor is expressed on living tissue in companion animals and in particular in which tissues. Further, it was not known whether expression would be found on cancer tissues and if so to what extent expression would be limited to cancer tissues. Accordingly it was not known whether certain companion animal cancers express non functional P2X$_7$ receptor, nor whether treatment with antibodies would have significant toxicity for normal cells.

Further, it was not known whether the cancer-specific epitopes observed in humans on living cancer tissue are present on cancer tissue in companion animals. At the time of the invention, this was directly relevant to the question of how to generate anti-cancer antibodies in companion animals. In particular, the cat P2X$_7$ receptor sequence was not known at all.

The dog P2X$_7$ sequence was known to be significantly different from the human P2X$_7$ receptor at the region of the dog sequence corresponding with E200 in the human, where immediately carboxyl to the key proline-210 (known in the human to give rise to non functionality of the human receptor), the dog sequence was known to have a non conservative substitution of negatively charged aspartate for neutral glycine as in the human. Further, of the other amino acid differences as between dog and human, at least about 55% of these were known to be non conservative substitutions, and one insertion not found in human. See in particular FIG. 2.

In summary of the above, at the time of the invention it was not known whether non functional P2X$_7$ receptors existed in companion animals including dogs and cats and therefore not known whether P2X$_7$ receptors could be used as a biomarker for treatment of cancer in companion animals as it has been used for humans.

As described herein, the inventors have shown that sheep antibodies raised: against an immunisation with a peptide having the E200 epitope are highly effective for treatment of a wide variety of cancers having a higher incidence in companion animals and with minimal side effects or toxicity. From this the inventors have recognised that certain live cancer cells in dogs and cats express non functional P2X$_7$ receptors. Given minimal toxicity, the expression of these, receptors appears to be limited to pre neoplastic or neoplastic tissues. Further, and in spite of differences, for example as between the dog and human P2X$_7$ sequences, these companion animal receptors seem to have an extracellular conformation much like that on which the human E200 epitope has been found.

Further, and surprisingly, the inventors have recognised that xenogeneic antibodies raised against xenogeneic P2X$_7$ immunogen are highly effective for treating cancer in companion animals including cats and dogs.

Thus, in a first aspect the invention provides a method for minimising the progression of cancer in a companion animal, the method including the steps of:
providing a companion animal in which the progression of cancer is to be minimised; and
providing in the animal a whole antibody, or a fragment thereof including a variable domain for binding to a non functional P2X$_7$ receptor that is expressed by the animal;
thereby minimising the progression of cancer in the animal.

In a further aspect the invention provides a use of a whole antibody, or a fragment thereof including a variable domain for binding to a non functional P2X$_7$ receptor in the manufacture of a medicament for treatment of cancer in a companion animal.

In yet a further aspect the invention provides a use of a whole antibody, or a fragment thereof including a variable domain for binding to a non functional P2X$_7$ receptor for treatment of cancer in a companion animal.

An animal to be treated in accordance with the methods of the first aspect of the invention may be one that has received, or is to receive any one of the therapeutic antibodies indicated for oncology.

In one embodiment of the first aspect, the antigen binding site of an antibody may be one that discriminates between functional and non-functional P2X$_7$ receptors, so as to bind to non-functional receptors, but not to functional receptors. Examples of these antigen binding sites are those that bind to the E200 epitope, E300 epitope or composite epitope as for example in PCT/AU2002/000061, PCT/AU2002/001204, PCT/AU2007/001540, PCT/AU2007/001541, PCT/AU2008/001364, PCT/AU2008/001365, PCT/AU2009/000869 and PCT/AU2010/001070, all of which are incorporated by reference.

The antigen binding site may take the form of a whole antibody, or a whole antibody fragment such as a Fab, a Fab', a F(ab')$_2$, and Fv, a single chain Fv, or a single variable domain.

The antigen binding site may be syngeneic, allogeneic or xenogeneic with respect to the companion animal that is to receive it for treatment of cancer.

Typically the antigen binding site is non self or exogenous meaning that it has been found or isolated outside of the animal who is treated according to the methods of the invention.

The antigen binding site may be affinity matured.

The antigen binding site may have multiple specificities or valencies.

The antigen binding site may be adapted so as to be suited to administration by a selected method.

The antibody may be a whole antibody of any isotype. The antibody may be one obtained from monoclonal or polyclonal antisera. The antibody may be produced by hybridoma, or by recombinant expression, or may be obtained from serum for example as obtainable from a mammal, particularly a human or mouse. The antibody may also be obtained from an avian.

The antibody may be chimeric, i.e. one containing human variable domains and non human constant domains. Alternatively, it may be humanized, i.e. one formed by grafting non human CDRs onto a human antibody framework. Still further, the antibody may be fully human.

The antibody may be modified with respect to effector function, so as to enhance, e.g., the effectiveness of the antibody in treating cancer.

Where the antibody is an antibody fragment, the antibody fragment is selected from the group consisting of a dAb, Fab, Fd, Fv, F(ab')$_2$, scFv and CDR.

Dosage amount, dosage frequency, routes of administration etc are described in detail below.

Methods of preparing and administering antibodies to an animal in need thereof are well known to, or are readily determined by those skilled in the art. The route of administration may be, for example, oral, parenteral (e.g. intravenous, intraarterial, intraperitoneal, intramuscular, subcutaneous, intradermal, rectal or vaginal), by inhalation or topical. One form for administration would be a solution for injection, in particular for intravenous or intraarterial injection or drip, comprising a buffer (e.g. acetate, phosphate or citrate buffer), a surfactant (e.g. polysorbate), optionally a stabilizer agent (e.g. albumin). In other methods antibodies can be delivered directly to the site of disease thereby increasing the exposure of the diseased cell or tissue to the antibody.

Preparations for parenteral administration includes sterile aqueous (aqueous carriers include water, alcoholic/aqueous solutions, emulsions or suspensions, including saline and buffered media) or non-aqueous (non-aqueous solvents are propylene glycol, polyethylene glycol, vegetable oils such as olive oil, and injectable organic esters such as ethyl oleate) solutions, suspensions, and emulsions. Pharmaceutically acceptable carriers include 0.01-0.1M and preferably 0.05M phosphate buffer or 0.9% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions, in such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminium monostearate and gelatin.

In any case, sterile injectable solutions can be prepared by incorporating an active compound (e.g., antigen binding site) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed disorders.

Effective doses of the compositions of the present invention, for treatment of disorders as described herein vary depending upon many different factors, including means of administration, target site, physiological state of the patient, whether the patient is human or an animal, other medications administered, and whether treatment is prophylactic or therapeutic. Treatment dosages may be titrated using routine methods known to those of skill in the art to optimize safety and efficacy.

For treatment of certain disorders with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen binding sites with different binding specificities are administered simultaneously, in which case the dosage of each antigen binding sites administered falls within the ranges indicated.

The antibody for binding to a non-functional $P2X_7$ receptor expressed on a cell can be administered on multiple occasions. Intervals between single dosages can be weekly, monthly or yearly. Intervals can also be irregular as indicated by measuring blood levels of target polypeptide or target molecule in the patient. In some methods, dosage is adjusted to achieve a plasma polypeptide concentration of 1-1000 ug/mL and in some methods 25-300 ug/mL. Alternatively, the antibody can be administered as a sustained release formulation, in which case less frequent administration is required. Dosage and frequency vary depending on the half-life of the antibody in the patient. The half-life of an antibody can also be prolonged via fusion to a stable polypeptide or moiety, e.g., albumin or PEG. In general, humanized antibodies show the longest half-life, followed by chimeric antibodies and nonhuman antibodies. In one embodiment, the antibody can be administered in unconjugated form. In another embodiment the antibody can be administered multiple times in conjugated form. In certain therapeutic applications, a relatively high dosage (e.g., up to 400 mg/kg of anti $P2X_7$ binding molecule, e.g., antibody per dose), at relatively short intervals is sometimes required until progression of the disease is reduced or terminated, and preferably until the patient shows partial or complete amelioration of symptoms of disease. The amounts can be several logs lower (i.e. 2 to 3 logs lower) where the antibody is conjugated to a radioisotope or cytotoxic drug.

Therapeutic agents can be administered by parenteral, topical, intravenous, oral, subcutaneous, intraarterial, intracranial, intraperitoneal, intranasal or intramuscular means for prophylactic and/or therapeutic treatment, in some methods, agents are injected directly into a particular tissue where non-functional $P2X_7$ receptor cells have accumulated, for example intracranial injection. Intramuscular injection or intravenous infusion are preferred for administration of antibody.

An antibody can optionally be administered in combination with other agents that are effective in treating the disorder or condition in need of treatment (e.g., prophylactic or therapeutic). Examples are agents commonly used for chemotherapy or radiotherapy in oncology. Additionally or alternatively, the antibody or agent may be administered before, during or after surgical intervention for resection or removal of tumor or tissue.

In accordance with the first aspect of the invention, in one embodiment, the method may be for treatment of cancer, especially for a therapeutic treatment of cancer.

In one embodiment, the objective or outcome of treatment is one or more of:
- to reduce the number of cancer cells;
- reduce the primary tumor size;
- inhibit (i.e., slow to some extent and preferably stop) cancer cell infiltration into peripheral organs;
- inhibit (i.e., slow to some extent and preferably stop) tumor metastasis;
- inhibit, to some extent, tumor growth;
- relieve to some extent one or more of the symptoms associated with the disorder.

In one embodiment, the method of the first aspect of the invention is for extending time to disease progression.

In one embodiment, the method of the first aspect is for extending survival of the animal, including overall survival as well as progression free survival.

In one embodiment, the method of the first aspect is for providing a complete response to therapy whereby all signs of cancer in response to treatment have disappeared.

In one embodiment, the method of the first aspect is for providing a partial response to therapy whereby there has been a decrease in the size of one or more tumors or lesions, or in the extent of cancer in the body, in response to treatment.

In one embodiment, animals requiring treatment include those having a benign, pre-cancerous, non-metastatic tumor.

In one embodiment, the cancer is pre-cancerous or pre-neoplastic.

In one embodiment, the cancer is a secondary cancer or metastases. The secondary cancer may be located in any organ or tissue, and particularly those organs or tissues having relatively higher hemodynamic pressures, such as lung, liver, kidney, pancreas, bowel and brain.

In one embodiment, the cancer may be substantially undetectable.

The companion animal may be a cat or dog. However, in light of the cross reactivity of antibodies raised against human protein for non primate receptors, the inventors have recognised that other non human mammals having equally distant phylogeny from humans would benefit from the invention. In one embodiment the companion animal is a high value animal or thoroughbred. One example is a horse.

Typically the cancer or pre-cancer requiring treatment is one that has a higher incidence in a given companion animal. For example, where the companion animal is a dog, the cancer may be lymphoma, mast cell tumor, soft tissue sarcoma, hemangiosarcoma, osteosarcoma, squamous cell carcinoma, mammary carcinoma, melanoma, histiocytoma, spindle cell carcinoma or fibrosarcoma.

Where the companion animal is a cat, the cancer may be a lymphoma, mast cell tumor, squamous cell carcinoma, mammary carcinoma, hemangiosarcoma, osteosarcoma, fibrosarcoma, or sebaceous hyperplasia/adenoma.

Other examples of cancer are described in Table I or include blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SGLG), non-small cell lung cancer (NSGLG), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

The dosage and frequency of administration can vary depending on whether the treatment is prophylactic or therapeutic. In prophylactic applications, compositions comprising antibodies or a cocktail thereof are administered to a patient not already in the disease state or in a pre-disease state to enhance the patient's resistance. Such an amount is defined to be a "prophylactic effective dose." In this use, the precise amounts again depend upon the animal's state of health and general immunity, but generally range from 0.1 to 25 mg per dose, especially 0.5 to 2.5 mg per dose. A relatively low dosage is administered at relatively infrequent intervals over a long period of time. Some animals continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the animal shows partial or complete amelioration of symptoms of disease.

In one embodiment, the antibody is provided in combination with another chemotherapeutic or anti-neoplastic compound indicated for use for the relevant cancer in the companion animal requiring treatment. Examples of these compounds and relevant indication are described in Table 1.

In another embodiment, the antibody is provided prior to, during, or post a clinical intervention selected from the group consisting of surgery, radiation therapy, hyperthermia therapy, photodynamic therapy, chemotherapy, gene therapy and immunotherapy.

C. Cancer Immunotherapy by Immunisation

In a second aspect the invention provides a method for minimising the progression of cancer in a companion animal, the method including the steps of:
providing a companion animal requiring treatment for cancer; and forming an immune response in the companion animal to a non-functional P2X$_7$ receptor;

thereby minimising the progression of cancer in the companion animal.

In a third aspect the invention provides a method for minimising the progression of cancer in a companion animal that has received a non self antigen binding site for treatment of the cancer, the method including the steps of:

providing a companion animal that has received a non self antigen binding site for treatment of the cancer;

forming an immune response in the companion animal to a non-functional P2X$_7$ receptor;

thereby minimising the progression of cancer in the companion animal.

In a further aspect, the invention provides a use of a non-functional P2X$_7$ receptor or fragment thereof in the manufacture of a medicament for treatment of a cancer in a companion animal, especially an animal such as a cat or dog that has received a non self antigen binding site for treatment of the cancer.

In yet a further aspect, the invention provides a use of a non-functional P2X$_7$ receptor or fragment thereof for treatment of a cancer in a companion animal, especially an animal such as a cat or dog that has received a non self antigen binding site for treatment of the cancer.

In another aspect, the invention provides a use of a P2X$_7$ receptor or fragment thereof in the manufacture of a medicament for the treatment of, or for the inhibition of progression of cancer in a companion animal that has received an anti-non-functional P2X$_7$ receptor antigen binding site for treatment of the cancer.

In one embodiment of the second and third aspects of the invention, the companion animal may not have detectable non self antigen binding sites in circulation at the time that the immune response is formed in the companion animal. For example, infused antibody may have been cleared from plasma at the time of immunisation. Further, the companion animal may not have detectable cancer at the time that the immune response is formed in the companion animal, for example, the cancer may have substantially diminished in size, mass or other physical measure as a consequence of administration of an antigen binding site to the companion animal at the time that the immune response is formed in the companion animal.

In accordance with the second and third aspects of the invention, the immune response may be formed by an immunogen. The immunogen may be provided in the form of a P2X$_7$ receptor, or a fragment of a P2X$_7$ receptor that is capable of inducing an immune response to a non-functional P2X$_7$ receptor in the companion animal. A non-functional P2X$_7$ receptor is defined as having at least one of the three ATP binding sites that are formed at the interface between adjacent correctly packed monomers that are unable to bind ATP. Such receptors are unable to extend the opening of the non-selective calcium channels to apoptotic pores. The immunogen may contain at least one sequence that is capable of being presented on a major histocompatibility complex class II molecule and/or is capable of interacting with a T or B-cell receptor or a B-cell membrane bound-immunoglobulin. Typically, the companion animal is a cat or dog, in which case the immunogen is provided in the form of a cat or dog P2X$_7$ receptor, or fragment thereof that is capable of inducing an immune response to a P2X$_7$ receptor. A dog P2X$_7$ receptor sequence is shown in FIG. 2 herein. Typically the immune response that is formed in the companion animal is specific for non-functional P2X$_7$ receptors, in which case antibodies or cellular components that are reactive with non-functional P2X$_7$ receptors (i.e. non ATP binding receptors), but not reactive with functional P2X$_7$ receptors (i.e. ATP binding receptors are) are formed in the companion animal.

In a preferred form of the second and third aspects of the invention, the immunogen is provided in an initial administration to the companion animal, thereby forming a response that includes IgM production. In a further preferred form, the immunogen, which has been provided in an initial administration to the companion animal, thereby forming a response that includes IgM production, is administered at a later time, in a further administration to the initial administration, thereby forming a response that includes IgG production. In this embodiment, typically the further administration of immunogen occurs when the level of IgM in circulation in the companion animal is substantially undetectable.

The immune response formed in accordance with the second and third aspects of the invention may be a humoral and/or cellular response. A humoral response may include the transformation of B-cells into plasma cells that secrete antibody, Th2 activation and cytokine production, germinal centre formation and isotype switching, affinity maturation of B-cells and/or memory cell generation. A cellular response may include activating antigen-specific cytotoxic T-lymphocytes, activating macrophages and natural killer cells and/or stimulating cells to secrete cytokines. The humoral and/or cellular response formed in the companion animal may treat or ameliorate a cancer in the companion animal, or minimise the progression of cancer in the companion animal.

In the above described embodiments of the second and third aspects of the invention, the antigen binding sites received by the companion animal may be reactive with any biomarker that is associated with cancer. Examples include antigen binding sites against P2X$_7$, especially, non-functional P2X$_7$, against VEGF, especially VEGF A, C or D, Her-2, CD20 or others. Typically the antigen binding sites received by the companion animal are reactive with P2X$_7$ receptor, especially a non-functional P2X$_7$ receptor.

In another embodiment of the second and third aspects of the invention, there is provided a composition for treating, or for inhibiting the progression of a cancer in a companion animal including a P2X$_7$ receptor or fragment thereof. Preferably the composition further includes a carrier, excipient or diluent. Preferably, the composition further includes an adjuvant. In a preferred form, the composition enables the formation of a primary immune response (including IgM production) upon initial administration of the immunogen to the companion animal, and a second immune response (including IgG production) upon administration of the immunogen further to the initial administration.

Without being bound by any theory or mode of action, it is believed that the above described embodiments relevant to the second and third aspects of the invention provide an alternative and/or improved treatment regime for the reason that endogenous immune components such as antibodies and antigen specific cells that arise from immunisation provide for a more prolonged and higher exposure of cell surface P2X$_7$ receptors after administration of antigen binding sites has been completed and the circulating level of non self anti-P2X$_7$ antigen binding sites becomes undetectable. Further, it is believed that P2X$_7$ receptor crowding, as arises when high concentrations of non self or exogenous antibodies are provided in a companion animal, minimises the level of specific antibody binding to the key P2X$_7$ epitopes that provide for an anti cancer immune response, thereby limiting the efficacy of immunotherapy. The inventors have found that immunisation of a companion animal at a time when the circulating level of non self antibodies becomes substantially undetectable avoids receptor crowding, and this improves the efficacy of immunotherapy, particularly at a time when cancer in the companion animal may be substantially undetectable.

In one embodiment of the second and third aspects of the invention, the animals selected for treatment have not been treated with antibody immunotherapy or other form of therapy. In another embodiment, the animals selected for treatment according to a method described above are those who have received, or who are continuing to receive antibody immunotherapy, for treatment of cancer. Antibody immunotherapy generally means the administration of exogenous, (otherwise known as or "non self") antibodies to an animal requiring treatment, as in the case of adoptive transfer of antibody. For example, the animal may have received any one of the therapeutic antibodies that have received regulatory approval for indications related to oncology. Avastin, Herceptin, Rituxan are examples. Typically the animal has received or is continuing to receive an anti $P2X_7$ receptor antibody. Examples of suitable anti-$P2X_7$ antibodies, their generation, manufacture, use and administration to a companion animal are described in the embodiments relevant to the first aspect of the invention.

Further, the animal selected for treatment according to the second and third aspects of the invention may or may not have detectable cancer at the time of treatment. Where the animal does not have detectable cancer, a primary or secondary humoral response is more easily detected because, with the cancer being present in substantially undetected amount, there is very little non-functional $P2X_7$ receptor available to remove IgM or IgG from body fluid.

The types of cancer which may be treated according to the second and third aspects of the invention and the desired treatment outcomes are those as described in the embodiments relevant to the first aspect of the invention.

The purpose of the treatment according to the second and third aspects of the invention is to at least minimise the progression of cancer by induction or formation of an immune response in the animal to a $P2X_7$ receptor. Therefore, the animal selected for treatment must be capable of generating an immune response sufficient for meeting this purpose. Generally the desired immune response includes a capacity to produce either or both of circulating IgM and IgG when the animal is challenged by cancer, as in recurrence of cancer.

Animals having a capacity to generate the immune response described herein may be selected or screened by a variety of methods well known in the art for detection of immunodeficiency. Typically, the animal selected for treatment will be one having at least one white blood cell component count within normal parameters. For example, a cat for inclusion is generally one having a white blood cell count of between 5.5 to $19.0\times10^9$/L, or a lymphocyte count of between 0.9 to $7.0\times10^9$/L. Neutrophil count may be between $2-13\times10^9$/L; monocyte count $<0.7\times10^9$/L, eosinophil less than about $1.1\times10^9$/L and basophil less than about $0.1\times10^9$/L. For example, a dog for inclusion is generally one having a white blood cell count of between 4.5 to $17.0\times10^9$/L, or a lymphocyte count of between 0:9 to $3.5\times10^9$/L. Neutrophil count may be between $3.5-12\times10^9$/L; monocyte count $<1.2\times10^9$/L, eosinophil less than about $1.5\times10^9$/L and basophil less than about $0.1\times10^9$/L.

It will be understood that in certain embodiments the cell count for any one of these blood cell components may fall outside these stated ranges, particularly in circumstances where the animal has a form of blood cancer, for example CML, CLL etc.

Generally an important factor is the lymphocyte count and/or monocyte count. In more detail, where either or both of these counts are significantly below the stated ranges for these components, the animal may be less likely to respond to administration of the immunogen.

Where the animal is continuing to receive antibody immunotherapy, in one embodiment of the second and third aspects of the invention, the antibody immunotherapy is allowed to continue to the desired clinical endpoint. Typically the desired clinical endpoint is a reduction of cancer to substantially undetectable levels. During, or at the completion of immunotherapy, the capacity of the animal to form, or generate an immune response to a $P2X_7$ receptor is then assessed. Where the assessment reveals that the animal is likely to benefit from immunisation with $P2X_7$ immunogen, the animal is then administered with immunogen.

In a preferred form of the second and third aspects of the invention, the level of non self or exogenous antigen binding sites in circulation in the animal arising from antibody immunotherapy is substantially undetectable at the time that the immune response is formed in the animal. Importantly, a key finding of the inventor is that efficacy of antibody treatment, particularly when cancer cells are in very low copy number, or otherwise substantially undetectable, decreases at higher circulating concentrations of antigen binding sites. This is believed to be a function of the low copy number of non-functional $P2X_7$ receptors on cancer cells relative to the high concentration of antigen binding sites that arise in standard antibody immunotherapy. Specifically, in the Examples herein, the inventor has found that as the circulatory level of antigen specific binding sites increase, and the number of cancer cells decrease, there is a much higher likelihood of crowding of the non-functional $P2X_7$ receptor by antigen binding sites that block antigen specific binding of the receptor. This blockage increases the likelihood that the intended cytotoxic, apoptotic or other effects of antigen specific binding by an antigen binding site will not be possible. One can determine the level of exogenous antigen binding sites in circulation by any standard serological technique capable of detecting antibody in fluid, one preferred example being ELISA using an antibody to capture antigen binding sites.

Further to the above, while not wanting to be bound by hypothesis, the inventors consider that administration of immunisation at a time where infused antibody is present increases the risk that the infused antibody could bind to the immunogen, resulting in immune complex formation and clearance, thereby avoiding antigen presentation and induction of antigen specific immunity. Therefore, in certain embodiments it is particularly useful to wait until the level of non self or exogenous antigen binding sites have been cleared from circulation before induction of the antigen specific immune response to immunogen.

The methods of the second and third aspects of the invention described herein require the formation of an immune response in an animal to be treated to a $P2X_7$ receptor, especially a non-functional $P2X_7$ receptor. Generally the immunogen, which is used for the purpose, is one which elicits an immune response to non-functional $P2X_7$ but not to functional $P2X_7$ receptors.

The inventors have found that the composite epitope exists in a wide range of species meaning (i) that antigen binding sites or antibodies could be raised in a wide range of animals for use in antibody infusion therapy and (ii) that a wide range of species of animals could be treated by the active immunisation therapy, according to the second and third aspects of the invention herein. The following table demonstrates the % identity as between the human composite epitope and the epitope in other species.

TABLE 2

Human E200/E300 Alignment to Other Species

| Species | DNA Database No. | E200/E300 Sequence | Percent Identity |
|---|---|---|---|
| Human | AB590390.1 | GHNYTTRNILPG-- (SEQ ID NO: 6) AKYYKENNVEK (SEQ ID NO: 7) | 100% |
| Chimp | XM_001163832.1 | GHNYTTRNILPG-- (SEQ ID NO: 6) AKYYKENNVEK (SEQ ID NO: 7) | 100% |
| Macaque | AB173225.1 | GHNYTTRNILPG-- (SEQ ID NO: 6) AKYYKENNVEK (SEQ ID NO: 7) | 100% |
| Orangutan | XM_002823877.1 | GHNYTTRNILPG-- (SEQ ID NO: 6) AKYYKENNVEK (SEQ ID NO: 7) | 100% |
| Marmoset | XM_002753098.1 | GHNYTTRNILPG-- (SEQ ID NO: 6) AKYYKENNVEK (SEQ ID NO: 7) | 100% |
| Rabbit | XM_002719745.1 | GHNYTTRNILPG-- (SEQ ID NO: 6) AKYYKENNVEK (SEQ ID NO: 7) | 100% |
| Horse | XM_001495572.1 | GHNYTTRNILPG-- (SEQ ID NO: 6) AKYYKENNVEK (SEQ ID NO: 7) | 100% |
| Wolf | NM_001113456.1 | GHNYTTRNILPG-- (SEQ ID NO: 6) AKYYKENNVEK (SEQ ID NO: 7) | 100% |
| Panda | XM_002913118.1 | GHNYTTRNILPG-- (SEQ ID NO: 6) AKYYKENNVEK (SEQ ID NO: 7) | 100% |
| Boar | AY691687.1 | GHNYTTRNILPG-- (SEQ ID NO: 6) AKYYKENNVEK (SEQ ID NO: 7) | 100% |
| Pig | CT737324.4 | GHNYTTRNILPG-- (SEQ ID NO: 6) AKYYKENNVEK (SEQ ID NO: 7) | 100% |
| Mouse | NM_001038845.2 | GHNYTTRNILPG-- (SEQ ID NO: 6) AKYYKENNVEK (SEQ ID NO: 7) | 100% |
| G. Pig | NM_001173107.1 | GHNYTTRNILPG-- (SEQ ID NO: 6) AKYYRENNVEK (SEQ ID NO: 27) | 96% (22/23) |
| Bovine | XM_591410.2 | GHNYTTRNILPG-- (SEQ ID NO: 6) AKYYKENNTEK (SEQ ID NO: 29) | 96% (22/23) |
| Rat | NM_019256.1 | GHNYTTRNILPG-- (SEQ ID NO: 6) AKYYKENGMEK (SEQ ID NO: 31) | 91% (21/23) |

The immunogen may include or consist of a peptide including a sequence of a P2X₇ receptor. The peptide may contain at least one sequence that is capable of being presented on a major histocompatibility complex class II molecule or, that is capable of interacting with a B-cell receptor or a B-cell membrane bound-immunoglobulin. Typically the peptide includes a sequence of a non human, preferably companion animal P2X₇ receptor or fragment thereof.

A range of peptide immunogens are known and discussed in PCT/AU2002/000061, PCT/AU2002/000061, PCT/AU2008/001364 and PCT/AU2009/000869, the contents of which are incorporated in entirety.

Exemplary peptides immunogens within these specifications which include epitopes for generating an immune response to a non-functional P2X₇ receptor are described below.

| PCT application | Peptide immunogen sequence |
|---|---|
| PCT/AU2002/000061, | GHNYTTRNILPGLNITC (SEQ ID NO: 3) |
| PCT/AU2008/001364 | KYYKENNVEKRTLIKVF (SEQ ID NO: 50) |
| PCT/AU2009/000869 | GHNYTTRNILPGAGAKYYKENNVEK (SEQ ID NO: 32) |

As discussed above, in one embodiment the peptide immunogen includes part or all of a canine or feline P2X₇ receptor sequence.

It will be understood that these are merely examples of possible immunogens useful for forming an immune response according to the second and third aspects of the invention. Further, the invention includes the use of other peptides as described in these applications useful for forming an immune response to non-functional P2X₇ receptors.

Typically the immunisation regime involves 2 or more immunisations. In a first immunisation, the objective may be to develop an IgM response to immunisation. A second immunisation may be to develop and IgG response. Further immunisations may be to boost the IgG response.

Where the immunogen is a peptide, the peptide may be provided in an amount of about 0.1 to 1 mg per administration, preferably about 0.25 to 0.75 mg, preferably about 0.5 mg in a large dog but half that in a small dog or cat.

A further administration of about 0.3 mg peptide may be applied as a boost in a large dog but half that in a small dog or a cat.

In one embodiment of the second and third aspects of the invention, a first immunisation is performed when the circulating level of antigen binding sites that had been administered for antibody immunotherapy is substantially undetectable. In other words, circulating antibody to the relevant cancer biomarker cannot be detected in peripheral blood. The level of IgM production is then monitored over the following weeks. At about 4 to 5 weeks after first immunisation, the level of IgM antibody is likely to have decreased to negligible circulating levels. At this point, a second immunisation is then performed and the level of IgG production is monitored over the following weeks. Further testing of immunity over the following months/years may be performed and boosting immunisations may be provided as required.

As discussed above, the immune response may target a biomarker that is different to the biomarker that has been targeted by antibody immunotherapy. For example, anti CD20 antibody may be used for antibody immunotherapy and a non-functional P2X₇ immunogen used for generating an immune response.

In another embodiment of the second and third aspects of the invention, a single biomarker is targeted by antibody immunotherapy and immunisation. For example, a monoclonal antibody directed to one epitope on a P2X₇ receptor (such as the E300 epitope) may be used for antibody immunotherapy, and an immunogen for forming an immune response that targets a different epitope (such as the E200 epitope) on P2X₇ may be used for immunisation.

A peptide immunogen for use in the second and third aspects of the invention herein may have a length of 6, 7, 8, 9, 10, 11, 12, 13, 14, 15, 16, 17, 18, 19, 20, 21, 22, 23, 24, 25 or 26 residues.

In one embodiment of the second and third aspects of the invention, the immunogen for forming an immune response according to a method of the invention is a peptide having a sequence of a P2X₇ receptor that may or may not have Pro210 in cis conformation.

The immunogen may be in the form of a P2X₇ extracellular domain or any one or more of the P2X₇ isoforms. The immunogen may be provided for administration in a soluble form or associated with a solid phase such as a cell membrane, bead, or other surface.

Methods for screening peptides that can be used as an immunogen to form an immune response according to the methods of the invention herein are disclosed herein. One example includes the use of erythrocytes in a rosetting assay. In this assay an antibody that binds to functional receptors is used as a positive control in which rossettes are observed. A test antibody is determined not to bind to functional receptors if it fails to form rossettes. It is determined to bind to non-functional receptors if it is observed to bind to a non-functional receptor-expressing cell line, including those discussed herein.

The peptides of the invention can be made by any number of techniques known in the art including solid phase synthesis and recombinant DNA technology.

As is known in the art, a Carrier is a substance that may be conjugated to a peptide epitope thereby enhancing immunogenicity. Some carriers do this by binding to multiple peptides so as to provide an antigen of increased molecular weight to the host in which the immune response is to be developed.

Preferred carriers include bacterial toxins or toxoids. Other suitable carriers include the *N. meningitides* outer membrane protein, albumin such as bovine serum albumin, synthetic peptides, heat shock proteins, KLH, Pertussis proteins, protein D from *H. influenza* and toxin A, B or C from *C. difficile*.

When the carrier is a bacterial toxin or toxoid, diphtheria or tetanus toxoids are preferred.

Preferably the carrier contains functional groups that can react with the peptide of the invention, or may be modified to be capable of reacting with the peptide.

The immunogen may be administered subcutaneously, intradermally and/or intramuscularly.

In a preferred form, the composition for forming an immune response to a P2X₇ receptor for use in the methods of the invention described herein includes an adjuvant or compound for potentiating an immune response.

A large number of adjuvants are known; See also Allison (1998, Dev. Biol. Stand., 92:3-11; incorporated herein by reference), Unkeless et al. (1998, Annu. Rev. Immunol., 6:251-281), and Phillips et al. (1992, Vaccine, 10:151-158).

Exemplary adjuvants that can be utilized in accordance with the invention include, but are not limited to, cytokines, aluminium salts (e.g., aluminium hydroxide, aluminium phosphate, etc.; Baylor et al., Vaccine, 20:S18, 2002), gel-type adjuvants (e.g., calcium phosphate, etc.); microbial adjuvants (e.g., immunomodulatory DNA sequences that include CpG motifs; endotoxins such as monophosphoryl lipid A (Ribi et al., 1986, Immunology and Immunopharmacology of bacterial endotoxins, Plenum Publ. Corp., NY, p 407, 1986); exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161), Q57, saponins (e.g., QS21, Ghochikyan et al., Vaccine, 24:2275, 2006), squalene, tetrachlorodecaoxide, CPG 7909 (Cooper et al., Vaccine, 22:3136, 2004), poly[di(carboxylatophenoxy)phosphazene] (PCCP; Payne et al., Vaccine, 16:92, 1998), interferon-γ (Cao et al., Vaccine, 10:238, 1992), block copolymer P1205 (CRL1005; Katz et al., Vaccine, 18:2177, 2000), interleukin-2 (IL-2; Mbwuike et al., Vaccine, 8:347, 1990), polymethyl methacrylate (PMMA; Kreuter et al., J. Pharm. ScL, 70:367, 1981), etc.

In one embodiment of the second and third aspects of the invention, a peptide immunogen containing a sequence of a $P2X_7$ receptor is provided on the surface of a bacteriophage for immunisation of an animal according to a method of the invention described herein.

In still further aspects, the invention provides a kit or composition for use in the treatment of a cancer in a companion animal, the kit including:
- a whole antibody, or a fragment thereof including a variable domain; or
- a $P2X_7$ receptor, or a fragment of a $P2X_7$ receptor;
- written instructions for use in a method described herein.

Preferably the antibody or fragment binds to a $P2X_7$ receptor, preferably a non functional $P2X_7$ receptor. More preferably, the antibody or fragment does not bind to functional $P2X_7$ receptor.

Preferably the written instructions are in the form of a label or package insert with instructions for use in a method described herein.

EXAMPLES

Example 1

Cat 1 (GB)

Extensive SCCs scalp and lips, area up to 4 cm$^2$ and full thickness of lip. SCC left lip had spread to angle of jaw under the fur prior to treatment. IHC on SCC left lip stained for nf-$P2X_7$ target receptor prior to treatment.
Partial efficacy with intratumoral (i.t.) injections
Target receptors widespread in affected tissue as revealed by IHC
Single infusion of cancer-specific therapeutic antibody targeting nf-$P2X_7$ receptors administered at fluid maintenance rate at dose of 3 mg/kg
Clear signs of tumour clearance by Day 4
By Day 14, majority of SCC left lip tumour eliminated, 2 weeks post treatment, after single dose IV at 3 mg/kg.
SCC clusters above left eye also clearing at 2 weeks post treatment, IV at 3 mg/kg. Fur regrowth over original lesion site now evident
Scalp SCCs and lip SCCs largely removed within 5 weeks after 3 IV doses although there are signs of new epithelial tissue being scratched by the patient. The central SCC lesion in midline of lower jaw that penetrated into the bone now has the appearance of white nodular scar tissue. The patient is untroubled by having the lesion site handled unlike the condition at the outset of treatment in which severe pain was evident.
After 6 monthly IV treatments the condition has resolved with even new bone growth revealed via X-ray in the inner mandible
Total accumulated dose to effect clinical clearances estimated to be 30-40 mg/kg due to loss of efficacy through appearance of anti-sheep antibodies over time Example 2

Cat 2 (AL)

SCC on nose prior to i.t. injection
Only 1× i.t. injection due to general anaesthetic causing cortical blindness lasting several hours as cat is 21 years of age
Followed up with topical anti-nf-$P2X_7$ IgG
5 days—SCC nose forming new tissue
19 days—SCC nose formed more new tissue Example 3

Cat 3 (PC)

Pancreatic cancer with metastases to liver and mesentery
Mesenteric metastases of order 1 cm not evident by ultrasound scan after 2 weekly i.v. infusions
Evidence of some tumour lysis (liquid) by ultrasound scan after 2 weekly i.v. infusions
After 4 weeks the liver secondary had shrunk from 5 to 2 cm diameter
After 4 weeks the 5-6 cm diameter pancreatic primary had approximately 80% of its mass liquefied
Euthanized after end of week 5 due to pancreatic tumour lysis/haemorrhaging into abdomen and at request of the owner Example 4

Cat 4 (FH)

SCC of nose extending from left nostril 2 cm to bridge of nose
Biopsy revealed extensive recurrent SCC following treatment by surgery late 2008
After single i.v. dose at 5 mg/kg tumour reduced in size on upper nasal surface with spongy consistency becoming firm
After second weekly infusion the lesion was no longer evident. A third infusion was applied and at the end of 2 weeks all clinical signs of the lesion were absent. A further infusion was applied to ensure elimination of residual preneoplastic cells that may have been present.
Clinically cleared at 21 days with an aggregate dose of 18 mg/kg No recurrence after 14 months so patient appears completely cured

Example 5

Cat 5 (CO)

History

Patient had a Bowen's-like lesion removed from left temporal region in 2008. It was noted in an examination in March 2009 that this lesion had reappeared and a new lesion had appeared on the opposite side. These were biopsied with the following results:

Diagnosis

Multicentric squamous cell carcinoma-in-situ with moderate to severe serocellular crusting, superficial dermal scarring and moderate perivascular eosinophilic dermatitis. Skin biopsies from left ear.

Moderate hyperplastic perivascular and interstitial eosinophilic dermatitis with moderate superficial dermal laminar fibroplasias. Biopsies from neck.

Multicentric squamous cell carcinoma in situ with moderate hyperpigmentation, moderate serocellular crusting and extensive dermal scarring in more cranial section. Biopsies from right ear.

Comments

The cat has multiple foci of neoplastic transformation of the epidermal and follicular tissue, consistent with a multicentric squamous cell carcinoma in situ or Bowen's-like disease. These lesions are similar to biopsies submitted in June 2008. There is no evidence of invasive squamous carcinoma in the sections examined.

SCC in situ (Bowen's)

No adverse reaction to 5 mg/kg infusion of sheep anti-nf-P2X$_7$ IgG

After 2 weeks the lesions had diminished noticeably but remained extensive so a second infusion was administered as a result of the initial improvement All extensive Bowen's lesions cleared following investigation by veterinary dermatologist who noted a deep SCC in the right ear canal was only apparent following the clearing of the superficial lesions and the associated infections. The patient had to be prevented from lacerating the new epithelium through scratching by attaching a restriction collar to allow the skin surface to heal.

Example 6

Dog 1 (CJ)

History of haemangiosarcoma on ventral abdomen in 30 kg dog. After multiple surgeries no longer surgical candidate as tumours so aggressive. Treated with intratumoral injection of nfP2X$_7$ IgG cut and 3 IV infusions of nfP2X$_7$ affinity purified antibody. IT injections of 6 mg antibody into cutaneous lesions 6 cm diameter showed 80% reductions in a week with tumour lysis evident as distinct serous discharge.

Treated for 4 weeks with i.t ×1 and i.v. ×3 doses at 2-3.4 mg/kg

Reduction of tumour size following treatment with sheep anti-nf-P2X$_7$ IgG

Euthanased on Mar. 21, 2010 due to tumour lysis/leakage syndrome of these large tumours (total mass 1-2 kg) and following owner's request

Example 7

Dog 2 (MO)

Transitional cell carcinoma (TCC) with malignant ascites found to be metastatic mesothelioma at post mortem pathology Treated for 2 weeks with i.v. ×3 doses at 1-2.7 mg/kg with chemotherapy Tumour reduced by 15% at week 2, although ascites remained Treatment withdrawn on week 3 at owner's request and against advice of vet

Example 8

Dog 3 (PI)

Mast Cell Lymphoma between middle two toes front right paw Start—appearance is hard and projects below foot pad causing discomfort. Surgery would require removal of front leg to maintain 3 cm margins Mast Cell Lymphoma Start—1 week post IV 5 mg/kg—volume reduced 40%

Mast Cell Lymphoma Start—2 weeks lesion now soft and greatly reduced in size with no projection below foot pad and no discomfort evident in dog. Solid core of lesion now confined to single toe with surrounding reactive cell sac fully pliable.

Metastatic lesion in subscapular lymph node undetectable by Week 2

Primary lesion remained largely unchanged in appearance for 3 months

Dog euthanized at owner's request as primary lesion became ulcerated under the paw Post mortem biopsies showed patient to free of all tumours, the primary lesion site was devoid of mast cells, containing reactive lymphocytes Lesions may have been cleared with aggregate dose of less than 30 mg/kg

Example 9

Dog 4 (BE)

Osteosarcoma upper left humerus diagnosed via CT scans after patient presented in extreme pain and lame, ready to be euthanized.

Weekly infusions at 10/mg/kg initiated. Within a week the patient re-engaged with owners and appeared largely pain free and wanting to go for walks.

CT scan and post treatment diagnostic tissue to be obtained under general anaesthetic at 9 weeks, thought to be the minimum time needed for bone regrowth to be readily detectable No sign of tumour cells in biopsy at Week 9 with patient appearing very well Patient euthanized at 5 months as a result of the left proximal humerus fracturing. Biopsy of the lesion site showed no evidence of residual osteosarcoma. A total remission seemed in evidence but the bone was left thin and brittle by the tumour.

In such cases an external splint should be applied to protect the bone while associated treatment to aid bone regrowth is undertaken.

Example 10

Dog 5 (WC)

Metastatic mast cell lymphoma (Grade 2) with high mitotic index (25). Multiple lesions >5 cm on ribs, shoulder and hind legs. Placed immediately on weekly IV infusions of 10 mg/kg.

Total lesion volume reduced by 75% at end of first week in line with expectation of rapid clearance as shown by PI.

Principal lesion still palpatable but further reduced at the end of week 2 following a second infusion Extensive analysis of lesion sites by ultrasound and cytology due at the end of three weeks following three infusions and a week to elicit a response Final needle aspirates of all lesion sites performed at 3 months and at 6 months. No evidence of any mast cells.

At 13 months patient is considered tumor free.

Example 11

Dog 6 (HL)

Patient presented with high grade metastatic mast cell tumor originating on leg with popliteal lymph node involvement.

Treatment by infusion at 10 mg/kg weekly for 6 weeks.

All swelling abolished by Week 3

Pathology at Week 6 showed no mast cells in tumor sites

Patient has had no recurrence in a year

Example 12

Antibody Manufacture

Sheep anti-$P2X_7$ antibodies 500 ug of conjugate (approximately 100 ug of $P2X_7$ epitope) was diluted in phosphate-buffered saline (PBS) to 0.8 mL and was emulsified with 1.2 mL of Freund's Complete adjuvant. Sheep were injected at multiple, sites both subcutaneously and intramuscularly with the antigen/adjuvant emulsion. Eight weeks later the sheep were again injected with the same amount of conjugate emulsified with Freund's Incomplete adjuvant at multiple sites. This was repeated 4 weeks later and the animals were bled from the jugular vein. The serum collected was tested for antibody specificity. The sheep were then routinely injected and bled at eight week intervals to provide a pool of serum containing the specific antibodies.

Other sheep were injected with the same dose of conjugated antigen similar to the schedule above but a different adjuvant was used. In these animals, 0.7 mL of the diluted antigen was mixed with 0.1 mL of a Quill A/DEAE Dextran solution (2.5 mg Quill A+25 mg DEAE Dextran per mL of PBS) and 1.2 mL of ISA 50V Montanide. The emulsion was injected at multiple sites both subcutaneously and intramuscularly. The antibodies produced using this adjuvant produced the same specificities as those produced using Freund's adjuvant.

Antibodies were raised in rabbits using the same two adjuvants as with the sheep and the same injection schedules, the only difference being that 300 ug amounts of the conjugate were used for the injection. The antibodies raised had the same specificities as those produced in the sheep and could readily discriminate between the epitopes against which they were raised.

Antibodies were raised in mice against the conjugated epitopes and also against the unconjugated epitope of the non-functional $P2X_7$ epitope (which is able to discriminate receptors that cannot from pores and thus fail to be apoptotic). In these experiments, the adjuvant used was the QIAGEN Pty Ltd product, ImmunEasy which contains the immuno-stimulatory product CpG DNA (trademark of Coley Pharmaceutical Group Inc.). 62.5 ug of epitope or conjugated epitope/mouse was diluted in 60 uL of PBS and 25 uL of ImmunEasy adjuvant. Mice were injected at multiple sites subcutaneously and intramuscularly. This regime was repeated two weeks later and again at a further two weeks. Mice were bled eight days after the third injection. Antibodies raised in mice by this method were again able to discriminate between the different P2X, epitopes and the antibodies against the $P2X_7$ non-functional epitope gave the same results as those raised in sheep and rabbits.

Example 13

Induction of Immune Response in Companion Animals

Material and Methods

Peptide

Peptide immunogen was synthesised to high purity in the form GHNYTTRNILPGLNITC (SEQ ID NO: 3) to which was added the cross-linker maleimidocaproyl-N-hydroxy-succinimide (MCS) at the C-terminal Cys residue. The peptide was cross-linked to a carrier protein Keyhole Limpet Hemocyanin (KLH) such that the average percentage of peptide to total peptide-protein conjugate was 40%. This peptide or the alternative peptide GHNYTTRNILPGA-GAKYYKENNVEKC (SEQ ID NO:33) similarly conjugated to KLH constituted selective epitope targets, primary and compound respectively that enabled differentiation of the nfP2X$_7$ receptors to be made from native receptors.

Adjuvant

Imject Alum, an approved adjuvant commonly used in human immunisations, consisting of an aqueous formulation of aluminium hydroxide and magnesium hydroxide plus inactive stabilisers in a gel, was used. The peptide-protein conjugate was added at a concentration of 2.5 mg/mL conjugate (1 mg/mL peptide) dropwise with thorough mixing in the adjuvant in an amount equal to 0.5 mL conjugate to 0.75 mL adjuvant containing 0.5 mg of target peptide epitope.

Immunisation

The immunisation schedule consisted of a primary inoculation (two injections subcutaneously and two injections intramuscularly) of a total of 0.5 mg peptide followed a month later with a boost applied the same way with 0.3 mg peptide. Serum samples were collected immediately prior to and a week post injections. Inoculation is ideally administered no less than a month after the final infusion of anti-nfP2X$_7$ antibody to ensure no sequestration of the immunogen by residual specific anti-nfP2X$_7$ antibody infusate.

ELISA

Specific anti-nfP2X$_7$ antibody responses were measured by ELISA. In brief, the ELISA plate was coated with specific target peptide epitope over which patient serum, is added in a descending concentration. After washing an appropriate secondary anti-human antibody (anti-IgM or anti-IgG types) is applied to detect and determine the concentration of specific human anti-nfP2X$_7$ antibody present in the patient serum in the form of IgM or IgG.

Following the inoculation, no IgG is detectable but a small amount of IgM is detected. Following the boost, the IgM concentration has returned to a baseline of zero while IgG is produced at higher concentration than the original IgM provided no nfP2X$_7$ receptor sink is present on extant tumor. In the absence of such a sink in animal patients for which the original tumor has been cleared by anti-nfP2X$_7$ immunotherapy, a clear population of specific endogenous anti-nfP2X$_7$ antibody is detected in the serum, of order 25 mg/kg.

FIG. 3 shows the ELISA results for a canine patient, immunized as described above. The levels of free specific circulating antibody are consistent with initial complete clearance and lack of recurrence of metastatic mast cell tumor.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for minimising the progression of cancer in a companion animal, wherein the companion animal is a dog, the method including the step of:
    administering to a dog in which the progression of cancer is to be minimized, a whole antibody or a fragment thereof including a variable domain that binds to a non-functional $P2X_7$ receptor that is expressed by the dog;
    thereby minimising the progression of cancer in the dog.

2. The method of claim 1 wherein the method is for treating cancer or condition or symptom associated with cancer in the dog.

3. The method of claim 1 wherein the whole antibody or fragment thereof does not bind to functional $P2X_7$ receptors.

4. The method of claim 1 wherein the whole antibody or fragment thereof is obtained from polyclonal antiserum.

5. The method of claim 1 wherein the whole antibody or fragment thereof is raised against an antigen that is xenogeneic to the immune system in which it is raised.

6. The method of claim 5 wherein the antigen is xenogeneic to the dog.

7. The method of claim 1 wherein the whole antibody or fragment thereof is xenogeneic to the dog.

8. The method of claim 1 wherein the cancer is one of hemangiosarcoma, metastatic mesothelioma, osteosarcoma, lymphoma, mast cell tumour, squamous cell carcinoma, mammary carcinoma, melanoma, fibrosarcoma or soft tissue sarcoma.

* * * * *

SEQUENCE LISTING

<160> NUMBER OF SEQ ID NOS: 50

<210> SEQ ID NO 1
<211> LENGTH: 595
<212> TYPE: PRT
<213> ORGANISM: Homo sapiens

<400> SEQUENCE: 1

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Val His Thr Lys
    50                  55                  60

Val Lys Gly Ile Ala Glu Val Lys Glu Glu Ile Val Glu Asn Gly Val
65              70                  75                  80

Lys Lys Leu Val His Ser Val Phe Asp Thr Ala Asp Tyr Thr Phe Pro
            85                  90                  95

Leu Gln Gly Asn Ser Phe Phe Val Met Thr Asn Phe Leu Lys Thr Glu
        100                 105                 110

Gly Gln Glu Gln Arg Leu Cys Pro Glu Tyr Pro Thr Arg Arg Thr Leu
    115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285
```

Pro Gly Tyr Asn Phe Arg Tyr Ala Lys Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
            355                 360                 365

Pro Trp Cys Lys Cys Gln Pro Cys Val Val Asn Glu Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
                500                 505                 510

Phe Arg Lys Leu Val Leu Ser Arg His Val Leu Gln Phe Leu Leu Leu
    515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
                580                 585                 590

Ser Pro Tyr
    595

<210> SEQ ID NO 2
<211> LENGTH: 595
<212> TYPE: PRT
<213> ORGANISM: Canis familiaris

<400> SEQUENCE: 2

Met Ser Ala Cys Cys Ser Cys Asn Asp Ile Phe Gln Tyr Glu Thr Asn
1               5                   10                  15

Lys Ile Ile Arg Ile Gln Ser Met Asn Tyr Gly Thr Ile Lys Trp Ile
                20                  25                  30

Phe His Val Ile Ile Phe Ser Tyr Ile Ser Phe Ala Leu Ile Ser Asp
            35                  40                  45

Lys Arg Tyr Gln Gln Lys Glu Pro Leu Ile Ser Ser Val His Thr Lys

```
                50                  55                  60
Val Lys Gly Thr Ala Glu Val Lys Met Glu Ile Leu Glu Asn Gly Ile
 65                  70                  75                  80

Lys Lys Met Val Ser Thr Val Phe Asp Thr Ala Asp Tyr Thr Phe Pro
                 85                  90                  95

Leu Gln Gly Asn Ser Phe Phe Val Met Thr Asn Phe Leu Lys Thr Glu
                100                 105                 110

Gly Gln Gln Gln Gly Phe Cys Pro Glu Phe Pro Thr Arg Arg Thr Leu
                115                 120                 125

Cys Ser Asn Asp Trp Gly Cys Lys Lys Gly Trp Met Asp Pro Gln Ser
                130                 135                 140

Lys Gly Ile Gln Thr Gly Arg Cys Ile Glu Tyr Lys Gly Lys Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Gly Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Asp Ile Asn Ile Thr Cys Thr Phe His Lys Thr Gln Asn Pro
                210                 215                 220

Gln Cys Pro Ile Phe Arg Leu Gly Asp Ile Phe Gln Gln Thr Gly Asp
225                 230                 235                 240

Asn Phe Ser Asp Val Ala Ile Gln Gly Gly Ile Met Gly Ile Glu Ile
                245                 250                 255

His Trp Asp Cys Asn Leu Asp Ser Trp Phe His His Cys Arg Pro Lys
                260                 265                 270

Tyr Ser Phe Arg Arg Leu Asp Asp Lys Asn Thr Thr Thr Glu Ser Leu
                275                 280                 285

Tyr Pro Gly Tyr Asn Phe Arg Tyr Ala Lys Tyr Tyr Lys Glu Asn Asn
                290                 295                 300

Val Glu Lys Arg Thr Leu Ile Lys Val Phe Gly Ile Arg Phe Asp Ile
305                 310                 315                 320

Leu Val Phe Gly Thr Gly Gly Lys Phe Asp Ile Ile Gln Leu Val Val
                325                 330                 335

Tyr Ile Gly Ser Thr Leu Ser Tyr Phe Gly Leu Ala Thr Leu Phe Ile
                340                 345                 350

Asp Phe Leu Ile Asn Thr Tyr Ser Ser Lys Cys Cys Arg Ser His Ile
                355                 360                 365

Tyr Pro Cys Phe Lys Cys Cys Glu Tyr Cys Ala Val Asn Glu Tyr Tyr
                370                 375                 380

Tyr Lys Lys Lys Cys Glu Thr Ile Val Glu Pro Lys Pro Thr Leu Lys
385                 390                 395                 400

Tyr Val Ser Phe Val Asp Glu Ala His Ile Arg Met Val Asp Gln Gln
                405                 410                 415

Leu Leu Arg Arg Arg Leu Gln Asp Val Glu Gly Glu Glu Val Pro Arg
                420                 425                 430

Pro Ser Met Glu Phe Thr Asp Leu Ser Arg Leu Ser Leu Ser Leu His
                435                 440                 445

Asp Leu Ser Pro Ile Pro Gly Gln Ser Glu Glu Met Gln Leu Leu Ser
                450                 455                 460

Glu Glu Val Thr Pro Arg Ser Ser Asn Ser Pro Asp Trp Cys Gln Cys
465                 470                 475                 480
```

```
Gly His Cys Leu Pro Ser Gln Leu Pro Glu Ser Gln Arg Cys Leu Glu
                485                 490                 495

Glu Leu Cys Cys Arg Lys Lys Ala Gly Ala Cys Ile Thr Thr Ser Glu
            500                 505                 510

Pro Phe Arg Lys Leu Ile Leu Ser Arg Gln Val Leu Gln Phe Leu Leu
            515                 520                 525

Leu Tyr Gln Glu Pro Leu Leu Val Leu Asp Glu Asn Ser Asn Ser Arg
        530                 535                 540

Leu Arg His Cys Ala Tyr Arg Cys Tyr Thr Thr Trp Arg Phe Gly Ser
545                 550                 555                 560

Gln Asp Leu Ala Asp Phe Ala Ile Leu Pro Ser Cys Cys Arg Trp Arg
                565                 570                 575

Ile Arg Arg Glu Phe Pro Lys Ser Glu Gly Gln Tyr Ser Gly Phe Arg
            580                 585                 590

Ser Pro Tyr
        595

<210> SEQ ID NO 3
<211> LENGTH: 17
<212> TYPE: PRT
<213> ORGANISM: Homo sapiens

<400> SEQUENCE: 3

Gly His Asn Tyr Thr Thr Arg Asn Ile Leu Pro Gly Leu Asn Ile Thr
1               5                   10                  15

Cys

<210> SEQ ID NO 4
<211> LENGTH: 17
<212> TYPE: PRT
<213> ORGANISM: Canis familiaris

<400> SEQUENCE: 4

Gly His Asn Tyr Thr Thr Arg Asn Ile Leu Pro Asp Ile Asn Ile Thr
1               5                   10                  15

Cys

<210> SEQ ID NO 5
<211> LENGTH: 18
<212> TYPE: PRT
<213> ORGANISM: Homo sapiens

<400> SEQUENCE: 5

Ala Lys Tyr Tyr Lys Glu Asn Asn Val Glu Lys Arg Thr Leu Ile Lys
1               5                   10                  15

Val Phe

<210> SEQ ID NO 6
<211> LENGTH: 12
<212> TYPE: PRT
<213> ORGANISM: Pan troglodytes

<400> SEQUENCE: 6

Gly His Asn Tyr Thr Thr Arg Asn Ile Leu Pro Gly
1               5                   10

<210> SEQ ID NO 7
<211> LENGTH: 11
<212> TYPE: PRT
```

<213> ORGANISM: Pan troglodytes

<400> SEQUENCE: 7

Ala Lys Tyr Tyr Lys Glu Asn Asn Val Glu Lys
1               5                   10

<210> SEQ ID NO 8
<211> LENGTH: 12
<212> TYPE: PRT
<213> ORGANISM: Macaca mulatta

<400> SEQUENCE: 8

Gly His Asn Tyr Thr Thr Arg Asn Ile Leu Pro Gly
1               5                   10

<210> SEQ ID NO 9
<211> LENGTH: 11
<212> TYPE: PRT
<213> ORGANISM: Macaca mulatta

<400> SEQUENCE: 9

Ala Lys Tyr Tyr Lys Glu Asn Asn Val Glu Lys
1               5                   10

<210> SEQ ID NO 10
<211> LENGTH: 12
<212> TYPE: PRT
<213> ORGANISM: Pongo pygmaeus

<400> SEQUENCE: 10

Gly His Asn Tyr Thr Thr Arg Asn Ile Leu Pro Gly
1               5                   10

<210> SEQ ID NO 11
<211> LENGTH: 11
<212> TYPE: PRT
<213> ORGANISM: Pongo pygmaeus

<400> SEQUENCE: 11

Ala Lys Tyr Tyr Lys Glu Asn Asn Val Glu Lys
1               5                   10

<210> SEQ ID NO 12
<211> LENGTH: 12
<212> TYPE: PRT
<213> ORGANISM: Callithrix pygmaea

<400> SEQUENCE: 12

Gly His Asn Tyr Thr Thr Arg Asn Ile Leu Pro Gly
1               5                   10

<210> SEQ ID NO 13
<211> LENGTH: 11
<212> TYPE: PRT
<213> ORGANISM: Callithrix pygmaea

<400> SEQUENCE: 13

Ala Lys Tyr Tyr Lys Glu Asn Asn Val Glu Lys
1               5                   10

<210> SEQ ID NO 14
<211> LENGTH: 12
<212> TYPE: PRT
<213> ORGANISM: Equus caballus

```
<400> SEQUENCE: 14

Gly His Asn Tyr Thr Thr Arg Asn Ile Leu Pro Gly
1               5                   10

<210> SEQ ID NO 15
<211> LENGTH: 11
<212> TYPE: PRT
<213> ORGANISM: Equus caballus

<400> SEQUENCE: 15

Ala Lys Tyr Tyr Lys Glu Asn Asn Val Glu Lys
1               5                   10

<210> SEQ ID NO 16
<211> LENGTH: 12
<212> TYPE: PRT
<213> ORGANISM: Canis lupus

<400> SEQUENCE: 16

Gly His Asn Tyr Thr Thr Arg Asn Ile Leu Pro Gly
1               5                   10

<210> SEQ ID NO 17
<211> LENGTH: 11
<212> TYPE: PRT
<213> ORGANISM: Canis lupus

<400> SEQUENCE: 17

Ala Lys Tyr Tyr Lys Glu Asn Asn Val Glu Lys
1               5                   10

<210> SEQ ID NO 18
<211> LENGTH: 12
<212> TYPE: PRT
<213> ORGANISM: Ailuropoda melanoleuca

<400> SEQUENCE: 18

Gly His Asn Tyr Thr Thr Arg Asn Ile Leu Pro Gly
1               5                   10

<210> SEQ ID NO 19
<211> LENGTH: 11
<212> TYPE: PRT
<213> ORGANISM: Ailuropoda melanoleuca

<400> SEQUENCE: 19

Ala Lys Tyr Tyr Lys Glu Asn Asn Val Glu Lys
1               5                   10

<210> SEQ ID NO 20
<211> LENGTH: 12
<212> TYPE: PRT
<213> ORGANISM: Sus scrofa

<400> SEQUENCE: 20

Gly His Asn Tyr Thr Thr Arg Asn Ile Leu Pro Gly
1               5                   10

<210> SEQ ID NO 21
<211> LENGTH: 11
<212> TYPE: PRT
<213> ORGANISM: Sus scrofa

<400> SEQUENCE: 21
```

Ala Lys Tyr Tyr Lys Glu Asn Asn Val Glu Lys
1               5                   10

<210> SEQ ID NO 22
<211> LENGTH: 12
<212> TYPE: PRT
<213> ORGANISM: Sus scrofa

<400> SEQUENCE: 22

Gly His Asn Tyr Thr Thr Arg Asn Ile Leu Pro Gly
1               5                   10

<210> SEQ ID NO 23
<211> LENGTH: 11
<212> TYPE: PRT
<213> ORGANISM: Sus scrofa

<400> SEQUENCE: 23

Ala Lys Tyr Tyr Lys Glu Asn Asn Val Glu Lys
1               5                   10

<210> SEQ ID NO 24
<211> LENGTH: 12
<212> TYPE: PRT
<213> ORGANISM: Mus musculus

<400> SEQUENCE: 24

Gly His Asn Tyr Thr Thr Arg Asn Ile Leu Pro Gly
1               5                   10

<210> SEQ ID NO 25
<211> LENGTH: 11
<212> TYPE: PRT
<213> ORGANISM: Mus musculus

<400> SEQUENCE: 25

Ala Lys Tyr Tyr Lys Glu Asn Asn Val Glu Lys
1               5                   10

<210> SEQ ID NO 26
<211> LENGTH: 12
<212> TYPE: PRT
<213> ORGANISM: Cavia porcellus

<400> SEQUENCE: 26

Gly His Asn Tyr Thr Thr Arg Asn Ile Leu Pro Gly
1               5                   10

<210> SEQ ID NO 27
<211> LENGTH: 11
<212> TYPE: PRT
<213> ORGANISM: Cavia porcellus

<400> SEQUENCE: 27

Ala Lys Tyr Tyr Arg Glu Asn Asn Val Glu Lys
1               5                   10

<210> SEQ ID NO 28
<211> LENGTH: 12
<212> TYPE: PRT
<213> ORGANISM: Bos taurus

<400> SEQUENCE: 28

Gly His Asn Tyr Thr Thr Arg Asn Ile Leu Pro Gly
1               5                   10

<210> SEQ ID NO 29
<211> LENGTH: 11
<212> TYPE: PRT
<213> ORGANISM: Bos taurus

<400> SEQUENCE: 29

Ala Lys Tyr Tyr Lys Glu Asn Asn Thr Glu Lys
1               5                   10

<210> SEQ ID NO 30
<211> LENGTH: 12
<212> TYPE: PRT
<213> ORGANISM: Rattus rattus

<400> SEQUENCE: 30

Gly His Asn Tyr Thr Thr Arg Asn Ile Leu Pro Gly
1               5                   10

<210> SEQ ID NO 31
<211> LENGTH: 11
<212> TYPE: PRT
<213> ORGANISM: Rattus rattus

<400> SEQUENCE: 31

Ala Lys Tyr Tyr Lys Glu Asn Gly Met Glu Lys
1               5                   10

<210> SEQ ID NO 32
<211> LENGTH: 25
<212> TYPE: PRT
<213> ORGANISM: Artificial Sequence
<220> FEATURE:
<223> OTHER INFORMATION: Synthesized

<400> SEQUENCE: 32

Gly His Asn Tyr Thr Thr Arg Asn Ile Leu Pro Gly Ala Gly Ala Lys
1               5                   10                  15

Tyr Tyr Lys Glu Asn Asn Val Glu Lys
            20                  25

<210> SEQ ID NO 33
<211> LENGTH: 26
<212> TYPE: PRT
<213> ORGANISM: Artificial Sequence
<220> FEATURE:
<223> OTHER INFORMATION: Synthesized

<400> SEQUENCE: 33

Gly His Asn Tyr Thr Thr Arg Asn Ile Leu Pro Gly Ala Gly Ala Lys
1               5                   10                  15

Tyr Tyr Lys Glu Asn Asn Val Glu Lys Cys
            20                  25

<210> SEQ ID NO 34
<211> LENGTH: 553
<212> TYPE: PRT
<213> ORGANISM: Xenopus laevis

<400> SEQUENCE: 34

Met Thr Leu Thr Leu Ala Asp Cys Phe Asp Tyr Ser Thr Lys Lys Glu
1               5                   10                  15

Val Arg Ile Gln Ser Val Pro Leu Gly Ile Leu Lys Gln Cys Ile Thr
            20                  25                  30

```
Phe Gly Val Ile Val Phe Val Cys Phe Ser Leu Ile Thr Gln Lys Arg
            35                  40                  45

Tyr Gln Lys Lys Asp Ser Ile Ile Ser Ser Val His Thr Lys Val Lys
     50                  55                  60

Gly Phe Ala Asp Ala His Ser Arg Ile Trp Asp Thr Ala Glu Tyr Thr
 65                  70                  75                  80

Val Pro Ser Pro Gly Gly Asp Ser Phe Phe Val Ile Thr Asn Ile Val
                     85                  90                  95

Lys Thr Glu Gly Gln Met Gln Ser Asn Cys Ser Glu Leu Pro Ser Gln
                100                 105                 110

Lys Thr Ile Cys Ser Arg Asp Asp Ile Cys Lys Lys Gly Leu Ala Asp
                115                 120                 125

Pro Gln Ser Asn Gly Ile Gln Thr Gly Arg Cys Ile Asn Phe Asn Asn
    130                 135                 140

Thr Leu Lys Thr Cys Glu Val Ser Ala Trp Cys Pro Val Glu Ser Gln
145                 150                 155                 160

Thr Thr Pro Val Pro Ala Val Leu Glu Ser Ala Glu Asn Phe Thr Val
                165                 170                 175

Leu Ile Lys Asn Asn Ile His Phe Ala Ala Phe Asn Phe Thr Lys Lys
                180                 185                 190

Asn Ile Leu Pro Asn Tyr Asn Val Ser Cys Ile Tyr Asp Arg Val Lys
                195                 200                 205

Ala Pro Leu Cys Pro Ile Phe Arg Leu Gly Asp Ile Leu Arg Glu Ala
    210                 215                 220

Gly Glu Asn Phe Ser Gln Val Ala Val Leu Gly Gly Val Ile Gly Ile
225                 230                 235                 240

Glu Ile Asn Trp Asp Cys Asp Leu Asp Pro Leu Arg Tyr Lys Cys Glu
                245                 250                 255

Pro His Tyr Gly Phe Arg Arg Leu Asp Asp Thr Val Val Asp Glu Ser
                260                 265                 270

Leu Tyr Pro Gly Leu Asn Phe Arg Phe Ala Arg Tyr Tyr Lys Asn Ala
    275                 280                 285

His Gly Thr Glu Thr Arg Thr Leu Ile Lys Ala Tyr Gly Ile Arg Phe
290                 295                 300

Asp Ile Gln Val Tyr Gly Thr Gly Gly Gln Phe Asn Leu Leu Glu Leu
305                 310                 315                 320

Ala Leu Phe Ile Gly Ser Cys Leu Ser Tyr Phe Gly Cys Ala Ser Phe
                325                 330                 335

Ala Ile Asp Phe Ile Ile Gly Arg Tyr Asn Ser Cys Cys Cys Asn Ala
                340                 345                 350

Lys Ser Val Leu Lys Tyr Tyr Asp Asp Arg Lys Tyr Glu Thr Ile Pro
    355                 360                 365

Gly Pro Ser Val Ser Leu Ala His Leu Lys Ala His Leu Lys Phe Val
    370                 375                 380

Ser Phe Val Asp Lys Glu Asp Ile Leu Met Val Asp Gln Lys Leu Lys
385                 390                 395                 400

Gly Ser Leu Gln Leu Ala Ser Gly Pro Tyr Ile Gln Arg Glu Arg Phe
                405                 410                 415

Ala Asp Thr Lys Ala Lys Cys Lys Asp Ser His Lys Gln Asp Glu Asn
                420                 425                 430

Glu Met Arg Leu Ile Lys Gly Arg Ser Ala Met Leu Pro Pro Ala Trp
                435                 440                 445
```

```
Cys Lys Cys Asn Lys Cys Ile Asn Thr Thr His Leu Glu Glu Gln Leu
    450                 455                 460
Cys Cys Arg Leu Glu Glu Gly Glu Cys Ile Thr Asp Thr Lys Met Phe
465                 470                 475                 480
Asn Ser Leu Val Leu Asn Arg Glu Ser Leu Glu Tyr Ala Phe Gln Tyr
                485                 490                 495
Asp Asn Pro Leu Ser Lys Thr Pro Ile Ser Lys Glu His Leu Arg Tyr
            500                 505                 510
Tyr Ala Lys Gln Lys Tyr Val Glu Trp Arg Phe Gly Cys Arg Lys Tyr
        515                 520                 525
Met Leu Asn Phe Ala Val Ile Pro Asn Cys Cys Lys Thr Ala Ile Glu
    530                 535                 540
Thr Cys Asn Leu Gln Thr Glu Gly Pro
545                 550

<210> SEQ ID NO 35
<211> LENGTH: 568
<212> TYPE: PRT
<213> ORGANISM: Xenopus tropicalis

<400> SEQUENCE: 35

Met Ala Pro Thr Phe Ala Asp Cys Phe Asp Tyr Ser Thr Lys Lys Glu
1               5                   10                  15
Ile Arg Ile Gln Ser Val Pro Leu Gly Val Leu Lys Phe Leu Ile Thr
            20                  25                  30
Phe Gly Val Ile Leu Phe Val Cys Phe Ser Leu Ile Thr Gln Lys Ser
        35                  40                  45
Tyr Gln Lys Lys Val Ser Val Ile Ser Ser Val His Thr Lys Val Lys
    50                  55                  60
Gly Ile Ala Asp Ala Tyr Ser Arg Ile Trp Asp Thr Ala Glu Tyr Thr
65                  70                  75                  80
Val Pro Ser Pro Gly Gly Asp Ser Phe Phe Val Val Thr Asn Ile Val
                85                  90                  95
Lys Thr Glu Asp Gln Arg Gln Ser Asn Cys Pro Glu Leu Pro Arg Gln
            100                 105                 110
Lys Thr Ile Cys Ser Arg Asp Asp Val Cys Lys Lys Gly Leu Ala Asp
        115                 120                 125
Pro Gln Ser Asn Gly Ile Gln Thr Gly Arg Cys Ile Asn Phe Asn Ser
    130                 135                 140
Thr Leu Lys Thr Cys Glu Val Ser Ala Trp Cys Pro Val Glu Ser Gln
145                 150                 155                 160
Thr Thr Pro Val Pro Ala Val Leu Glu Ser Ala Glu Asn Phe Thr Val
                165                 170                 175
Leu Ile Lys Asn Asn Ile His Phe Ala Ala Phe Asn Phe Thr Lys Lys
            180                 185                 190
Asn Ile Leu Pro Lys Tyr Asn Val Ser Cys Ile Tyr Asp Arg Val Lys
        195                 200                 205
Ala Pro Leu Cys Pro Ile Phe Arg Leu Gly Asp Ile Leu Arg Glu Ala
    210                 215                 220
Gly Glu Asn Phe Ser Gln Val Ala Val Leu Gly Gly Val Ile Gly Ile
225                 230                 235                 240
Glu Ile Asn Trp Asp Cys Asp Leu Asp Ser Leu Arg Tyr Lys Cys Glu
                245                 250                 255
Pro His Tyr Ser Phe Arg Arg Leu Asp Asp Lys Val Val Asp Glu Arg
            260                 265                 270
```

Leu Tyr Pro Gly Leu Asn Phe Arg Phe Ala Arg Tyr Tyr Lys Thr Ser
            275                 280                 285

Asp Gly Lys Glu Thr Arg Thr Leu Ile Lys Ala Tyr Gly Ile Arg Phe
        290                 295                 300

Asp Ile Gln Val Tyr Gly Met Gly Gly Lys Phe Asn Leu Phe Glu Leu
305                 310                 315                 320

Ala Ile Phe Ile Gly Ser Cys Leu Ser Tyr Phe Gly Cys Ala Ser Leu
                325                 330                 335

Ala Ile Asp Phe Ile Ile Gly Leu Tyr Lys Pro Cys Cys Asn Ala
            340                 345                 350

Lys Ser Val Leu Lys Tyr Asp Asp Arg Lys Tyr Glu Lys Val Pro
            355                 360                 365

Gly Pro Thr Val Ala Gln Val Lys Tyr Cys His Phe Leu Ser Gln Leu
        370                 375                 380

Lys Phe Val Ser Phe Val Asp Lys Glu Asp Ile Leu Met Val Asp Ile
385                 390                 395                 400

Asn Ser Arg Gly Ser Leu Gln Phe Ala Ser Gly Gln His Ile Gln Arg
                405                 410                 415

Glu Arg Phe Glu Tyr Thr Glu Ala Lys Cys Lys Asp Ser His Lys Lys
            420                 425                 430

Asn Gln Thr Glu Met Arg Leu Ile Lys Gly Ser Ser Thr Thr Leu Pro
        435                 440                 445

Pro Ala Trp Cys Lys Cys Asn Lys Cys Ile Asp Val Thr Gln Pro Glu
    450                 455                 460

Glu Gln Leu Cys Cys Arg Leu Gly Gln Gly Cys Ile Thr Asp Thr
465                 470                 475                 480

Glu Met Phe Lys Tyr Leu Val Leu Asn Lys Glu Ala Leu Glu Tyr Ala
                485                 490                 495

Phe Gln Tyr Asp Asn Pro Leu Ser Lys Thr Pro Glu Ser Glu Asp Leu
            500                 505                 510

Lys Cys Tyr Ala Lys Gln Lys Tyr Ile Glu Trp Arg Phe Gly Cys Arg
        515                 520                 525

Arg Tyr Met Leu Asp Phe Ala Val Ile Pro Ser Cys Cys Lys Asn Ala
    530                 535                 540

Ile Glu Thr Cys Asn Leu Gln Thr Gln His Pro Ser Gly Ala Leu Tyr
545                 550                 555                 560

Leu Pro Pro Thr His Gly Met Cys
            565

<210> SEQ ID NO 36
<211> LENGTH: 560
<212> TYPE: PRT
<213> ORGANISM: Gallus gallus

<400> SEQUENCE: 36

Met Val Ala Trp Gly Trp Met Lys Asp Val Phe Asn Tyr Glu Ser Pro
1               5                   10                  15

Lys Leu Ile Arg Phe Pro Ser Val Gly Leu Val Cys Val Lys Trp Phe
            20                  25                  30

Ile Tyr Gly Val Ile Ala Val Tyr Ile Cys Tyr Thr Leu Ile Val His
        35                  40                  45

Lys Arg Tyr Gln Glu Lys Glu Glu Leu Thr Ser Ser Val Arg Val Thr
    50                  55                  60

Leu Lys Gly Val Ala His Val Asp Arg Ile Trp Asp Ala Ala Glu Tyr

-continued

```
            65                  70                  75                  80
Thr Ile Pro Thr Gln Thr Arg Asp Ser Phe Phe Val Met Thr Asn Ile
                    85                  90                  95

Ile Arg Thr Glu Asn Gln Ile Gln Lys Thr Cys Pro Glu Tyr Pro Thr
                100                 105                 110

Ala Lys Ala Ile Cys Ser Ser Asp Lys Ser Cys Ala Lys Gly Ile Val
                115                 120                 125

Asp Val His Ser Asn Gly Val Gln Thr Gly Lys Cys Val His Tyr Asn
            130                 135                 140

Ile Thr His Lys Thr Cys Glu Ile Lys Ala Trp Cys Pro Val Gln Gly
145                 150                 155                 160

Glu Glu Arg Pro Pro Val Pro Ala Val Leu Arg Ser Ser Glu Asp Phe
                165                 170                 175

Thr Val Phe Ile Lys Asn Asn Ile His Phe Pro Thr Phe Asn Tyr Thr
                180                 185                 190

Val Gln Asn Ile Ser Pro Lys Leu Asn Thr Ser Cys Lys Phe Asn Lys
                195                 200                 205

Val Thr Ala Pro Leu Cys Pro Ile Phe Arg Leu Gly Asp Ile Leu Gln
            210                 215                 220

Glu Ala Lys Glu Asn Phe Ser Glu Met Ala Val Lys Gly Gly Ile Ile
225                 230                 235                 240

Ala Ile Glu Ile Lys Trp Asp Cys Asp Leu Asp Ser Trp Ser Tyr Tyr
                245                 250                 255

Cys Ser Pro Glu Tyr Ser Phe Arg Arg Leu Asp Asp Lys Thr Arg Thr
                260                 265                 270

Gln Tyr Pro Gly Phe Ser Ile Arg Phe Ala Arg His Tyr Lys Leu Pro
            275                 280                 285

Asp Gly Thr Glu Gln Arg Thr Leu Phe Lys Ala Tyr Gly Ile Arg Phe
            290                 295                 300

Asp Val Leu Val Phe Gly Met Gly Gly Gln Phe Lys Leu Ile Glu Leu
305                 310                 315                 320

Phe Thr Phe Ile Gly Ser Thr Ile Ala Tyr Phe Gly Leu Ala Val Thr
                325                 330                 335

Ile Ile Glu Met Cys Phe His Leu Tyr Asn Cys Ser Ser Cys Cys Lys
                340                 345                 350

Ile Gln Val Cys Glu Asn Val Ile Arg Lys Tyr Glu Thr Val Leu
                355                 360                 365

Met Pro Glu Gln Val Ile Leu Val Ser Tyr Val Asp Lys Pro His Ile
370                 375                 380

Thr Leu Ile Lys Met Pro Leu Arg Thr Ser Leu Gln Asn Ala Glu Gly
385                 390                 395                 400

Ser Ile Phe Glu Asp His Pro Val Lys Ser Tyr Asp Pro Arg Thr Cys
                405                 410                 415

Cys Ser His Lys Ser Asn Glu Lys His Gly Ala Ala Gln Ser Glu Leu
                420                 425                 430

Arg Pro Leu Thr Gln Ser Ser Ser Thr Asn Cys Pro Lys Trp Cys
                435                 440                 445

Cys Cys Gly Arg Cys Gln Val Ala Gln Lys His Glu Gln Leu Cys
            450                 455                 460

Cys Arg Lys Lys Glu Gly Gln Cys Ile Thr Thr Tyr Trp Phe Ala
465                 470                 475                 480

Gln Leu Val Leu Ser Arg Asp Thr Leu Asn Lys Ala Leu Leu Tyr Glu
                485                 490                 495
```

```
Asp Pro Phe Leu Asp Leu Thr Gly His Ser Ser Asn Ser Gln Leu Arg
        500                 505                 510

Arg Ile Ala Tyr Lys Gln Tyr Ile His Trp Arg Phe Gly Ser Phe Glu
        515                 520                 525

Leu Glu Asp Arg Ala Ile Ile Pro Ser Cys Cys Arg Arg Leu Ile Arg
        530                 535                 540

Ser Thr Tyr Pro Lys Glu Asn Gly Asn Tyr Thr Gly Phe Asn Leu Glu
545                 550                 555                 560

<210> SEQ ID NO 37
<211> LENGTH: 592
<212> TYPE: PRT
<213> ORGANISM: Rattus norvegicus

<400> SEQUENCE: 37

Met Leu Pro Val Arg His Leu Cys Ser Tyr Asn Ser Ala Lys Val Leu
1               5                   10                  15

His Ile His Ser Thr Arg Leu Gly Ala Leu Lys Asn Phe Phe Leu Leu
            20                  25                  30

Ala Ile Cys Ile Tyr Ile Cys Phe Ala Leu Met Ser Asp Lys Leu Tyr
        35                  40                  45

Gln Arg Lys Glu Pro Leu Ile Ser Ser Val His Thr Lys Val Lys Gly
    50                  55                  60

Val Ala Glu Val Thr Glu Asn Val Thr Glu Gly Val Thr Lys Leu
65                  70                  75                  80

Val His Gly Ile Phe Asp Thr Ala Asp Tyr Thr Leu Pro Leu Gln Gly
                85                  90                  95

Asn Ser Phe Phe Val Met Thr Asn Tyr Leu Lys Ser Glu Gly Gln Glu
            100                 105                 110

Gln Lys Leu Cys Pro Glu Tyr Pro Ser Arg Gly Lys Gln Cys His Ser
        115                 120                 125

Asp Gln Gly Cys Ile Lys Gly Trp Met Asp Pro Gln Ser Lys Gly Ile
    130                 135                 140

Gln Thr Gly Arg Cys Ile Pro Tyr Asp Gln Lys Arg Lys Thr Cys Glu
145                 150                 155                 160

Ile Phe Ala Trp Cys Pro Ala Glu Glu Gly Lys Glu Ala Pro Arg Pro
                165                 170                 175

Ala Leu Leu Arg Ser Ala Glu Asn Phe Thr Val Leu Ile Lys Asn Asn
            180                 185                 190

Ile Asp Phe Pro Gly His Asn Tyr Thr Thr Arg Asn Ile Leu Pro Gly
        195                 200                 205

Met Asn Ile Ser Cys Thr Phe His Lys Thr Trp Asn Pro Gln Cys Pro
    210                 215                 220

Ile Phe Arg Leu Gly Asp Ile Phe Gln Glu Ile Gly Glu Asn Phe Thr
225                 230                 235                 240

Glu Val Ala Val Gln Gly Gly Ile Met Gly Ile Glu Ile Tyr Trp Asp
                245                 250                 255

Cys Asn Leu Asp Ser Trp Ser His Arg Cys Gln Pro Lys Tyr Ser Phe
            260                 265                 270

Arg Arg Leu Asp Asp Lys Tyr Thr Asn Glu Ser Leu Phe Pro Gly Tyr
        275                 280                 285

Asn Phe Arg Tyr Ala Lys Tyr Tyr Lys Glu Asn Gly Met Glu Lys Arg
    290                 295                 300

Thr Leu Ile Lys Ala Phe Gly Val Arg Phe Asp Ile Leu Val Phe Gly
```

```
                305                 310                 315                 320
        Thr Gly Gly Lys Phe Asp Ile Ile Gln Leu Val Val Tyr Ile Gly Ser
                        325                 330                 335

Thr Leu Ser Tyr Phe Gly Leu Ala Thr Val Cys Ile Asp Leu Ile Ile
                        340                 345                 350

Asn Thr Tyr Ala Ser Thr Cys Cys Arg Ser Arg Val Tyr Pro Ser Cys
                        355                 360                 365

Lys Cys Cys Glu Pro Cys Ala Val Asn Glu Tyr Tyr Arg Lys Lys
        370                 375                 380

Cys Glu Pro Ile Val Glu Pro Lys Pro Thr Leu Lys Tyr Val Ser Phe
        385                 390                 395                 400

Val Asp Glu Pro His Ile Trp Met Val Asp Gln Gln Leu Leu Gly Lys
                        405                 410                 415

Ser Leu Gln Asp Val Lys Gly Gln Glu Val Pro Arg Pro Gln Thr Asp
                        420                 425                 430

Phe Leu Glu Leu Ser Arg Leu Ser Leu Ser Leu His His Ser Pro Pro
                        435                 440                 445

Ile Pro Gly Gln Pro Glu Glu Met Gln Leu Leu Gln Ile Glu Ala Val
                450                 455                 460

Pro Arg Ser Arg Asp Ser Pro Asp Trp Cys Gln Cys Gly Asn Cys Leu
        465                 470                 475                 480

Pro Ser Gln Leu Pro Glu Asn Arg Arg Ala Leu Glu Glu Leu Cys Cys
                        485                 490                 495

Arg Arg Lys Pro Gly Gln Cys Ile Thr Thr Ser Glu Leu Phe Ser Lys
                        500                 505                 510

Ile Val Leu Ser Arg Glu Ala Leu Gln Leu Leu Leu Tyr Gln Glu
                        515                 520                 525

Pro Leu Leu Ala Leu Glu Gly Glu Ala Ile Asn Ser Lys Leu Arg His
                        530                 535                 540

Cys Ala Tyr Arg Ser Tyr Ala Thr Trp Arg Phe Val Ser Gln Asp Met
        545                 550                 555                 560

Ala Asp Phe Ala Ile Leu Pro Ser Cys Cys Arg Trp Lys Ile Arg Lys
                        565                 570                 575

Glu Phe Pro Lys Thr Gln Gly Gln Tyr Ser Gly Phe Lys Tyr Pro Tyr
                        580                 585                 590

<210> SEQ ID NO 38
<211> LENGTH: 597
<212> TYPE: PRT
<213> ORGANISM: Mus musculus

<400> SEQUENCE: 38

Gly Leu Cys Arg Ala Cys Cys Ser Trp Asn Asp Val Leu Gln Tyr Glu
        1               5                   10                  15

Thr Asn Lys Val Thr Arg Ile Gln Ser Thr Asn Tyr Gly Thr Val Lys
                        20                  25                  30

Trp Val Leu His Met Ile Val Phe Ser Tyr Ile Ser Phe Ala Leu Val
                        35                  40                  45

Ser Asp Lys Leu Tyr Gln Arg Lys Glu Pro Val Ile Ser Ser Val His
                        50                  55                  60

Thr Lys Val Lys Gly Ile Ala Glu Val Thr Glu Asn Val Thr Glu Gly
        65                  70                  75                  80

Gly Val Thr Lys Leu Gly His Ser Ile Phe Asp Thr Ala Asp Tyr Thr
                        85                  90                  95
```

```
Phe Pro Leu Gln Gly Asn Ser Phe Phe Val Met Thr Asn Tyr Val Lys
                100                 105                 110

Ser Glu Gly Gln Val Gln Thr Leu Cys Pro Glu Tyr Pro Arg Arg Gly
            115                 120                 125

Ala Gln Cys Ser Ser Asp Arg Arg Cys Lys Lys Gly Trp Met Asp Pro
        130                 135                 140

Gln Ser Lys Gly Ile Gln Thr Gly Arg Cys Val Pro Tyr Asp Lys Thr
145                 150                 155                 160

Arg Lys Thr Cys Glu Val Ser Ala Trp Cys Pro Thr Glu Glu Lys
                165                 170                 175

Glu Ala Pro Arg Pro Ala Leu Leu Arg Ser Ala Glu Asn Phe Thr Val
            180                 185                 190

Leu Ile Lys Asn Asn Ile His Phe Pro Gly His Asn Tyr Thr Thr Arg
        195                 200                 205

Asn Ile Leu Pro Thr Met Asn Gly Ser Cys Thr Phe His Lys Thr Trp
210                 215                 220

Asp Pro Gln Cys Ser Ile Phe Arg Leu Gly Asp Ile Phe Gln Glu Ala
225                 230                 235                 240

Gly Glu Asn Phe Thr Glu Val Ala Val Gln Gly Gly Ile Met Gly Ile
            245                 250                 255

Glu Ile Tyr Trp Asp Cys Asn Leu Asp Ser Trp Ser His His Cys Arg
        260                 265                 270

Pro Arg Tyr Ser Phe Arg Arg Leu Asp Asp Lys Asn Thr Asp Glu Ser
            275                 280                 285

Phe Val Pro Gly Tyr Asn Phe Arg Tyr Ala Lys Tyr Tyr Lys Glu Asn
        290                 295                 300

Asn Val Glu Lys Arg Thr Leu Ile Lys Ala Phe Gly Ile Arg Phe Asp
305                 310                 315                 320

Ile Leu Val Phe Gly Thr Gly Gly Lys Phe Asp Ile Ile Gln Leu Val
                325                 330                 335

Val Tyr Ile Gly Ser Thr Leu Ser Tyr Phe Gly Leu Ala Thr Val Cys
            340                 345                 350

Ile Asp Leu Leu Ile Asn Thr Tyr Ser Ser Ala Phe Cys Arg Ser Gly
        355                 360                 365

Val Tyr Pro Tyr Cys Lys Cys Cys Glu Pro Cys Thr Val Asn Glu Tyr
370                 375                 380

Tyr Tyr Arg Lys Lys Cys Glu Ser Ile Met Glu Pro Lys Pro Thr Leu
385                 390                 395                 400

Lys Tyr Val Ser Phe Val Asp Glu Pro His Ile Arg Met Val Asp Gln
                405                 410                 415

Gln Leu Leu Gly Lys Ser Leu Gln Val Val Lys Gly Gln Glu Val Pro
            420                 425                 430

Arg Pro Gln Met Asp Phe Ser Asp Leu Ser Arg Leu Ser Leu Ser Leu
        435                 440                 445

His Asp Ser Pro Pro Thr Pro Gly Gln Ser Glu Ile Gln Leu Leu
450                 455                 460

His Glu Glu Val Ala Pro Lys Ser Gly Asp Ser Pro Ser Trp Cys Gln
465                 470                 475                 480

Cys Gly Asn Cys Leu Pro Ser Arg Leu Pro Glu Gln Arg Arg Ala Leu
                485                 490                 495

Glu Glu Leu Cys Cys Arg Arg Lys Pro Gly Arg Cys Ile Thr Thr Ser
            500                 505                 510

Lys Leu Phe His Lys Leu Val Leu Ser Arg Asp Thr Leu Gln Leu Leu
```

```
                515                 520                 525
Leu Leu Tyr Gln Asp Pro Leu Val Leu Gly Glu Glu Ala Thr Asn
    530                 535                 540
Ser Arg Leu Arg His Arg Ala Tyr Arg Cys Tyr Ala Thr Trp Arg Phe
545                 550                 555                 560
Gly Ser Gln Asp Met Ala Asp Phe Ala Ile Leu Pro Ser Cys Cys Arg
                565                 570                 575
Trp Arg Ile Arg Lys Glu Phe Pro Lys Thr Glu Gly Gln Tyr Ser Gly
                580                 585                 590
Phe Lys Tyr Pro Tyr
            595

<210> SEQ ID NO 39
<211> LENGTH: 595
<212> TYPE: PRT
<213> ORGANISM: Pan troglodytes

<400> SEQUENCE: 39

Met Pro Ala Cys Cys Ser Cys Ser Asp Val Phe Gln Tyr Glu Thr Asn
1               5                   10                  15
Lys Val Thr Arg Ile Gln Ser Met Asn Tyr Gly Thr Ile Lys Trp Phe
            20                  25                  30
Phe His Val Ile Ile Phe Ser Tyr Val Cys Phe Ala Leu Val Ser Asp
        35                  40                  45
Lys Leu Tyr Gln Arg Lys Glu Pro Val Ile Ser Ser Val His Thr Lys
    50                  55                  60
Val Lys Gly Ile Ala Glu Val Lys Glu Glu Ile Val Glu Asn Gly Val
65                  70                  75                  80
Lys Lys Leu Val His Ser Val Phe Asp Thr Ala Asp Tyr Thr Phe Pro
                85                  90                  95
Leu Gln Gly Asn Ser Phe Phe Val Met Thr Asn Phe Leu Lys Thr Glu
            100                 105                 110
Gly Gln Glu Gln Arg Leu Cys Pro Glu Tyr Pro Thr Arg Arg Thr Leu
        115                 120                 125
Cys Ser Ser Asp Arg Gly Cys Lys Lys Gly Trp Met Asp Pro Gln Ser
    130                 135                 140
Lys Gly Ile Gln Thr Gly Arg Cys Val Val Tyr Glu Gly Asn Gln Lys
145                 150                 155                 160
Thr Cys Glu Val Ser Ala Trp Cys Pro Ile Glu Ala Val Glu Glu Ala
                165                 170                 175
Pro Arg Pro Ala Leu Leu Asn Ser Ala Glu Asn Phe Thr Val Leu Ile
            180                 185                 190
Lys Asn Asn Ile Asp Phe Pro Gly His Asn Tyr Thr Thr Arg Asn Ile
        195                 200                 205
Leu Pro Gly Leu Asn Ile Thr Cys Thr Phe His Lys Thr Gln Asn Pro
    210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                245                 250                 255
Tyr Trp Asp Cys Asn Leu Asp Arg Trp Phe His His Cys Arg Pro Lys
            260                 265                 270
Tyr Ser Phe Arg Arg Leu Asp Asp Lys Thr Thr Asn Val Ser Leu Tyr
        275                 280                 285
```

Pro Gly Tyr Asn Phe Arg Tyr Ala Lys Tyr Tyr Lys Glu Asn Asn Val
            290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
                325                 330                 335

Ile Gly Ser Thr Leu Ser Tyr Phe Gly Leu Ala Thr Val Phe Ile Asp
                340                 345                 350

Phe Leu Ile Asp Thr Tyr Ser Ser Asn Cys Cys Arg Ser His Ile Tyr
            355                 360                 365

Pro Trp Cys Lys Cys Cys Gln Pro Cys Val Val Asn Glu Tyr Tyr Tyr
            370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
            530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 40
<211> LENGTH: 595
<212> TYPE: PRT
<213> ORGANISM: Macaca mulatta

<400> SEQUENCE: 40

Met Pro Ala Cys Cys Ser Cys Ser Asp Val Phe Gln Tyr Glu Thr Thr
1               5                   10                  15

Lys Val Thr Arg Ile Gln Ser Met Asn Tyr Gly Thr Ile Lys Trp Phe
                20                  25                  30

Phe His Val Ile Val Phe Ser Tyr Val Ser Phe Ala Leu Val Ser Asp
            35                  40                  45

Lys Leu Tyr Gln Arg Lys Glu Pro Val Ile Ser Ser Val His Thr Lys
        50                  55                  60

```
Val Lys Gly Thr Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                 85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Glu Gly Asn Arg Lys
145                 150                 155                 160

Thr Cys Glu Val Ser Ala Trp Cys Pro Ile Glu Ala Val Gly Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Thr Val Phe Ile Asp
            340                 345                 350

Phe Leu Ile Asn Thr Tyr Ser Ser Asn Tyr Cys Arg Ser His Ile Tyr
        355                 360                 365

Pro Trp Cys Lys Cys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Lys Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Lys Leu Pro Leu Ala Leu His Asp
        435                 440                 445

Pro Pro Pro Ile Pro Gly Gln Pro Gly Glu Met Gln Pro Leu Arg Glu
    450                 455                 460

Glu Ala Thr Pro Arg Ser Arg Asp Ser Pro Val Trp Cys Gln Cys Gly
465                 470                 475                 480
```

```
Ser Cys Leu Pro Ser Gln Leu Pro Lys Ser His Arg Cys Leu Glu Glu
                485                 490                 495

Leu Cys Cys Arg Lys Pro Gly Ala Cys Ile Thr Thr Ser Glu Leu
        500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
        530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 41
<211> LENGTH: 595
<212> TYPE: PRT
<213> ORGANISM: Callithrix pygmaea

<400> SEQUENCE: 41

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Leu Lys Trp Phe
            20                  25                  30

Phe His Val Ile Val Phe Ser Tyr Val Ser Phe Ala Leu Val Ser Asp
        35                  40                  45

Lys Leu Tyr Gln Arg Lys Glu Ser Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His His Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Gln Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Lys Gly Asn Gln Lys
145                 150                 155                 160

Thr Cys Glu Val Ser Ala Trp Cys Pro Ile Glu Ala Val Glu Asp Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Val Phe Arg Glu Thr Gly Asp
225                 230                 235                 240

Asn Phe Ser Glu Val Ala Ile Gln Gly Gly Ile Met Gly Ile Glu Ile
                245                 250                 255
```

Tyr Trp Asp Cys Asn Leu Asp Arg Trp Phe His His Cys Arg Pro Lys
              260                 265                 270

Tyr Ser Phe Arg Arg Leu Asp Asp Lys Thr Thr Asn Val Ser Leu Tyr
          275                 280                 285

Pro Gly Tyr Asn Phe Arg Tyr Ala Lys Tyr Tyr Lys Glu Asn Asn Val
      290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
              325                 330                 335

Ile Gly Ser Thr Leu Ser Tyr Phe Gly Leu Ala Thr Val Phe Ile Asp
              340                 345                 350

Phe Leu Ile Asn Thr Tyr Ser Ser Asn Cys Cys Arg Ser His Ile Tyr
          355                 360                 365

Pro Trp Cys Lys Cys Cys Arg Pro Cys Val Val Asn Glu Tyr Tyr Tyr
      370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
              405                 410                 415

Leu Gly Arg Arg Leu Gln Asp Val Lys Gly Gln Glu Val Pro Arg Pro
              420                 425                 430

Pro Val Asp Phe Thr Asp Leu Ser Lys Leu Pro Leu Ala Leu His Asp
          435                 440                 445

Pro Pro Pro Thr Pro Gly Gln Pro Glu Glu Met Gln Leu Leu Arg Glu
      450                 455                 460

Glu Thr Thr Pro Arg Pro Arg Asp Ser Pro Val Trp Cys Gln Cys Gly
465                 470                 475                 480

Ser Cys Leu Pro Ser Gln Leu Pro Glu Ser His Arg Cys Leu Glu Glu
              485                 490                 495

Leu Cys Cys Arg Lys Lys Pro Gly Ala Cys Ile Thr Thr Ser Glu Leu
              500                 505                 510

Phe Arg Lys Leu Val Leu Ser Arg His Ile Leu Gln Phe Leu Leu Leu
          515                 520                 525

Tyr Gln Asp Pro Leu Leu Ala Leu Asp Val Asp Ser Thr Asn Ser Gln
      530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
              565                 570                 575

Ile Arg Arg Glu Phe Pro Lys Ser Gln Gly Gln Tyr Ser Gly Phe Lys
              580                 585                 590

Ser Pro Tyr
      595

<210> SEQ ID NO 42
<211> LENGTH: 594
<212> TYPE: PRT
<213> ORGANISM: Ailuropoda melanoleuca

<400> SEQUENCE: 42

Met Pro Ala Cys Cys Ser Trp Lys Asp Val Phe Gln Tyr Glu Thr Asn
1               5                   10                  15

Lys Val Leu Arg Ile Gln Ser Thr Asn Tyr Gly Thr Ile Lys Trp Ile

-continued

```
                20                  25                  30
Phe His Val Leu Val Phe Ser Tyr Ile Ser Phe Ala Leu Ile Ser Asp
            35                  40                  45
Lys Arg Tyr Gln Lys Lys Glu Pro Leu Ile Ser Ser Val His Thr Lys
 50                  55                  60
Val Lys Gly Ile Ala Glu Val Lys Ala Glu Ile Leu Glu Asn Gly Met
 65                  70                  75                  80
Lys Lys Met Val Ser Gly Val Phe Asp Thr Ala Asp Tyr Thr Phe Pro
                85                  90                  95
Leu Gln Gly Asn Ser Phe Phe Val Met Thr Asn Phe Ile Lys Thr Glu
            100                 105                 110
Gly Gln Gln Gln Gly Leu Cys Pro Asp Phe Pro Thr Arg Arg Thr Ile
        115                 120                 125
Cys Ser Ser Asp Arg Gly Cys Lys Lys Gly Arg Met Asp Pro Gln Ser
    130                 135                 140
Lys Gly Ile Gln Thr Gly Arg Cys Val Val Tyr Lys Glu Arg Leu Lys
145                 150                 155                 160
Thr Cys Glu Val Ser Ala Trp Cys Pro Ile Glu Glu Val Glu Asp Ala
                165                 170                 175
Pro Arg Pro Ala Leu Leu Asn Ser Ala Glu Asn Phe Thr Val Leu Ile
            180                 185                 190
Lys Asn Asn Ile Asp Phe Pro Gly His Asn Tyr Thr Thr Arg Asn Ile
        195                 200                 205
Leu Pro Gly Val Asn Ile Thr Cys Thr Phe His Lys Thr Gln Asn Pro
    210                 215                 220
Gln Cys Pro Ile Phe Arg Leu Gly Asp Ile Phe Gln Glu Thr Gly Asp
225                 230                 235                 240
Asn Phe Ser Asp Val Ala Ile Gln Gly Gly Ile Met Gly Ile Glu Ile
                245                 250                 255
Tyr Trp Asp Cys Asn Leu Asp Gly Trp Phe His His Cys Arg Pro Lys
            260                 265                 270
Tyr Ser Phe Arg Arg Leu Asp Asp Lys Thr Thr Asn Glu Ser Leu Tyr
        275                 280                 285
Pro Gly Tyr Asn Phe Arg Tyr Ala Lys Tyr Tyr Lys Glu Asn Asn Val
    290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asn Val Ile Gln Leu Ala Val Tyr
                325                 330                 335
Ile Gly Ser Val Ile Ser Tyr Phe Gly Leu Ala Thr Val Phe Ile Asp
            340                 345                 350
Ile Leu Ile Asn Thr Tyr Ser Ser Lys Cys Cys Arg Ser Arg Ile Tyr
        355                 360                 365
Pro Cys Phe Lys Cys Cys Glu Tyr Cys Ala Val Asn Glu Tyr Tyr Tyr
    370                 375                 380
Arg Lys Gln Ser Glu Pro Ile Ala Glu Pro Lys Pro Thr Leu Lys Tyr
385                 390                 395                 400
Val Ser Phe Val Asp Glu Thr His Ile Arg Met Val Asp Gln Gln Leu
                405                 410                 415
Leu Gly Lys Ser Leu Gln Asn Val Lys Gly Glu Lys Val Gln Arg Pro
            420                 425                 430
Ser Val Asp Phe Thr Asp Leu Ser Arg Leu Ser Leu Ser Leu Cys Asp
        435                 440                 445
```

-continued

Pro Thr Pro Ile Pro Gly Gln Pro Glu Glu Met Gln Leu Phe Ser Glu
        450                 455                 460

Glu Val Thr Pro Arg Ser Ser Asn Ser Pro Asp Trp Cys Gln Cys Gly
465                 470                 475                 480

His Cys Leu Pro Ser Gln Leu Pro Glu Ser His Arg Cys Leu Glu Glu
            485                 490                 495

Leu Cys Cys Arg Lys Lys Ala Gly Ala Cys Ile Thr Thr Ser Glu Pro
            500                 505                 510

Phe Arg Lys Leu Val Leu Ser Arg Gln Val Leu Gln Phe Leu Leu Leu
            515                 520                 525

Tyr Gln Glu Pro Leu Leu Val Leu Asp Gly Asn Ser Ser Ser Arg Leu
        530                 535                 540

Arg His Cys Ala Tyr Arg Cys Tyr Thr Thr Trp Arg Phe Gly Ser Pro
545                 550                 555                 560

Asp Leu Ala Asp Phe Ala Ile Leu Pro Ser Cys Cys Arg Trp Arg Ile
            565                 570                 575

Arg Arg Glu Phe Pro Lys Ser Glu Gly Gln Tyr Thr Gly Phe Gln Ser
            580                 585                 590

Pro Tyr

<210> SEQ ID NO 43
<211> LENGTH: 595
<212> TYPE: PRT
<213> ORGANISM: Equus caballus

<400> SEQUENCE: 43

Met Pro Ala Cys Cys Ser Trp Asn Asp Val Phe Gln Tyr Glu Thr Asn
1               5                   10                  15

Lys Val Thr Arg Ile Gln Ser Met Asn Tyr Gly Thr Ile Lys Trp Ile
            20                  25                  30

Cys His Leu Ile Val Phe Ser Tyr Val Ile Phe Ala Leu Val Ser Asp
        35                  40                  45

Lys Arg Tyr Gln Arg Lys Glu Pro Leu Ile Ser Ser Val His Thr Lys
    50                  55                  60

Val Lys Gly Ile Ala Glu Val Arg Glu Glu Ile Ile Glu Ser Gly Ala
65                  70                  75                  80

Lys Lys Val Val Gln Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Gly Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Ile Val Tyr Lys Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Phe
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

His Phe Ser Asp Val Ala Ile Gln Gly Gly Ile Met Gly Ile Glu Ile
            245                 250                 255

Tyr Trp Asp Cys Asn Leu Asp Arg Trp Phe His His Cys Arg Pro Lys
        260                 265                 270

Tyr Ser Phe Arg Arg Leu Asp Asp Lys Thr Ala Ser Glu Ser Ser Tyr
    275                 280                 285

Pro Gly Tyr Asn Phe Arg Tyr Ala Lys Tyr Tyr Lys Glu Asn Asn Val
290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Ile Val Phe
            325                 330                 335

Val Gly Ser Thr Leu Ser Tyr Phe Gly Leu Ala Thr Leu Phe Ile Asp
            340                 345                 350

Phe Leu Ile Asn Thr Tyr Ser Lys Phe Cys Arg Ser Ser Ile Tyr
            355                 360                 365

Pro Cys Cys Lys Tyr Cys Glu Pro Cys Ser Val Asn Glu Tyr Tyr
370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asp Gln Gln Leu
                405                 410                 415

Leu Gly Arg Ser Leu Gln Asp Val Lys Gly Glu Lys Val Pro Arg Pro
            420                 425                 430

Ser Met Asp Phe Thr Asp Leu Ser Arg Leu Pro Leu Ser Leu Gln Asp
            435                 440                 445

Pro His Val Thr Pro Gly Gln Pro Glu Asp Ile Gln Leu Leu Ser Glu
            450                 455                 460

Glu Val Thr Pro Arg His Lys Asp Ser Pro His Trp Cys Gln Cys Gly
465                 470                 475                 480

Asn Cys Leu Pro Ser Gln Leu Pro Glu Ser His Arg Cys Leu Glu Glu
                485                 490                 495

Leu Cys Cys Arg Lys Lys Met Gly Ala Cys Ile Thr Thr Ser Glu Pro
            500                 505                 510

Phe Arg Lys Leu Val Leu Ser Arg Arg Val Leu Gln Phe Leu Leu Leu
            515                 520                 525

Tyr Arg Glu Pro Leu Leu Val Leu Asp Ala Asp Ser Thr Asn Ser Gln
            530                 535                 540

Leu Arg His Cys Ala Tyr Arg Cys Tyr Ala Thr Trp Arg Phe Gly Ser
545                 550                 555                 560

Gln Asp Leu Ala Asp Phe Ala Ile Leu Pro Ser Cys Cys Arg Trp Arg
                565                 570                 575

Ile Arg Arg Glu Phe Pro Arg Ser Glu Gly Gln Tyr Gly Gly Phe Lys
            580                 585                 590

Ser Pro Tyr
        595

<210> SEQ ID NO 44
<211> LENGTH: 595
<212> TYPE: PRT
<213> ORGANISM: Bos taurus

<400> SEQUENCE: 44

```
Met Thr Ala Cys Cys Ser Trp Asn Asp Val Phe Gln Tyr Glu Thr Asn
1               5                   10                  15

Lys Ile Ile Trp Ile Gln Ser Lys Thr Tyr Gly Thr Ile Lys Trp Leu
            20                  25                  30

Phe His Val Val Leu Phe Ser Tyr Ile Gly Phe Ala Leu Val Ser Asp
        35                  40                  45

Lys Arg Tyr Gln Arg Lys Glu Pro Val Ile Ser Ser Val His Ser Lys
    50                  55                  60

Ile Lys Gly Ile Ala Glu Val Lys Lys Glu Ile Met Glu Asn Gly Gln
65                  70                  75                  80

Thr Lys Val Val Gln Ser Val Phe Asp Met Ala Asp Tyr Thr Phe Pro
                85                  90                  95

Leu Gln Gly Asn Ser Phe Phe Met Met Thr Asn Phe Leu Lys Thr Glu
            100                 105                 110

Gly Gln Glu Gln Gly Leu Cys Pro Glu Tyr Pro Thr Pro Arg Thr Leu
        115                 120                 125

Cys Ser Ser Asp Arg Gly Cys Lys Lys Gly Trp Leu Gly Pro Arg Ser
    130                 135                 140

Lys Gly Ile Gln Thr Gly Arg Cys Ile His Tyr Asn Glu Lys Gln Lys
145                 150                 155                 160

Thr Cys Glu Val Phe Thr Trp Cys Pro Val Glu Ala Glu Glu Lys Ala
                165                 170                 175

Pro Glu Pro Ala Leu Leu Val Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Thr Thr Cys Thr Phe His Lys Thr Arg Asp Pro
    210                 215                 220

Gln Cys Pro Ile Phe Arg Leu Gly Asp Ile Phe Gln Glu Thr Gly Asp
225                 230                 235                 240

Asn Phe Ser Glu Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Ala Lys Glu Ser Leu Tyr
        275                 280                 285

Pro Gly Tyr Asn Phe Arg Tyr Ala Lys Tyr Tyr Lys Glu Asn Asn Thr
    290                 295                 300

Glu Lys Arg Thr Leu Ile Lys Ala Tyr Gly Ile Arg Phe Asp Ile Leu
305                 310                 315                 320

Val Phe Gly Thr Gly Gly Lys Phe Asp Ile Ile Gln Leu Ile Val Tyr
                325                 330                 335

Ile Gly Ser Thr Leu Ser Tyr Phe Gly Leu Ala Thr Val Phe Ile Asp
            340                 345                 350

Met Leu Ile Asn Thr Tyr Ser Ser Lys Tyr Cys Arg Ser His Val Tyr
        355                 360                 365

Pro Trp Cys Lys Cys Cys Gln Pro Cys Ala Val Asn Gly Tyr Tyr Tyr
    370                 375                 380

Lys Lys Lys Tyr Glu Ser Ile Val Glu Pro Thr Arg Thr Leu Lys Tyr
385                 390                 395                 400

Val Ser Phe Val Asp Glu Pro Cys Ile Arg Met Val Asn Glu Arg Leu
                405                 410                 415
```

```
Leu Gly Thr Ser Leu Gln Ala Val Lys Gly Glu Lys Val Leu Arg Pro
            420                 425                 430

Gln Leu Asp Phe Ala Asp Leu Ser Trp Leu His Leu Ser Leu His Asp
            435                 440                 445

Ser Pro Pro Ile Pro Gly Gln Pro Glu Glu Ile Gln Leu Leu Ser Glu
            450                 455                 460

Glu Val His Leu Lys Ser Arg Asp Cys Pro Asp Trp Cys Gln Cys Gly
465                 470                 475                 480

Asn Cys Leu Pro Ser Gln Leu Pro Glu Asn Gln Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Asp Leu Val Leu Ser Arg Arg Ala Leu Gln Phe Leu Leu Gln
            515                 520                 525

Tyr Gln Glu Pro Leu Leu Val Leu Asp Ala Asp Ser Ala Asn Ser Arg
            530                 535                 540

Leu Arg His Cys Ala Tyr Arg Ser Tyr Thr Ala Trp Arg Phe Gly Ser
545                 550                 555                 560

Gln Asp Leu Ala Asp Phe Ala Ile Leu Pro Ser Cys Cys Arg Trp Arg
                565                 570                 575

Ile Arg Arg Glu Phe Pro Lys Ser Glu Gly Gln Tyr Ser Gly Phe Lys
            580                 585                 590

Ser Pro Tyr
        595

<210> SEQ ID NO 45
<211> LENGTH: 595
<212> TYPE: PRT
<213> ORGANISM: Oryctolagus cuniculus

<400> SEQUENCE: 45

Met Pro Ala Cys Cys Ser Trp Asn Asp Val Phe Gln Tyr Glu Thr Asn
1               5                   10                  15

Lys Val Ala Arg Ile Gln Ser Val Asn Tyr Gly Thr Ile Lys Trp Val
            20                  25                  30

Leu His Val Ile Val Phe Ser Tyr Val Ser Phe Ala Leu Val Ser Asp
            35                  40                  45

Lys Leu Tyr Gln Arg Lys Glu Pro Val Ile Ser Ser Val His Thr Lys
        50                  55                  60

Val Lys Gly Ile Ala Glu Val Lys Glu Val Leu Val Glu Asn Gly Val
65                  70                  75                  80

Lys Lys Glu Val Gly Ser Ile Phe Asp Thr Ala Asp Tyr Thr Phe Pro
                85                  90                  95

Leu Gln Arg Asn Ser Phe Phe Val Met Thr Asn Phe Leu Lys Thr Glu
            100                 105                 110

Gly Gln Glu Arg Arg Leu Cys Pro Glu Tyr Pro Thr Arg Arg Thr Leu
            115                 120                 125

Cys Ser Ser Asp Arg Gly Cys Arg Lys Gly Trp Met Asp Pro Gln Ser
        130                 135                 140

Lys Gly Ile Gln Thr Gly Arg Cys Val Val Tyr Lys Gly Asn Gln Lys
145                 150                 155                 160

Thr Cys Glu Val Ser Ala Trp Cys Pro Ile Glu Ala Ala Glu Asp Ala
                165                 170                 175

Pro Arg Pro Ala Leu Leu Gly Ser Ala Glu Asn Phe Thr Val Leu Ile
```

-continued

```
            180                 185                 190
Lys Asn Asn Ile Asp Phe Pro Gly His Asn Tyr Thr Thr Arg Asn Ile
            195                 200                 205
Pro Pro Gly Leu Asn Ile Ser Cys Thr Phe His Lys Thr Gln Asn Pro
            210                 215                 220
Gln Cys Pro Ile Phe Arg Leu Gly Asp Ile Phe Arg Glu Thr Gly Asp
225                 230                 235                 240
Arg Phe Ser Asp Val Ala Val Gln Gly Ile Met Gly Ile Glu Ile
                    245                 250                 255
Tyr Trp Asp Cys Asn Leu Asp Arg Trp Phe His Arg Cys Arg Pro Lys
                    260                 265                 270
Tyr Ser Phe Arg Arg Leu Asp Asp Lys Thr Ala Asn Glu Ser Leu Tyr
                    275                 280                 285
Pro Gly Tyr Asn Phe Arg Tyr Ala Lys Tyr Tyr Lys Glu Asn Asn Val
                    290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Ile Val Tyr
                    325                 330                 335
Ile Gly Ser Thr Leu Ser Tyr Phe Gly Leu Ala Thr Val Cys Ile Asp
                    340                 345                 350
Phe Leu Ile Asn Thr Tyr Ser Ser Asn Cys Cys Arg Ser His Ile Tyr
                    355                 360                 365
Pro Arg Cys Thr Cys Cys Glu Pro Cys Ala Ala Asn Glu Tyr Tyr His
                    370                 375                 380
Arg Lys Lys Tyr Glu Ser Leu Val Glu Pro Arg Arg Thr Leu Lys Tyr
385                 390                 395                 400
Val Ser Phe Val Asp Glu Pro His Ile Arg Met Val Asp Gln Gln Leu
                    405                 410                 415
Leu Gly Lys Ser Leu Gln Asp Val Pro Gly Gln Lys Ile Pro Arg Pro
                    420                 425                 430
Pro Arg Asp Phe Thr Asp Leu Ser Lys Leu Pro Leu Ser Phe Leu Asp
                    435                 440                 445
Pro His Pro Thr Pro Gly Gln Ala Glu Glu Met Gln Pro Leu Ser Glu
                    450                 455                 460
Gly Glu Thr Ala Arg Ser Arg Gly Cys Pro Asp Trp Cys Gln Cys Gly
465                 470                 475                 480
Asn Cys Leu Pro Ser Gln Leu Pro Ala Ser His Arg Cys Leu Glu Glu
                    485                 490                 495
Leu Cys Cys Arg Arg Lys Pro Gly Ala Cys Val Thr Thr Ser Gln Leu
                    500                 505                 510
Phe Gly Lys Leu Val Leu Ser Lys Pro Thr Leu Gln Phe Leu Leu Leu
                    515                 520                 525
Tyr Gln Glu Pro Leu Leu Ala Leu Asp Ala Glu Ala Thr Thr Ser Gln
                    530                 535                 540
Leu Arg His Cys Ala Tyr Arg Cys Tyr Ile Ala Trp Arg Phe Gly Ser
545                 550                 555                 560
Gln Asp Leu Ala Asp Phe Ala Ile Leu Pro Ser Cys Cys Arg Trp Arg
                    565                 570                 575
Ile Arg Lys Glu Phe Pro Lys Ser Glu Gly Pro Tyr Ser Gly Phe Lys
                    580                 585                 590
Ser Pro Tyr
            595
```

<210> SEQ ID NO 46
<211> LENGTH: 594
<212> TYPE: PRT
<213> ORGANISM: Cavia porcellus

<400> SEQUENCE: 46

```
Met Pro Gly Cys Ser Cys Trp Asp Val Phe Gln Tyr Glu Thr Asn
1               5                   10                  15

Lys Val Thr Arg Ile Gln Ser Arg Asn Tyr Gly Thr Leu Lys Trp Val
                20                  25                  30

Leu His Leu Ile Val Phe Ser Tyr Ile Ser Phe Ala Leu Val Thr Asp
            35                  40                  45

Lys Met Tyr Gln Arg Lys Glu Pro Val Ile Ser Ser Val His Ser Lys
        50                  55                  60

Val Lys Gly Met Ala Glu Val Thr Glu Glu Val Gly Gly Val Arg
65                  70                  75                  80

Arg Ser Val Gln Lys Val Leu Asp Thr Ala Asp Tyr Thr Leu Pro Leu
                85                  90                  95

Gln Gly Asn Ser Phe Phe Val Met Thr Asn Tyr Leu Gln Thr Glu Gly
            100                 105                 110

Gln Glu Arg Gly Leu Cys Pro Glu Tyr Pro Thr Pro Arg Thr Arg Cys
        115                 120                 125

Ser Ser Asp Arg Gly Cys Lys Lys Gly Trp Arg Asp Pro Lys Ser Lys
    130                 135                 140

Gly Ile Gln Thr Gly Arg Cys Val Val Tyr Ser Gly Thr Thr Lys Thr
145                 150                 155                 160

Cys Glu Val Ala Ala Trp Cys Pro Val Glu Ala Val Ile Glu Ala Pro
                165                 170                 175

Arg Pro Ala Ile Leu Ser Ser Ala Glu Asn Leu Thr Val Leu Ile Lys
            180                 185                 190

Asn Asn Val His Phe Pro Gly His Asn Tyr Thr Thr Arg Asn Ile Leu
        195                 200                 205

Pro Gly Leu Asn Ala Ser Cys Thr Phe His Lys Thr Lys Asn Pro Glu
    210                 215                 220

Cys Pro Ile Phe Arg Leu Gly Asp Ile Phe Gln Glu Ala Gly Asp Asn
225                 230                 235                 240

Phe Ser Asp Val Ala Val Gln Gly Gly Ile Met Gly Ile Glu Ile Asn
                245                 250                 255

Trp Asp Cys Asn Leu Asp Lys Trp Ser His His Cys Arg Pro Lys Tyr
            260                 265                 270

Ser Phe Arg Arg Leu Asp Asp Lys Ser Val Glu Glu Ile Leu Val Pro
        275                 280                 285

Gly Tyr Asn Phe Arg Tyr Ala Lys Tyr Tyr Arg Glu Asn Asn Val Glu
    290                 295                 300

Lys Arg Thr Leu Ile Lys Val Phe Gly Val Arg Phe Asp Ile Leu Val
305                 310                 315                 320

Phe Gly Thr Gly Gly Lys Phe Asp Ile Ile Ser Leu Ile Val Tyr Ile
                325                 330                 335

Gly Ser Thr Leu Ser Tyr Phe Gly Leu Ala Thr Val Phe Ile Asp Phe
            340                 345                 350

Leu Ile Asn Thr Tyr Ser Ser Ala Leu Cys Arg Ser His Val Tyr Pro
        355                 360                 365

Trp Cys Pro Cys Cys Lys Pro Cys Ala Ala Asn Glu Tyr Tyr Tyr Arg
```

```
            370                 375                 380
Lys Lys Cys Gln Ala Thr Val Glu Pro Lys Pro Thr Leu Lys Tyr Val
385                 390                 395                 400

Ser Phe Val Asp Glu Pro His Ile Arg Met Val Asp Gln Arg Leu Leu
                405                 410                 415

Gly Lys Ser Leu Gln Tyr Val Lys Gly Gln Lys Val Pro Arg Pro Pro
                420                 425                 430

Thr Asp Phe Thr Leu Leu Ser Lys Leu Pro Thr Ser Pro Pro Asp Pro
                435                 440                 445

Ala Pro Ala Pro Thr Gln Leu Glu Glu Met Gln Pro Leu Arg Arg Pro
450                 455                 460

Asp Thr Ser Ala Ser Gly Asp Ser Pro Glu Trp Cys Gln Cys Gly Ser
465                 470                 475                 480

Cys Arg Pro Ser Gln Leu Pro Lys Asp Ser Arg Cys Leu Glu Glu Leu
                485                 490                 495

Cys Cys Arg Arg Gly Pro Gly Pro Cys Ile Thr Thr Ser Glu Leu Phe
                500                 505                 510

Gly Asp Leu Val Leu Ser Arg Pro Ala Leu Arg Gln Leu Leu Leu Tyr
                515                 520                 525

Gln Glu Pro Leu Leu Val Leu Asp Gly Glu Ala Thr Asn Ser Gly Leu
                530                 535                 540

Arg His Cys Ala Tyr Arg Cys Tyr Thr Thr Trp Arg Phe Gly Ala Gln
545                 550                 555                 560

Asp Val Ala Asp Phe Gly Ile Leu Pro Ser Cys Cys Arg Trp Arg Ile
                565                 570                 575

Arg Ser Glu Phe Pro Arg Ser His Gly Gln Tyr Ser Gly Phe Arg Cys
                580                 585                 590

Pro Tyr

<210> SEQ ID NO 47
<211> LENGTH: 594
<212> TYPE: PRT
<213> ORGANISM: Monodelphis domestica

<400> SEQUENCE: 47

Met Trp Pro Cys Cys Ser Trp Arg Asp Ile Cys Lys Tyr Glu Thr Thr
1               5                   10                  15

Lys Val Ile Arg Val Glu Ser Met Thr Tyr Gly Thr Leu Arg Trp Ser
                20                  25                  30

Leu Cys Ala Ile Val Phe Phe Tyr Val Cys Val Gly Leu Leu Ser Asp
            35                  40                  45

Lys Leu Tyr Gln Arg Lys Glu Pro Leu Ile Ser Ser Val Gln Thr Lys
    50                  55                  60

Val Lys Gly Ile Ala Glu Val Lys Asn Gly Asn Ser Lys Thr Arg Val
65                  70                  75                  80

Leu Asp Thr Ala Asp Tyr Thr Ile Pro Leu Gln Gly Asn Ser Phe Phe
                85                  90                  95

Val Met Thr Asn Phe Ile Ser Thr Glu Gly Gln Thr Gln Gly Leu Cys
                100                 105                 110

Pro Glu Tyr Pro Thr Arg Arg Thr Leu Cys Ser Thr Asp Gln Gly Cys
            115                 120                 125

Lys Lys Gly Lys Lys Asp Pro Leu Ser Lys Gly Ile Gln Thr Gly Lys
    130                 135                 140

Cys Val Leu Tyr Ser Thr Thr Gln Lys Thr Cys Glu Val Ser Ala Trp
```

```
            145                 150                 155                 160
Cys Pro Val Glu Gln Glu Arg Asp Pro Arg Pro Ala Leu Leu Ile Ser
                    165                 170                 175

Ala Ala Asn Phe Thr Val Leu Ile Lys Asn Asn Ile Asp Phe Pro Gly
                    180                 185                 190

His Asn Tyr Thr Thr Arg Asn Ile Leu Pro Gly Val Asn Ile Thr Cys
                    195                 200                 205

Met Phe His Arg Thr His Asn Pro Gln Cys Pro Ile Phe Arg Leu Gly
                    210                 215                 220

Asp Ile Phe Gln Glu Val Gly Glu Asn Phe Ser Asp Val Ala Val Gln
225                 230                 235                 240

Ser Glu Ile Met Ser Ile Glu Ile Tyr Trp Asn Cys Asn Leu Asp Ser
                    245                 250                 255

Trp Phe His Ser Cys Arg Pro Lys Tyr Ser Phe Arg Arg Leu Asp Asp
                    260                 265                 270

Arg Thr Thr Ile Glu Ser Leu Tyr Pro Gly Tyr Asn Phe Arg Phe Ala
                    275                 280                 285

Arg Tyr Tyr Lys Glu Gly Asn Val Glu Lys Arg Asp Leu Ile Lys Ala
                    290                 295                 300

Phe Gly Ile Arg Phe Asp Ile Leu Val Phe Gly Thr Gly Gly Lys Phe
305                 310                 315                 320

Asp Phe Ile Gln Met Val Val Tyr Ile Gly Ser Thr Leu Ser Tyr Phe
                    325                 330                 335

Gly Leu Ala Thr Val Phe Ile Asp Phe Leu Ile Asp Thr Tyr Ser Ser
                    340                 345                 350

Thr Cys Cys Arg Thr His Val Tyr Pro Cys Cys Lys Ala Cys Glu Pro
                    355                 360                 365

Cys Gly Val Asn Glu Tyr Tyr Arg Lys Lys Cys Glu Thr Ile Glu
                    370                 375                 380

Glu Pro Lys Pro Thr Leu Lys Tyr Val Ser Phe Val Asp Glu Pro His
385                 390                 395                 400

Ile Arg Lys Val Asp Gln Leu Leu Gly Lys Ser Leu Gln Glu Val
                    405                 410                 415

Ala Gly Gln Glu Val Pro Arg Pro Arg Arg Asn Phe Thr Asp Leu Ala
                    420                 425                 430

Lys Leu Ser Pro Pro Gln Pro Gly Met Asp Pro Ser Pro Ala Gly
                    435                 440                 445

Pro Glu Glu Met Gln Leu Leu Lys Asp Arg Pro Ser Pro Ser Gln
450                 455                 460

Gly Lys Leu Lys Trp Cys Cys Cys Gly His Cys Arg Pro Ser Gln Leu
465                 470                 475                 480

Pro Glu Gly Thr Arg Cys Leu Glu Glu Leu Cys Cys Arg Arg Lys Gly
                    485                 490                 495

Gly Pro Cys Ile Thr Thr Ser Ala Leu Phe Glu Glu Leu Val Leu Ser
                    500                 505                 510

Arg Ala Thr Leu Arg Phe Ile Leu Leu Tyr Gln Glu Pro Leu Leu Glu
                    515                 520                 525

Met Asp Ala Ala Thr Leu Asn Asn Arg Leu Arg Arg Cys Ala Tyr Glu
                    530                 535                 540

Arg Tyr Ile Asp Trp Arg Phe Gly Ser Glu Asp Met Ala Gly Phe Ala
545                 550                 555                 560

Ile Leu Pro Ser Cys Cys Arg Trp Met Ile Arg Asp His Phe Pro Lys
                    565                 570                 575
```

```
Gln Asp Gly Lys Tyr Thr Gly Phe Lys Ser Pro Ser Pro Tyr Thr Phe
            580                 585                 590
Leu Glu

<210> SEQ ID NO 48
<211> LENGTH: 576
<212> TYPE: PRT
<213> ORGANISM: Sparus aurata

<400> SEQUENCE: 48

Met Pro Cys Cys Gly Leu Arg Gly Leu Arg Gln Tyr Glu Thr Asn Lys
1               5                   10                  15

Leu Val Arg Ile Gln Ser Val Arg Leu Gly Ser Met Lys Trp Ser Leu
            20                  25                  30

Asn Gly Phe Ile Leu Leu Phe Ile Cys Ile Met Met Leu Trp Asn Arg
        35                  40                  45

Lys Tyr Gln Glu Phe Asp Leu Val Val Ser Ser Val His Thr Lys Val
    50                  55                  60

Lys Gly Val Ala Gln Thr Leu Gly Asp Met Val Trp Asp Val Val Asp
65                  70                  75                  80

Tyr Ser Gly Pro Ser His Asp Lys Asn Ser Phe Val Val Thr Asn
                85                  90                  95

Val Ile Val Thr Lys Asn Gln Lys Gln Gly Lys Cys Pro Glu Val Leu
            100                 105                 110

Arg Ile Gly Arg Leu Cys Arg Thr Asp Lys Asp Cys Gly Arg Gly Ala
        115                 120                 125

Trp Asp Gln Gln Ser His Gly Ile Gln Thr Gly Ser Cys Val Ile Ser
    130                 135                 140

Asp Val Ser Lys Lys Thr Cys Glu Val Ser Ala Trp Cys Pro Ile Glu
145                 150                 155                 160

Lys Arg Gly Asn Pro Pro Arg Pro Ala Leu Leu Ala Ala Ala Glu Asp
                165                 170                 175

Phe Thr Val Leu Ile Lys Asn Asn Ile Arg Phe Pro Ala Phe Asn Phe
            180                 185                 190

Ile Arg Arg Asn Ile Leu Pro Thr Met Asn Gly Ala Tyr Leu Ser Ser
        195                 200                 205

Cys Gln Arg Val Asn Asp Ser Leu Cys Pro Ile Phe Arg Leu Gly Asp
    210                 215                 220

Ile Ala Arg Glu Ala Gly Glu Lys Phe Ser Glu Met Ala Val Glu Gly
225                 230                 235                 240

Gly Val Ile Gly Ile Leu Ile Lys Trp Asp Cys Asn Leu Asp Trp Leu
                245                 250                 255

Met Gln Arg Cys Leu Pro Lys Tyr Ser Phe Arg Arg Leu Asp Glu Lys
            260                 265                 270

Glu Ser Asn Arg Thr Leu Tyr Pro Gly Leu Asn Phe Arg Tyr Ala Lys
        275                 280                 285

Tyr Asn Thr Val Asn Gly Val Glu Glu Arg Thr Leu Tyr Lys Ala Phe
    290                 295                 300

Gly Ile Arg Phe Asp Val Met Val Phe Gly Gln Ala Gly Lys Phe Ser
305                 310                 315                 320

Phe Ile Gln Leu Ile Ile Tyr Ile Gly Ser Thr Leu Ser Tyr Ala
                325                 330                 335

Leu Thr Thr Met Leu Ile Asp Trp Leu Ile Gly Thr Ser Cys Tyr Ser
            340                 345                 350
```

Val Glu Val Gly Gln Asn Tyr Ser Glu Lys Val Glu Ala Val Gln
            355                 360                 365

Asp Lys Gln Lys Cys Ile Leu Cys Val Ser Tyr Ile Asp Glu Asn Asn
370                 375                 380

Ile Arg Leu Val Lys Arg Ser Gln Lys Ser Leu Gln Asp Val Lys
385                 390                 395                 400

Ala Ala Ser Val Gln Pro Arg Lys Glu Asp Thr Gly His Leu Arg Ala
                405                 410                 415

Val Leu Ser Leu Leu Gln Ser Gly Val Gly Ala Asn His Asp Ala Gln
            420                 425                 430

Pro Pro His Glu His Lys Pro Asp Pro Lys Gln Lys Pro Cys Arg Pro
                435                 440                 445

Ala Trp Cys Lys Cys Asp His Cys Thr Pro Ser Ser Val Pro Gln Glu
        450                 455                 460

Glu Leu Cys Cys Arg Gln Ser Ala Gly Pro Cys Ile Thr Ser Ser Pro
465                 470                 475                 480

Leu Phe Gly Gln Leu Val Leu Ser His Ser Leu Leu Glu Ala Val Leu
                485                 490                 495

Leu Tyr Arg Asp Pro Leu Ser Ser Leu Ala Asp Arg Gly Gln Ala Ala
            500                 505                 510

Ser Leu Arg His Cys Ala Tyr Arg Gln Tyr Ile Ser Trp Arg Phe Gly
            515                 520                 525

Val Pro Pro Asn Asp Thr His Pro Val Ile Pro Ser Cys Cys Val Trp
            530                 535                 540

Arg Val Arg Glu Glu Tyr Pro Ser Pro Asp Gly Gln Tyr Ser Gly Phe
545                 550                 555                 560

Arg Pro Val Arg Ile Val Ser Met Gln Ala Cys Thr Asn Gly Glu Leu
                565                 570                 575

<210> SEQ ID NO 49
<211> LENGTH: 596
<212> TYPE: PRT
<213> ORGANISM: Danio rerio

<400> SEQUENCE: 49

Met Pro Cys Val Leu Leu Asn Leu Cys Glu Tyr Asp Thr Gln Lys Leu
1               5                   10                  15

Val Lys Ile Lys Ser Val Lys Leu Gly Ser Leu Lys Trp Thr Leu Asn
                20                  25                  30

Gly Val Ile Leu Met Phe Ile Cys Ile Met Met Leu Trp Asn Lys Glu
            35                  40                  45

Tyr Gln Glu Tyr Asp Phe Val Val Ser Ser Val Thr Thr Lys Val Lys
        50                  55                  60

Gly Val Ala Lys Ile Thr Leu Pro Glu Val Gly Asp Val Val Trp Asp
65                  70                  75                  80

Val Val Asp Tyr Ser Gly Pro Ser Gln Gly Lys Asn Ser Phe Phe Val
                85                  90                  95

Ala Thr Asn Ala Ile Val Thr Lys Asn Gln Lys Gln Gly Asn Cys Ala
            100                 105                 110

Glu Ile Leu Pro Asn Gly Lys Leu Cys Arg Thr Asp Lys Asp Cys Glu
        115                 120                 125

Lys Gly Phe Ser Asp Gln His Ser His Gly Val Gln Thr Gly Ala Cys
    130                 135                 140

Val Lys Leu Glu Ile Leu Lys Lys Thr Cys Glu Val Thr Ala Trp Cys

-continued

```
            145                 150                 155                 160
        Pro Ile Glu Asn Lys Lys Asn Pro Arg Pro Ala Leu Leu Ala Ala Ala
                        165                 170                 175
        Glu Asn Phe Thr Val Met Ile Lys Asn Asn Ile Arg Phe Pro Ala Phe
                        180                 185                 190
        Asn Tyr Ile Arg Arg Asn Ile Leu Ser Glu Met Lys Asp Thr Asp Phe
                        195                 200                 205
        Lys Gly Cys Ile Tyr His Arg Tyr Lys Asn Pro Tyr Cys Pro Ile Phe
                        210                 215                 220
        Arg Leu Gly Asp Ile Val Ala Glu Ala Lys Glu Lys Phe Ser Glu Met
        225                 230                 235                 240
        Ala Val Glu Gly Gly Val Ile Gly Ile Gln Ile Asn Trp Asp Cys Asp
                        245                 250                 255
        Leu Asn Arg Phe Phe His Ser Cys Leu Pro Lys Tyr Ser Phe Arg Arg
                        260                 265                 270
        Leu Asp Glu Lys Glu Ser Asn Arg Thr Leu Tyr Pro Gly Leu Asn Phe
                        275                 280                 285
        Arg Phe Ala Arg Tyr Ser Thr Val Asn Gly Val Glu Gln Arg Thr Leu
                        290                 295                 300
        Phe Lys Met Tyr Gly Ile Arg Phe Asp Val Met Val Phe Gly Lys Ala
        305                 310                 315                 320
        Gly Lys Phe Ser Ile Ile Gln Leu Ile Ile Tyr Ile Gly Ser Thr Leu
                        325                 330                 335
        Ser Tyr Tyr Ala Ile Thr Thr Ile Phe Leu Asp Trp Leu Ile Gly Thr
                        340                 345                 350
        Gly Cys Tyr Ser Lys Glu Ala Lys Gln Asn Tyr Thr Glu Arg Lys Phe
                        355                 360                 365
        Glu Ala Val Gln Asp Arg Glu Glu Cys Phe Leu Cys Val Ser Phe Val
                        370                 375                 380
        Asp Glu Asp Asn Leu Arg Val Val Lys Ser Arg Lys Lys Arg Leu
        385                 390                 395                 400
        Gln Glu Thr Lys Pro Leu Ser Leu His Gln Arg Lys Asn Glu Leu Ala
                        405                 410                 415
        Ser Met Lys Thr Leu Leu Ser Val Leu Gln Cys Gly Gln Ser Arg Ser
                        420                 425                 430
        Glu Pro Val Gln Asn Gly Gln Ser Gly Gly Leu Ile Val Asp Glu Asn
                        435                 440                 445
        Leu Ser Ser Arg His Asn Gly Arg Gln Asn Pro Asp Thr Pro Leu Leu
                        450                 455                 460
        Glu Thr Thr Gln Ser Ser Ser Pro Thr Trp Cys Gln Cys Gly Ser Cys
        465                 470                 475                 480
        Arg Pro Ala Glu Thr Leu Gln Glu Gln Leu Cys Cys Arg Leu Lys Lys
                        485                 490                 495
        Gly Arg Cys Ile Thr Ser Ser Pro Ile Phe Ser Ser Leu Ile Val Ser
                        500                 505                 510
        Arg Ser Val Leu Glu Asn Ala Leu Phe Phe Val Asp Pro Leu Ala Glu
                        515                 520                 525
        Leu His Glu Glu Ser Gln Leu Arg His Gly Ala Tyr Ala Gln Phe Ile
                        530                 535                 540
        Arg Trp Arg Phe Gly Asp Ser Thr Pro Arg Asp Ala Leu Pro Val Ile
        545                 550                 555                 560
        Pro Ser Cys Cys Ile Trp Arg Ile Arg Ala Glu Tyr Pro Ser Pro Asp
                        565                 570                 575
```

```
Gly Thr Tyr Arg Gly Leu Arg Ser Phe Gln Val Ile Thr Ser Gln Thr
            580                 585                 590

Glu Val Asn Arg
        595

<210> SEQ ID NO 50
<211> LENGTH: 17
<212> TYPE: PRT
<213> ORGANISM: Homo sapiens

<400> SEQUENCE: 50

Lys Tyr Tyr Lys Glu Asn Asn Val Glu Lys Arg Thr Leu Ile Lys Val
1               5                   10                  15

Phe
```